US010722523B2

(12) United States Patent
Karin et al.

(10) Patent No.: US 10,722,523 B2
(45) Date of Patent: Jul. 28, 2020

(54) CHEMOIMMUNOTHERAPY FOR EPITHELIAL CANCER

(71) Applicant: THE REGENTS OF THE UNIVERSITY OF CALIFORNIA, Oakland, CA (US)

(72) Inventors: Michael Karin, La Jolla, CA (US); Shabnam Shalapour, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 131 days.

(21) Appl. No.: 15/558,439

(22) PCT Filed: Mar. 17, 2016

(86) PCT No.: PCT/US2016/022855
§ 371 (c)(1),
(2) Date: Sep. 14, 2017

(87) PCT Pub. No.: WO2016/149485
PCT Pub. Date: Sep. 22, 2016

(65) Prior Publication Data
US 2018/0264004 A1    Sep. 20, 2018

Related U.S. Application Data

(60) Provisional application No. 62/134,258, filed on Mar. 17, 2015.

(51) Int. Cl.
| | |
|---|---|
| A61K 31/555 | (2006.01) |
| A61K 45/06 | (2006.01) |
| A61K 39/395 | (2006.01) |
| A61K 31/675 | (2006.01) |
| A61K 38/05 | (2006.01) |
| A61K 31/136 | (2006.01) |
| C07K 16/28 | (2006.01) |
| A61P 35/04 | (2006.01) |
| A61K 39/00 | (2006.01) |

(52) U.S. Cl.
CPC .......... *A61K 31/555* (2013.01); *A61K 31/136* (2013.01); *A61K 31/675* (2013.01); *A61K 38/05* (2013.01); *A61K 39/39558* (2013.01); *A61K 45/06* (2013.01); *A61P 35/04* (2018.01); *C07K 16/2827* (2013.01); *A61K 2039/505* (2013.01); *A61K 2039/507* (2013.01); *A61K 2300/00* (2013.01); *C07K 2317/76* (2013.01)

(58) Field of Classification Search
CPC .................................................. A61K 31/555
USPC ..................................................... 424/139.1
See application file for complete search history.

(56) References Cited

U.S. PATENT DOCUMENTS

| | | | |
|---|---|---|---|
| 5,057,313 A | 10/1991 | Shih et al. | 424/1.53 |
| 5,475,092 A | 12/1995 | Chari et al. | 530/391.7 |
| 5,585,499 A | 12/1996 | Chari et al. | 548/420 |
| 5,736,137 A | 7/1998 | Anderson et al. | 424/133.1 |
| 5,846,545 A | 12/1998 | Chari et al. | 424/195.11 |
| 5,851,789 A | 12/1998 | Simon | 435/32 |
| 6,238,878 B1 | 5/2001 | Jakobsen | 435/13 |
| 6,333,410 B1 | 12/2001 | Chari et al. | 540/456 |
| 6,340,701 B1 | 1/2002 | Chari et al. | 514/449 |
| 6,372,738 B2 | 4/2002 | Chari et al. | 514/232.5 |
| 6,429,295 B1 | 8/2002 | Carr Perez et al. | 530/387.5 |
| 6,632,979 B2 | 10/2003 | Erickson et al. | 800/18 |
| 6,905,839 B2 | 6/2005 | Furuta | 435/29 |
| 7,202,346 B2 | 4/2007 | Payne et al. | 530/388.1 |
| 7,662,387 B2 | 2/2010 | Law et al. | 424/178.1 |
| 7,666,425 B1 | 2/2010 | Bander | 424/181.1 |
| 2013/0115657 A1 | 5/2013 | Damschroder et al. | 435/69.6 |
| 2014/0271635 A1 | 11/2014 | Brogdon et al. | 424/133.1 |

OTHER PUBLICATIONS

Taberno et al (2013, American Society of Clinical Oncology Meeting, Abstract 3622).*
Carrato et al (Critical Reviews in Oncology/Hematology, 2002, 44: 29-44).*
Shimabukuro-Vornhagen et al (Oncotarget, 2014, 5(13): 6561-6564).*
Beck et al (2011, 6th Annual European Antibody congress 2010, mAbs, 3:2, 111-132).*
Dovedi et al (Cancer Res, 2014, 74(19): 5458-5468).*
Germain et al (Am J Respir Crit Care Med, 2014, 189(7): 832-844).*
Brahmer et al (NEJM, 2012, 366: 2455-2465).*
Raez et al (Clin Lung Can, 2010, 11(1): 18-24).*
Affara, et al., "B Cells Regulate Macrophage Phenotype and Response to Chemotherapy in Squamous Carcinomas." *Cancer Cell*, 25(6):809-821 (2014).
Ammirante, et al., "B-Cell-Derived Lymphotoxin Promotes Castration-Resistant Prostate Cancer." *Nature*, 464(7286):302-305 (2010).
Ammirante, et al., "An IKKalpha-E2F1-BMI1 Cascade Activated by Infiltrating B Cells Controls Prostate Regeneration and Tumor Recurrence." *Genes & Development*, 27(13):1435-1440 (2013).
Ammirante, et al., "Tissue Injury and Hypoxia Promote Malignant Progression of Prostate Cancer by Inducing CXCL13 Expression in Tumor Myofibroblasts." *Proceedings of the National Academy of Sciences of the United States of America*, 111(41):14776-14781 (2014).

(Continued)

*Primary Examiner* — Sean E Aeder
(74) *Attorney, Agent, or Firm* — Medlen & Carroll, LLP

(57) ABSTRACT

The invention provides a method for treating cancer in a subject in need thereof, wherein said subject comprises cancer tissue that 'contains epithelial cancer cells and immunosuppressive 8 cells, and wherein said method comprises administering to said subject a therapeutically effective amount of a) one or more first composition that pauses— immunogenic eel' death and/or of said epithelial cancer cells, and b) one or more second composition that reduces one or both of the number and function of said immunosuppressive B cells in said cancer.

9 Claims, 19 Drawing Sheets

Specification includes a Sequence Listing.

(56) References Cited

OTHER PUBLICATIONS

Arredouani, et al., "Identification of the Transcription Factor Single-Minded Homologue 2 as a Potential Biomarker and Immunotherapy Target in Prostate Cancer." *Clinical Cancer Research*, 15(18):5794-5802 (2009).

Cazac and Roes, "TGF-Beta Receptor Controls B Cell Responsiveness and Induction of IgA in Vivo." *Immunity*, 13(4):443-451 (2000).

Cerutti "The Regulation of IgA Class Switching." *Nature Reviews. Immunology*, 8(6):421-434 (2008).

Chen, et al., "Immunoglobulin Gene Rearrangement in B Cell Deficient Mice Generated by Targeted Deletion of the JH Locus." *International Immunology*, 5(6):647-656 (1993).

Chen and Mellman, "Oncology Meets Immunology: The Cancer-Immunity Cycle." *Immunity*, 39(1):1-10 (2013).

Czeh, et al., "The Immune Response to Sporadic Colorectal Cancer in a Novel Mouse Model." *Oncogene*, 29(50):6591-6602 (2010).

D'Amico, et al., "Biochemical Outcome after Radical Prostatectomy, External Beam Radiation Therapy, or Interstitial Radiation Therapy for Clinically Localized Prostate Cancer." *JAMA*, 280(11):969-974 (1998).

Di Caro, et al., "Occurrence of Tertiary Lymphoid Tissue Is Associated with T-Cell Infiltration and Predicts Better Prognosis in Early-Stage Colorectal Cancers." *Clinical Cancer Research*, 20(8):2147-2158 (2014).

Doi, et al., "IgA Plasma Cells Express the Negative Regulatory Co-Stimulatory Molecule Programmed Cell Death 1 Ligand and Have a Potential Tolerogenic Role in the Intestine." *Biochemical and Biophysical Research Communications*, 425(4):918-923 (2012).

Donkor, et al., "T Cell Surveillance of Oncogene-Induced Prostate Cancer Is Impeded by T Cell-Derived TGF-Beta1 Cytokine." *Immunity*, 35(1):123-134 (2011).

Dummer, et al., "T Cell Homeostatic Proliferation Elicits Effective Antitumor Autoimmunity." *The Journal of Clinical Investigation*, 110(2):185-192 (2002).

Fagarasan, et al., "In Situ Class Switching and Differentiation to IgA-Producing Cells in the Gut Lamina Propria." *Nature*, 413(6856):639-643 (2001).

Feng, et al., "Treg Cell-IgA Axis in Maintenance of Host Immune Homeostasis with Microbiota." *International Immunopharmacology*, 11(5):589-592 (2011).

Forrester, et al., "Effect of Conditional Knockout of the Type II TGF-Beta Receptor Gene in Mammary Epithelia on Mammary Gland Development and Polyomavirus Middle T Antigen Induced Tumor Formation and Metastasis." *Cancer Research*, 65(6):2296-2302 (2005).

Foster, et al., "Characterization of Prostatic Epithelial Cell Lines Derived from Transgenic Adenocarcinoma of the Mouse Prostate (Tramp) Model." *Cancer Research*, 57(16):3325-3330 (1997).

Fremd, et al., "B Cell-Regulated Immune Responses in Tumor Models and Cancer Patients." *Oncoimmunology*/2(7):e25443 (2013).

Gajewski, et al., "Innate and Adaptive Immune Cells in the Tumor Microenvironment." *Nature Immunology*, 14(10):1014-1022 (2013).

Galluzzi, et al., "Immunological Effects of Conventional Chemotherapy and Targeted Anticancer Agents." *Cancer Cell*, 28(6):690-714 (2015).

Garfall, et al., "Chimeric Antigen Receptor T Cells against CD19 for Multiple Myeloma." *New England Journal of Medicine*, 373(11):1040-1047 (2015).

Garg, et al., "Immunogenic Cell Death, Damps and Anticancer Therapeutics: An Emerging Amalgamation." *Biochim Biophys Acta*, 1805(1):53-71 (2010).

Gingrich, et al., "Metastatic Prostate Cancer in a Transgenic Mouse." *Cancer Research*, 56(18):4096-4102 (1996).

Grasso, et al., "The Mutational Landscape of Lethal Castration-Resistant Prostate Cancer." *Nature*, 487(7406):239-243 (2012).

Grivennikov, et al., "Immunity, Inflammation, and Cancer." *Cell*, 140(6):883-899 (2010).

Harriman, et al., "Targeted Deletion of the Iga Constant Region in Mice Leads to IgA Deficiency with Alterations in Expression of Other Ig Isotypes." *Journal of Immunology*, 162(5):2521-2529 (1999).

Herbertz, et al., "Clinical Development of Galunisertib (Ly2157299 Monohydrate), a Small Molecule Inhibitor of Transforming Growth Factor-Beta Signaling Pathway." *Drug Des Devel Ther*, 9:4479-4499 (2015).

Herbst, et al., "Predictive Correlates of Response to the Anti-Pd-L1 Antibody Mpd13280a in Cancer Patients." *Nature*, 515(7528):563-567 (2014).

Hogquist, et al., "T Cell Receptor Antagonist Peptides Induce Positive Selection." *Cell*, 76(1):17-27 (1994).

Holzbeierlein, et al., "Gene Expression Analysis of Human Prostate Carcinoma During Hormonal Therapy Identifies Androgen-Responsive Genes and Mechanisms of Therapy Resistance." *The American Journal of Pathology*, 164(1):217-227 (2004).

Kalos and June "Adoptive T Cell Transfer for Cancer Immunotherapy in the Era of Synthetic Biology." *Immunity*, 39(1):49-60 (2013).

Kang, et al., "Signaling Via LTbetaR on the Lamina Propria Stromal Cells of the Gut Is Required for IgA Production." *Nature Immunology*, 3(6):576-582 (2002).

Kaplan-Lefko, et al., "Pathobiology of Autochthonous Prostate Cancer in a Pre-Clinical Transgenic Mouse Model." *The Prostate*, 55(3):219-237 (2003).

Keren, et al., "B-Cell Depletion Reactivates B Lymphopoiesis in the Bm and Rejuvenates the B Lineage in Aging." *Blood*, 117(11):3104-3112 (2011).

Koh, et al., "Less Mortality but More Relapses in Experimental Allergic Encephalomyelitis in CD8−/− Mice." *Science*, 256(5060):1210-1213 (1992).

Kroemer, et al., "Immunogenic Cell Death in Cancer Therapy." *Annual Review of Immunology*, 31:51-72 (2013).

Krysko, et al., "Immunogenic Cell Death and Damps in Cancer Therapy." *Nature Reviews. Cancer*, 12(12):860-875 (2012).

Lapointe, et al., "Gene Expression Profiling Identifies Clinically Relevant Subtypes of Prostate Cancer." *Proceedings of the National Academy of Sciences of the United States of America*, 101(3):811-816 (2004).

LaTulippe, et al., "Comprehensive Gene Expression Analysis of Prostate Cancer Reveals Distinct Transcriptional Programs Associated with Metastatic Disease." *Cancer Research*, 62(15):4499-4506 (2002).

Lee, et al., "Gemcitabine-Oxaliplatin Plus Prednisolone Is Active in Patients with Castration-Resistant Prostate Cancer for Whom Docetaxel-Based Chemotherapy Failed." *British Journal of Cancer*, 110(10):2472-2478 (2014).

Liu, et al., "Sex-Determining Region Y Box 4 Is a Transforming Oncogene in Human Prostate Cancer Cells." *Cancer Research*, 66(8):4011-4019 (2006).

Ludvigsson, et al., "Association between Iga Deficiency & Other Autoimmune Conditions: A Population-Based Matched Cohort Study." *Journal of Clinical Immunology*, 34(4):444-451 (2014).

Lundy, "Killer B Lymphocytes: The Evidence and the Potential." *Inflammation Research*, 58(7):345-357 (2009).

Luo, et al., "Nuclear Cytokine-Activated IKKalpha Controls Prostate Cancer Metastasis by Repressing Maspin." *Nature*, 446(7136):690-694 (2007).

Magee, et al., "Expression Profiling Reveals Hepsin Overexpression in Prostate Cancer." *Cancer Research*, 61(15):5692-5696 (2001).

Matos, et al., "New Strategies against Prostate Cancer—Pt(II)-Based Chemotherapy." *Current Medicinal Chemistry*, 19(27):4678-4687 (2012).

Michaud, et al., "Autophagy-Dependent Anticancer Immune Responses Induced by Chemotherapeutic Agents in Mice." *Science*, 334(6062):1573-1577 (2011).

Mombaerts, et al., "Rag-1-Deficient Mice Have No Mature B and T Lymphocytes." *Cell*, 68(5):869-877 (1992).

Naddafi and Davami "Anti-CD19 Monoclonal Antibodies: A New Approach to Lymphoma Therapy." *International Journal of Molecular and Cellular Medicine*, 4(3):143-151 (2015).

(56) References Cited

OTHER PUBLICATIONS

Olkhanud, et al., "Tumor-Evoked Regulatory B Cells Promote Breast Cancer Metastasis by Converting Resting CD4(+) T Cells to T-Regulatory Cells." *Cancer Research*, 71(10):3505-3515 (2011).
Pardoll, "The Blockade of Immune Checkpoints in Cancer Immunotherapy." *Nature Reviews. Cancer*, 12(4):252-264 (2012).
Porichis, et al., "High-Throughput Detection of miRNAs and Gene-Specific mRNA at the Single-Cell Level by Flow Cytometry." *Nat Commun*, 5 (2014).
Powles, et al., "MPDL3280A (Anti-PD-L1) Treatment Leads to Clinical Activity in Metastatic Bladder Cancer." *Nature*, 515(7528):558-562 (2014).
Qin, et al., "B Cells Inhibit Induction of T Cell-Dependent Tumor Immunity." *Nature Medicine*, 4(5):627-630 (1998).
Rhodes, et al., "Oncomine: A Cancer Microarray Database and Integrated Data-Mining Platform." *Neoplasia*, 6(1):1-6 (2004).
Ryerson, et al., "Annual Report to the Nation on the Status of Cancer, 1975-2012, Featuring the Increasing Incidence of Liver Cancer." *Cancer*, 122(9):1312-1337 (2016).
Schietinger and Greenberg "Tolerance and Exhaustion: Defining Mechanisms of T Cell Dysfunction." *Trends in Immunology*, 35(2):51-60 (2014).
Schreiber, et al., "Cancer Immunoediting: Integrating Immunity's Roles in Cancer Suppression and Promotion." *Science*, 331(6024):1565-1570 (2011).
Shah "Diagnostic Significance of Levels of Immunoglobulin a in Seminal Fluid of Patients with Prostatic Disease." *Urology*, 8(3):270-272 (1976).
Shalapour, et al., "Immunosuppressive Plasma Cells Impede T-Cell-Dependent Immunogenic Chemotherapy." *Nature*, 521(7550):94-98 (2015).
Sharma, et al., "Novel Cancer Immunotherapy Agents with Survival Benefit: Recent Successes and Next Steps." *Nature Reviews. Cancer*, 11(11):805-812 (2011).
Shen, et al., "Cloning of Ly-5 cDNA." *Proceedings of the National Academy of Sciences of the United States of America*, 82(21):7360-7363 (1985).
Singh, et al., "Gene Expression Correlates of Clinical Prostate Cancer Behavior." *Cancer Cell*, 1(2):203-209 (2002).
Tan, et al., "Tumour-Infiltrating Regulatory T Cells Stimulate Mammary Cancer Metastasis through Rank1-Rank Signalling." *Nature*, 470(7335):548-553 (2011).
Tesniere, et al., "Immunogenic Death of Colon Cancer Cells Treated with Oxaliplatin." *Oncogene*, 29(4):482-491 (2010).
Tomlins, et al., "Integrative Molecular Concept Modeling of Prostate Cancer Progression." *Nature Genetics*, 39(1):41-51 (2007).
Tugues, et al., "New Insights into IL-12-Mediated Tumor Suppression." *Cell Death and Differentiation*, 22(2):237-246 (2015).
Tumeh, et al., "Pd-1 Blockade Induces Responses by Inhibiting Adaptive Immune Resistance." *Nature*, 515(7528):568-571 (2014).
Vanaja, et al., "Transcriptional Silencing of Zinc Finger Protein 185 Identified by Expression Profiling Is Associated with Prostate Cancer Progression." *Cancer Research*, 63(14):3877-3882 (2003).
Varambally, et al., "Integrative Genomic and Proteomic Analysis of Prostate Cancer Reveals Signatures of Metastatic Progression." *Cancer Cell*, 8(5):393-406 (2005).
Wallace, et al., "Tumor Immunobiological Differences in Prostate Cancer between African-American and European-American Men." *Cancer Research*, 68(3):927-936 (2008).
Watson, et al., "Context-Dependent Hormone-Refractory Progression Revealed through Characterization of a Novel Murine Prostate Cancer Cell Line." *Cancer Research*, 65(24):11565-11571 (2005).
Welsh, et al., "Analysis of Gene Expression Identifies Candidate Markers and Pharmacological Targets in Prostate Cancer." *Cancer research*, 61(16):5974-5978 (2001).
Woo, et al., "Tumor Infiltrating B-Cells Are Increased in Prostate Cancer Tissue." *Journal of Translational Medicine*, 12:30 (2014).
Xiao, et al., "Defect in Regulatory B-Cell Function and Development of Systemic Autoimmunity in T-Cell Ig Mucin 1 (Tim-1) Mucin Domain-Mutant Mice." *Proceedings of the National Academy of Sciences of the United States of America*, 109(30):12105-12110 (2012).
Yoshizaki, et al., "Regulatory B Cells Control T-Cell Autoimmunity through IL-21-Dependent Cognate Interactions." *Nature*, 491(7423):264-268 (2012).
Yu, et al., "Gene Expression Alterations in Prostate Cancer Predicting Tumor Aggression and Preceding Development of Malignancy." *Journal of Clinical Oncology : Official Journal of the American Society of Clinical Oncology*/22(14):2790-2799 (2004).
Zhang, et al., "B Lymphocyte Inhibition of Anti-Tumor Response Depends on Expansion of Treg but Is Independent of B-Cell IL-10 Secretion." *Cancer Immunology, Immunotherapy : CII*, 62(1):87-99 (2013).
Zitvogel, et al., "Mechanism of Action of Conventional and Targeted Anticancer Therapies: Reinstating Immunosurveillance." *Immunity*, 39(1):74-88 (2013).
Nowak, et al., "Gemcitabine Exerts a Selective Effect on the Humoral Immune Response: Implications for Combination Chemoimmunotherapy." *Cancer Research*, 62:2353-2358, 2002.
Roche, Investor Science Conference Call From ESMO 2014., Madrid, Sep. 29, 2014.

* cited by examiner

Amino acid sequence of programmed cell death 1 ligand 1 isoform a precursor (PD-L1) Homo sapiens) SEQ ID NO:01-04

A. NCBI Reference Sequence: NP_054862.1 (SEQ ID NO:01)

```
  1 mrifavfifm tywhllnaft vtvpkdlyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipelp lahppnerth
241 lvilgaillc lgvaltfifr lrkgrmmdvk kcgiqdtnsk kqsdthleet
```

B. Entrez Gene: 29126, NCBI Reference Sequence: NC_000009.12 (SEQ ID NO:02)

MRIFAVFIFMTYWHLLNAFTVTVPKDLYVVEYGSNMTIECKFPV
EKQLDLAALIVYWEMEDKNIIQFVHGEEDLKVQHSSYRQRARLLKDQLSLGNAALQIT
DVKLQDAGVYRCMISYGGADYKRITVKVNAPYNKINQRILVVDPVTSEHELTCQAEGY
PKAEVIWTSSDHQVLSGKTTTTNSKREEKLFNVTSTLRINTTTNEIFYCTFRRLDPEE
NHTAELVIPELPLAHPPNERTHLVILGAILLCLGVALTFIFRLRKGRMMDVKKCGIQD
TNSKKQSDTHLEET

C. Entrez Gene: 29126, NCBI Reference Sequence: NC_000009.12 (SEQ ID NO:03)

MRIFAVFIFMTYWHLLNAPYNKINQRILVVDPVTSEHELTCQAE
GYPKAEVIWTSSDHQVLSGKTTTTNSKREEKLFNVTSTLRINTTTNEIFYCTFRRLDP
EENHTAELVIPELPLAHPPNERTHLVILGAILLCLGVALTFIFRLRKGRMMDVKKCGI
QDTNSKKQSDTHLEET

D. Entrez Gene: 29126, NCBI Reference Sequence: NC_000009.12 (SEQ ID NO:04)

MRIFAVFIFMTYWHLLNAFTVTVPKDLYVVEYGSNMTIECKFPV
EKQLDLAALIVYWEMEDKNIIQFVHGEEDLKVQHSSYRQRARLLKDQLSLGNAALQIT
DVKLQDAGVYRCMISYGGADYKRITVKVNAPYNKINQRILVVDPVTSEHELTCQAEGY
PKAEVIWTSSDHQVLSGD

Figure 17

Amino acid sequence of interleukin 10 (IL10) ( Homo sapiens)  NP_00563.1 ; Entrez Gene: 3586 (SEQ ID NO:05):

MHSSALLCCLVLLTGVRASPGQGTQSENSCTHFPGNLPNMLRDL

RDAFSRVKTFFQMKDQLDNLLLKESLLEDFKGYLGCQALSEMIQFYLEEVMPQAENQD

Figure 18

A. IGHA1_HUMAN,P01876, Entrez Gene: 3493, NCBI Reference Sequence: NC_000014.9, containing Ig alpha-1 chain C region, Binding site P01876[352] (SEQ ID NO:06)

ASPTSPKVFP LSLCSTQPDG NVVIACLVQG FFPQEPLSVT WSESGQGVTA
RNFPPSQDAS GDLYTTSSQL TLPATQCLAG KSVTCHVKHY TNPSQDVTVP
CPVPSTPPTP SPSTPPTPSP SCCHPRLSLH RPALEDLLLG SEANLTCTLT
GLRDASGVTF TWTPSSGKSA VQGPPERDLC GCYSVSSVLP GCAEPWNHGK
TFTCTAAYPE SKTPLTATLS KSGNTFRPEV HLLPPPSEEL ALNELVTLTC
LARGFSPKDV LVRWLQGSQE LPREKYLTWA SRQEPSQGTT TFAVTSILRV
AAEDWKKGDT FSCMVGHEAL PLAFTQKTID RLAGKPTHVN VSVVMAEVDG
TCY

B. IGHA2_HUMAN, Entrez Gene: 3494 , P01877, containing Ig alpha-2 chain C region P01877 [1-340], PRO_0000153567 (SEQ ID NO:07)

ASPTSPKVFPLSLDSTPQDGNVVVACLVQGFFPQEPLSVTWSESGQNVTARNFPPSQDAS
GDLYTTSSQLTLPATQCPDGKSVTCHVKHYTNPSQDVTVPCPVPPPPPCCHPRLSLHRPA
LEDLLLGSEANLTCTLTGLRDASGATFTWTPSSGKSAVQGPPERDLCGCYSVSSVLPGCA
QPWNHGETFTCTAAHPELKTPLTANITKSGNTFRPEVHLLPPPSEELALNELVTLTCLAR
GFSPKDVLVRWLQGSQELPREKYLTWASRQEPSQGTTTFAVTSILRVAAEDWKKGDTFSC
MVGHEALPLAFTQKTIDRMAGKPTHVNVSVVMAEVDGTCY

Figure 19

CHEMOIMMUNOTHERAPY FOR EPITHELIAL CANCER

This application claims priority to U.S. provisional Application Ser. No. 62/134,258, filed on Mar. 17, 2015, which is herein incorporated by reference.

GOVERNMENT INTEREST

This invention was made with government support under grant No. R01 CA127923 awarded by National Institutes of Health. The government has certain rights in the invention.

FIELD OF THE INVENTION

The invention relates to methods for treating cancer in a subject in need thereof, wherein said subject comprises cancer tissue that contains epithelial cancer cells and immunosuppressive B cells, and wherein said method comprises administering to said subject a therapeutically effective amount of a) one or more first composition that causes immunogenic cell death and/or of said epithelial cancer cells, and b) one or more second composition that reduces one or both of the number and function of said immunosuppressive B cells in said cancer.

BACKGROUND OF THE INVENTION

Malignant progression and the effectiveness of cancer therapy are strongly modulated by innate and adaptive immunity[4,33]. Whereas myeloid cells and their inflammatory cytokines promote tumorigenesis and confer therapy resistance[21,33], B and T lymphocytes exert both pro- and anti-tumorigenic effects[7,34,35]. Three different strategies can unleash the powerful anti-cancer activity of tumor-infiltrating T (TIL) cells: immune checkpoint inhibitors[36,37], adoptive T cell therapy[38], and, in part, immunogenic chemotherapy[1,4].

Cancer is characterized by multiple genetic alterations and loss of normal cellular regulatory processes. This results in expression of tumor antigens, which can be presented by MHC molecules to activate T cells[1,2]. However, the microenvironment of advanced tumors establishes T cell tolerance, which contributes to malignant progression. Despite significant progress in understanding how T cell tolerance is implemented and maintained[1,3], the critical rate-limiting mechanism operating in each cancer type remains unknown. Cancer-specific T cells must infiltrate and undergo activation within the tumor microenvironment, otherwise they cannot eradicate the malignancy. Indeed, new therapeutics that overcome tolerogenic mechanisms are effective in certain human cancers[1]. Immune mechanisms also affect the outcome of chemotherapy[4]. Importantly, certain chemotherapeutic agents (oxaliplatin, antracyclines) stimulate cancer-specific immune responses by either inducing immunogenic cell death (ICD) or immune effector mechanisms[5,6]. For example, in castrate-resistant prostate cancer (CRPC), B lymphocytes that are recruited by CXCL13 into prostate tumors promote development of CRPC that resists androgen ablation therapy, in a manner dependent on activation of an IKKα-Bmi1 module, needed for survival and proliferation of prostate cancer (PC) progenitor cells, by lymphotoxin (LT) expressing B cell[7,8].

Thus, what is needed are methods for treating tumors and reducing tolerance to cancer chemotherapy, which otherwise contributes to malignant progression.

SUMMARY OF THE INVENTION

The invention provides a method for treating epithelial cancer in a mammalian subject in need thereof, wherein said subject comprises cancer tissue that contains epithelial cancer cells and immunosuppressive B cells, and wherein said method comprises administering to said subject a therapeutically effective amount of (a) one or more first composition that causes immunogenic cell death, and (b) one or more second composition that reduces one or both of the number and function of said immunosuppressive B cells in said cancer. In one embodiment, said first composition that causes immunogenic cell death is selected from the group consisting of oxaliplatin, cyclophosphamide, and mitoxantrone, anthracyclines, and bortezomib. In another embodiment, said first composition that causes immunogenic cell death comprises oxaliplatin. In a further embodiment, said second composition that reduces one or both of the number and function of said immunosuppressive B cells in said cancer comprises an antibody that specifically binds to said immunosuppressive B cells. In yet another embodiment, said second composition that reduces one or both of the number and function of said immunosuppressive B cells in said cancer comprises anti-CD19 antibody and anti-CD20 antibody. In a further embodiment, said second composition that reduces one or both of the number and function of said immunosuppressive B cells in said cancer comprises anti-PDL1 antibody. In another embodiment, said second composition that reduces one or both of the number and function of said immunosuppressive B cells in said cancer comprises anti-CD19-CAR T cells. In another embodiment, said immunosuppressive B cells comprise TGF beta receptors, and wherein said second composition that reduces one or both of the number and function of said immunosuppressive B cells in said cancer is a compound that inhibits binding of said TGF beta receptor to a TGF beta receptor ligand. In a further embodiment, said second composition that inhibits binding of said TGF beta receptor to a TGF beta receptor comprises ALK5 inhibitor. In another embodiment, said epithelial cancer is selected from the group consisting of prostate cancer, liver cancer, bladder cancer, lung cancer, and cutaneous melanoma. In another embodiment, said prostate cancer is selected from the group consisting of castrate-resistant prostate cancer (CRPC), recurrent prostate cancer, and metastatic prostate cancer. In a further embodiment, said epithelial cancer is selected from the group consisting of primary cancer, recurrent cancer, and metastatic cancer. In another embodiment, said administering comprises administering said first composition and said second composition substantially simultaneously. In another embodiment, said administering comprises administering said first composition and said second composition sequentially in any order. In another embodiment, said administering comprises administering said first composition and said second composition substantially simultaneously and sequentially in any order.

The invention also provides a method for reducing prostate cancer in a subject in need thereof comprising,
a) administering to said subject a therapeutically effective amount of an immunogenic chemotherapeutic, and
b) treating said subject with one or more compound that results in one or more of
    i) reducing the number of IgA$^+$ B cells and/or immunosuppressive+B cells in said prostate cancer and/or in other epithelial cancer that contain immunosuppressive B cells, ii) inhibiting the pathways through which the immunosuppressive B cells suppress T cells like PD-L1 and IL-10,
iii) reducing serum IgA, and
iv) reducing binding of TGF beta receptor to one or more TGF beta ligand, wherein said TGF beta receptor is comprised in B cells in said prostate cancer and/or other epithelial cancer.

In one embodiment, said immunogenic chemotherapeutic comprises oxaliplatin. In one embodiment, said prostate cancer is therapy-resistant prostate cancer. In one embodiment, said steps of administering said immunogenic chemotherapeutic and of treating said subject are concomitant. In one embodiment, said steps of administering said immunogenic chemotherapeutic and of treating said subject are not concomitant.

The invention also provides a method of treating prostate cancer in a subject comprising,
a) reducing the number of B cells in said prostate cancer, and
b) administering to said subject a chemotherapeutic.

The invention further provides a method of treating prostate cancer in a subject comprising,
a) treating B cells in said prostate cancer with an antibody; and
b) administering to said subject a chemotherapeutic.

The invention additionally provides a method of treating prostate cancer in a subject comprising,
a) administering a chemotherapeutic to said subject;
b) treating B cells in said prostate cancer with an antibody. In one embodiment, said antibody binds to IgA+ B cells.

BRIEF DESCRIPTION OF THE DRAWINGS

FIG. 10s). The results are summarized in the right panel (n=3 mice per group). g,h, Flow cytometry of PD-1 and Tim-3 expression by CD8$^+$ effector cells (CD8$^+$CD44$^+$ cells) in MC tumors (g) and spleen (Ii) from WT or Jh$^{-/-}$ mice with or without oxaliplatin treatment. Shown are percentages of the corresponding CD8$^+$ T cells in the CD8$^+$CD44$^+$ population (n=3-5 per group). 1, The experimental scheme for B cell immunodepletion in tumor-bearing mice, MC tumors were raised in WT or Cd8a$^{-/-}$ mice, 16 days after s.c. tumor cell inoculation. B cells were depleted by twice weekly administration of antibodies directed against CD19, CD20, CD22 and B220. Four days after first antibody treatment, mice were treated with oxaliplatin (n=4-7 mice per group, total: 44). After 3 weekly chemotherapy cycles, mice were sacrificed. j,k, Flow cytometry analysis of tumor-infiltrating CD45$^+$CD8$^+$ T cells stained for IFNγ (j) or IFNγ and TNF (k) after in vitro restimulation with PMA/ionomycin (n=4-6 mice per group). l-n, Flow cytometry analysis of CD19$^+$ (l,m) and IgA$^+$ (n) cells in spleens and tumors isolated from the WT mice described above, confirming depletion of CD19$^+$ B cells and oxaliplatin-induced IgA$^+$ cells in spleen and tumors. o, Serum IgA concentrations in the mice described in i (n=3-5 per group). p, Flow cytometry analyses of CD19$^+$ B cells in tumors isolated from Cd8a$^{-/-}$ mice subjected to B cell depletion or not, confirmed the efficient depletion of tumoral CD19$^+$ B cells. All results are means±s.e.m. Mann-Whitney and t tests were used to calculate statistical significance indicated by *P, 0.05; P, 0.01; *P, 0.001.

Figure 5:
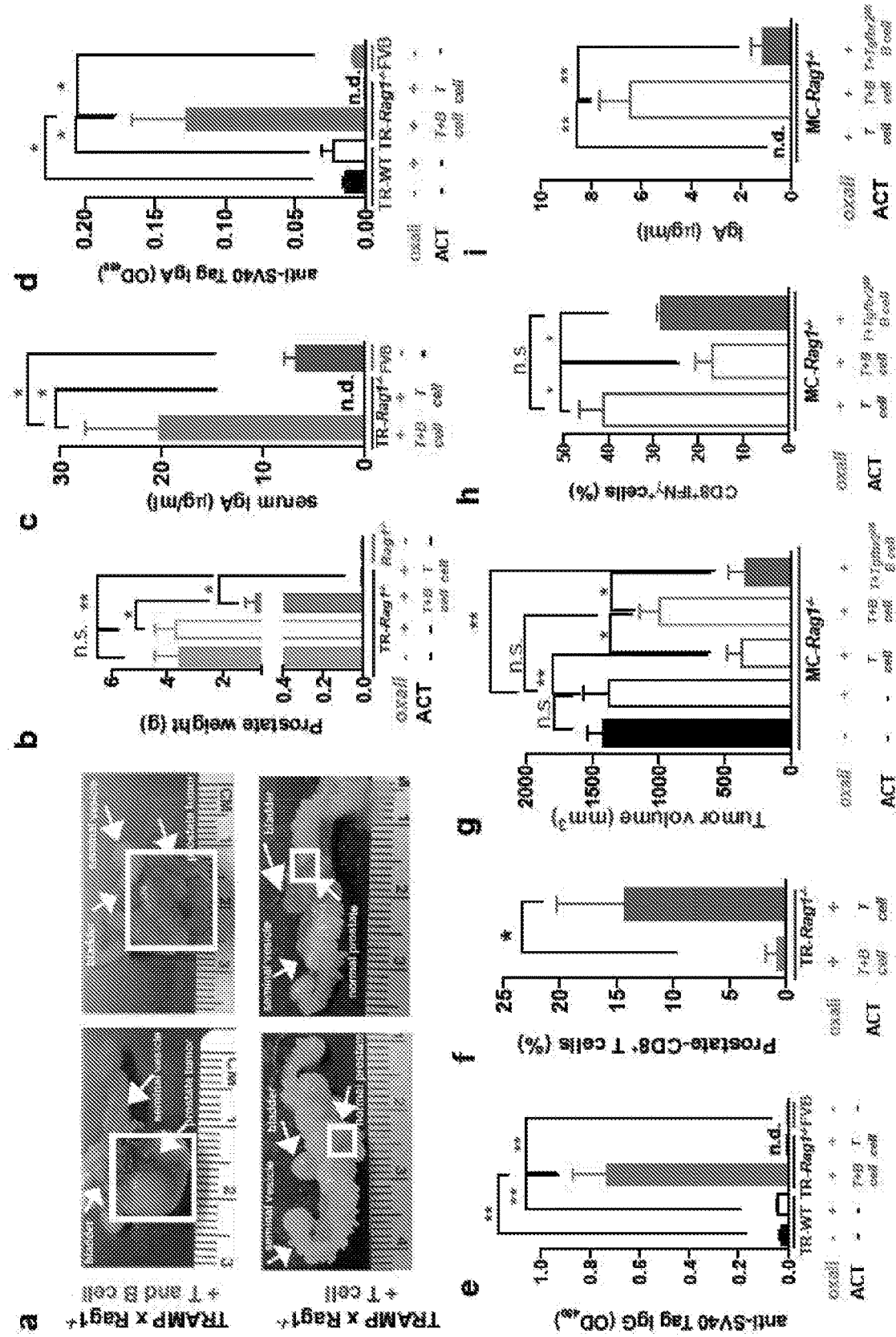
FIG. 5: Adoptively transferred B cells inhibit T cell-dependent tumor eradication, a, Sixteen weeks old TRAMP; Rag1$^{-/-}$ mice received weekly oxaliplatin. One day after 1$^{st}$ treatment, CFSE-labeled splenocytes from WT (B and T cells, SP-WT) or Jh$^{-/-}$ (T but no B cells, SP-Jh$^{-/-}$) mice were adoptively transferred (ACT) into tumor-bearing mice (4-5 per group; 5×10$^6$ T cells per mouse). b, c, After 3 more oxaliplatin cycles, mice were sacrificed, their prostates photographed (b) and tumor weight measured (c). d, Frequency of adoptively transferred CD19$^+$ cells amongst CD45$^+$ cells in spleens and prostates 30 days after ACT. e,f, Serum IgA and IgG in both ACT groups and FVB-WT mice. g,h Serum anti-SV40-Tag IgA and IgG concentrations in indicated mouse strains with or without ACT and/or oxaliplatin treatment. 1, Frequency of CD8$^+$ cells amongst CD45$^+$ cells in TRAMP; Rag1$^{-/-}$ prostates after ACT and oxaliplatin treatment. j, MC tumor-bearing Rag1$^{-/-}$ mice were treated with oxaliplatin. One day later, mice (4-5 per group) received 5×10$^6$ T cells from WT mice immunized with MC cell extract without or with 5×10$^6$ B cells (98% pure) from WT or Tgfbr2$^{AB}$ mice. After 2 more oxaliplatin cycles, mice were sacrificed and tumor volumes determined. k, Flow cytometry of tumoral CD8$^+$ cells in above mice. Cells were re-stimulated for 4 hrs with PMA/ionomycin before analysis. Shown are percentages of IFNγ-expressing cells in total CD8$^+$ cells (n=5-8 per group, small tumors were pooled). l, Serum IgA in above mice. Results are means±s.e.m. Mann-Whitney and t tests were used to determine significance. n.d. not detectable.

inoculated into WT or Tcrβ$^{-/-}$ mice. After 30 days, the mice were divided into 4 groups (n=4-5 each group): 1) control, 2) oxaliplatin (weekly), 3) ATCT, 4) ATCT plus oxaliplatin (weekly). The first oxaliplatin cycle was given at day 31. Two days after the second cycle, CD8$^+$ T cells from CD45.1×CD45.2 WT mice (3×10$^6$ cells) were transferred into tumor-bearing mice and this was followed by two more oxaliplatin cycles after which mice were sacrificed for analysis on day 59. b, Tumor volumes (mm$^3$) c,d, Flow cytometric analysis of spleen (c) and tumor (d) cells after staining with CD45.1, CD45.2, CD8 and TCRαβ antibodies, confirming expansion of adoptively transferred T cells. e, tumor growth curves. f, The experimental scheme. Immunogenic TRAMP-C2 cells were s.c. inoculated into WT or Rag1$^{-/-}$ –×OT-1 mice (no B cells), that harbor CD8$^+$ T cells specific for chicken ovalbumin which is not expressed by TRAMP-C2 cells. After 30 days, tumor-bearing Rag1$^{-/-}$ ×OT-1 mice were divided into 4 groups (n=3-4 mice per group): 1) control, 2) oxaliplatin treatment, 3) ATCT, 4) oxaliplatin treatment plus ATCT. The first oxaliplatin cycle was given at day 31. Two days after the second oxaliplatin cycle, CD8$^+$ T cells (3×10$^6$) from CD45.1×CD45.2 mice were adoptively transferred into tumor-bearing mice, which were sacrificed on day 59 and analyzed. g, Flow cytometric analysis of tumor-infiltrating cells stained with CD45.1, CD45.2, CD8 and TCRαβ antibodies, confirming infiltration of adoptively transferred T cells. h, Flow cytometric analysis of GrzB expression in adoptively transferred, tumor-infiltrating, CD8$^+$ effector cells (CD45.1$^+$CD8$^+$CD44$^+$) from tumor-bearing mice treated as above. i, Tumor volumes (mm). j, tumor growth curves. k-q, Sixteen weeks old TRAMP; Rag1$^{-/-}$ mice (no B and T cells) were treated with oxaliplatin (weekly). One day after the 1$^{st}$ treatment cycle, CFSE-labeled splenocytes from either WT (B and T cells, SP-WT) or Jh$^{-/-}$ (T but no B cells, SP-Jh$^{-/-}$) mice were transferred into the tumor-bearing mice (5×10$^6$ T cells per mouse; 4-5 mice per group). k, l, After 6 days, one mouse from each group was sacrificed, and the proliferation of CD8$^+$ (k) and CD4$^+$ (l) T cells in bone marrow (BM), spleen and prostates was analyzed by CFSE staining and flow cytometry. m-q, After 3 more oxaliplatin cycles (4 weeks in total), the mice were sacrificed and analyzed. m,n, Flow cytometric analyses of CD19$^+$ B lymphocytes for TIM-1 expression in spleens (m) and prostates (n) of above mice. o-q, Flow cytometric analyses of T lymphocytes. Percentages of CD8$^+$ and CD4$^+$ T cells in LN (o); spleens (p); prostates (q) of above TRAMP; Rag1$^{-/-}$ mice. Red: splenocytes from WT mice (T and B cell transfer), blue: splenocytes from Jh$^{-/-}$ mice (T cell transfer). r, The experimental scheme for FIG. 5$j$. MC tumor-bearing Rag1$^{-/-}$ mice (no B and T cells) were treated with oxaliplatin (weekly). One day after 1$^{st}$ oxaliplatin treatment, 5×10$^6$ T cells (negative selection) from WT mice immunized with MC cell lysate[10] were adoptively transferred into tumor-bearing mice (4-5 mice per group), alone or in combination with 5×10$^6$ B cells from WT or Tgfbr2$^{ΔB}$ mice (purity 98%). After 2 more oxaliplatin cycles (3 weeks total), the mice were sacrificed and analyzed. s, Serum IgG analysis of above mice. t, Flow cytometric analysis of splenocytes after staining with CD45 and CD19 antibodies. All results are means±s.e.m. Mann-Whitney and t tests were used to calculate statistical significance. Statistical significance is given by *P, 0.05; P, 0.01; *P, 0.001.

Figure 15:
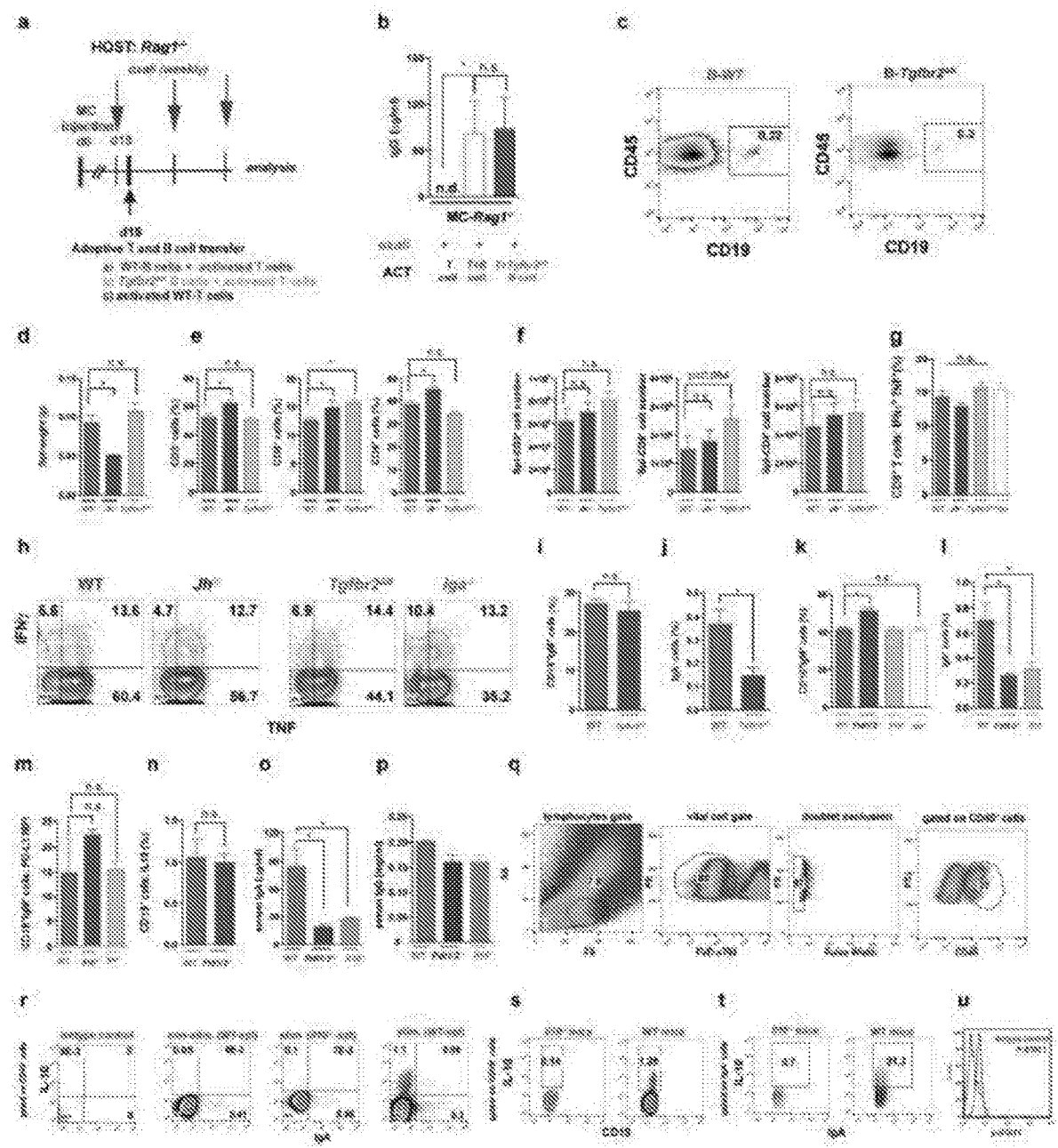

FIG. 15: Analysis of lymphocytes and monocytes in tumor-free mice, gating strategies and staining controls. WT, Jh$^{-/-}$, Iga$^{-/-}$ and Tgfbr2$^{ΔB}$ mice in the FVB background and WT, Pdl1/2$^{-/-}$, Il10$^{-/-}$ and Iga$^{-/-}$ in the C57BL/6 background were analyzed for the distribution of immune markers. a, Spleen weights of WT, Jh$^{-/-}$ and Tgfbr2$^{ΔB}$ mice in the FVB background. b, Flow cytometry of splenocytes for the following markers: CD3 (left), CD8 (middle), CD4 (right), gated on the splenic CD45$^+$ population. c, Absolute cell numbers of splenic CD3$^+$ (left), CD8$^+$ (middle), and CD4$^+$ (right) cells are shown (percentage×cell count of whole spleen). d,e Flow cytometry for TNF and IFNγ in CD8$^+$ cells from tumor-free WT, Jh$^{-/-}$, Tgfbr2$^{ΔB}$ and Iga$^{-/-}$ mice (n=6-8) that were re-stimulated in vitro with PMA/ionomycin and the representative flow cytometry panels (e). f,g, Flow cytometry of splenocytes from WT and Tgfbr2$^{ΔB}$ for: CD19$^+$ IgM$^+$ cells (f) and IgA (g) gated on the splenic CD45$^+$ population. h-m, Flow cytometry of splenocytes from WT, Pdl1/2$^{-/-}$ and Il10$^{-/-}$ mice for: CD45$^+$CD19$^+$IgM$^+$ cells (h), CD45$^+$IgA$^+$ cells (i), PD-L1 expression by CD19$^+$IgM$^+$ cells (j), and IL-10 expression by CD19$^+$ cells (k). l,m, Serum IgA and IgG concentrations were analyzed in WT, Pdl1/2$^{-/-}$ and Il10$^{-/-}$ mice (n=4-5 mice per group). All results are means±s.e.m. Mann-Whitney and t tests were used to calculate statistical significance shown as *P, 0.05; P, 0.01; *P 0.001. The different gating strategies and staining controls are shown. n, Gating strategies for analysis of splenocytes: lymphocyte gate, dead cell exclusion, doublets exclusion, and gating on the CD45$^+$ population. o, Gating strategies for tumor-infiltrating lymphocytes: lymphocyte gate, dead cell exclusion, doublets exclusion, and gating on the CD45$^+$ population. p, Flow cytometric analysis of IL-10 and IgA expression, gated on the CD45$^+$ population: 1) isotype control (no staining), 2) non-stimulated splenocytes: showing IgA staining, but not IL-10. 3) stimulated splenocytes from Il10$^{-/-}$ mice showing IgA staining, but not IL-10. 4) stimulated splenocytes from WT mice showing IgA and IL-10 staining. q, Flow cytometric analysis of IL-10 and CD19 expression, gated on the CD19$^+$B220$^+$ population. left: stimulated cells from Il10$^{-/-}$ mice, showing B cell staining, but not IL-10; right: stimulated cells from WT mice showing B cell staining and IL-10 staining. r, Flow cytometric analysis of IL-10 and IgA expression, gated on the IgA$^+$ population: left: stimulated cells from Il10$^{-/-}$ mice, showing IgA cell staining, but not IL-10; right: stimulated cells from WT mice showing IgA and IL-10 staining. These results confirm IL-10 production by IgA$^+$ cells. s, Flow cytometric analysis of p-STAT1 staining with corresponding isotype control.

Figure 16:
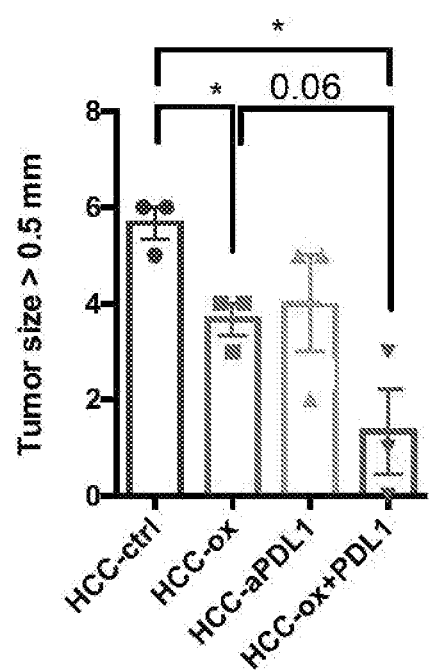

FIG. 16: Anti-PD-L1 treatment induce hepatocellular carcinoma tumor regression only when combined with oxaliplatin. WT mice bearing Hepatocellular carcinoma tumors (DEN-treated) were divided into four treatment groups. 1) isotype control (IgG2a); 2) oxaliplatin (weekly), 3) anti-PD-L1 (weekly); 4) oxaliplatin and anti-PD-L1 (weekly). After 4 treatment cycles, mice were sacrificed and analyzed. Tumor size are shown. Significance was determined by t tests.

FIG. 17: Amino acid sequence of programmed cell death 1 ligand 1 isoform a precursor (PD-L1) *Homo sapiens*) A. NCBI Reference Sequence: NP_054862.1 (SEQ ID NO:01), B. Entrez Gene: 29126, NCBI Reference Sequence: NC_000009.12 (SEQ ID NO:02), C. Entrez Gene: 29126, NCBI Reference Sequence: NC_000009.12 (SEQ ID NO:03), and D. Entrez Gene: 29126, NCBI Reference Sequence: NC_000009.12 (SEQ ID NO:04).

FIG. 18: Amino acid sequence of interleukin 10 (IL10) (*Homo sapiens*) NP 00563.1; Entrez Gene: 3586 (SEQ ID NO:05).

FIG. 19: Amino acid sequence of portions of immunoglobulin A (IgA). A. IGHA1_HUMAN, P01876, Entrez Gene: 3493, NCBI Reference Sequence: NC_000014.9, containing Ig alpha-1 chain C region, Binding site P01876 [352] (SEQ ID NO:06). B. IGHA2_HUMAN, Entrez Gene: 3494, P01877, containing Ig alpha-2 chain C region P01877 [1-340], PRO_0000153567 (SEQ ID NO:07).

DEFINITIONS

To facilitate understanding of the invention, a number of terms are defined below.

"Oxaliplatin" is a non-mycloablative or lymphodepleting chemotherapy drug. Exemplary dosage include 30-65 mg/m$^2$ weekly or every two weeks, and may be adjusted to minimize lymphocyte and/or T cell number depletion. In one embodiment, the number of white blood cells is calculated weekly using, for example, a hemocytometer or flow cytometer. The dosage is decreased if the lymphocyte, and more particularly T cell, number decreases.

"TGF beta receptor ligand" is a molecule that binds to the TGF beta receptor, and is exemplified by Bone morphogenetic proteins (BMPs), Growth and differentiation factors (GDFs), Anti-müllerian hormone (AMH), Activin, Nodal, and TGFβ's.

"Treating" disease (e.g., cancer) refers to delaying, reducing, palliating, ameliorating, stabilizing, preventing and/or reversing one or more symptoms (such as objective, subjective, pathological, clinical, sub-clinical, etc.) of the disease. Objective symptoms are exemplified by tumor size (e.g. dimensions, weight and/or volume), tumor number, rate of change in tumor size and/or number, presence of metastasis, metastasis size (e.g. dimensions, weight and/or volume), metastasis number, and/or rate of change in metastasis size and/or number. Subjective symptoms are exemplified by pain, fatigue. etc. Cancer symptoms may be assessed by, for example, biopsy and histology, and blood tests to determine relevant enzyme levels or circulating antigen or antibody, and imaging tests which can be used to detect a decrease in the growth rate or size of a neoplasm.

The terms "therapeutic amount," "pharmaceutically effective amount," and "therapeutically effective amount," are used interchangeably herein to refer to an amount that is sufficient to achieve a desired result, such as treating disease.

"Cancer cell" refers to a cell undergoing early, intermediate or advanced stages of multi-step neoplastic progression as previously described (Pitot et al., Fundamentals of Oncology, 15-28 (1978)). This includes cells in early, intermediate and advanced stages of neoplastic progression including "pre-neoplastic cells (i.e., "hyperplastic cells and dysplastic cells), and neoplastic cells in advanced stages of neoplastic progression of a dysplastic cell.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

"Cancer" refers to a plurality of cancer cells that may or may not be metastatic, such as prostate cancer, liver cancer, bladder cancer, skin cancer (e.g., cutaneous, melanoma, basal cell carcinoma, Kaposi's sarcoma, etc.), ovarian cancer, breast cancer, lung cancer, cervical cancer, pancreatic cancer, colon cancer, stomach cancer, esophagus cancer, mouth cancer, tongue cancer, gum cancer, muscle cancer, heart cancer, bronchial cancer, testis cancer, kidney cancer, endometrium cancer, and uterus cancer. Cancer may be a primary cancer, recurrent cancer, and/or metastatic cancer. The place where a cancer starts in the body is called the "primary cancer" or "primary site." If cancer cells spread to another part of the body the new area of cancer is called a "secondary cancer" or a "metastasis." "Recurrent cancer" means the presence of cancer after treatment and after a period of time during which the cancer cannot be detected. The same cancer may be detected at the primary site or somewhere else in the body, e.g., as a metastasis.

"Epithelial cancer" refers to cancer that starts in epithelial tissues. Epithelial tissue covers the outside of the body as the skin, covers and lines all the organs inside the body, such as the organs of the digestive system, and lines the body cavities, such as the inside of the chest cavity and the abdominal cavity.

The term "specifically binds" and "specific binding" when made in reference to the binding of antibody to a target molecule (e.g., peptide) or to a target cell (e.g., immunosuppressive B cells), refer to an interaction of the antibody with one or more epitopes on the target molecule or target cell where the interaction is dependent upon the presence of a particular structure on the target molecule or target cell. For example, if an antibody is specific for epitope "A" on the target cell, then the presence of a protein containing epitope A (or free, unlabeled A) in a reaction containing labeled "A" and the antibody will reduce the amount of labeled A bound to the antibody. In one embodiment, the level of binding of an antibody to a target molecule or target cell is determined using the "IC50" i.e., "half maximal inhibitory concentration" that refer to the concentration of a substance (e.g., inhibitor, antagonist, etc.) that produces a 50% inhibition of a given biological process, or a component of a process (e.g., an enzyme, antibody, cell, cell receptor, microorganism, etc.). It is commonly used as a measure of an antagonist substance's potency.

"Mammalian subject" includes human, non-human primate, murine (e.g., mouse, rat, guinea pig, hamster), ovine, bovine, ruminant, lagomorph, porcine, caprine, equine, canine, feline, ave, etc.).

A subject "in need" of treatment with the invention's methods includes a subject that is "suffering from disease," i.e., a subject that is experiencing and/or exhibiting one or more symptoms of the disease, and subject "at risk" of the disease. A subject "in need" of treatment includes animal models of the disease. Subject "at risk" of disease refers to a subject that is not currently exhibiting disease symptoms and is predisposed to expressing one or more symptoms of the disease. This predisposition may be genetic based on family history, genetic factors, environmental factors such as exposure to detrimental compounds present in the environment, etc.). It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

"Immunosuppressive B cells," "immunosuppressive plasmocyte cells," "immunosuppressive plasma cells," interchangeably refer to B lymphocyte cells that impede T-cell-dependent immunogenic chemotherapy (see examples 2-6) and are characterized by expressing PD-L1 (exemplified in FIG. 17) and Interleukin-10 (exemplified in FIG. 18) (IL10$^+$ PD-L1$^+$). In some embodiments, immunosuppressive B cells further express immunoglobulin A (IgA$^+$ IL10$^+$ PD-L1$^+$) (FIG. 19). In one embodiment, immunosuppressive B cells are distinct from the LT-producing CD20$^+$ B cells.

"Immunogenic cell death" ("ICD") is a form of cell death caused by some cytostatic agents such as oxaliplatin, cyclophosphamide, and mitoxantrone (Galluzzi et al., Cancer Cell. 2015 Dec. 14; 28(6):690-714) and anthracyclines, bortezomib, radiotherapy and photodynamic therapy (PDT) (Garg et al. (2010) "Immunogenic cell death, DAMPs and anticancer therapeutics: an emerging amalgamation.". Biochim Biophys Acta 1805 (1): 53-71). Unlike normal apoptosis, which is mostly nonimmunogenic or even tolerogenic, immunogenic apoptosis of cancer cells can induce an effective antitumour immune response through activation of dendritic cells (DCs) and consequent activation of specific T cell response. ICD is characterized by secretion of damage-associated molecular patterns (DAMPs).

The terms "programmed cell death 1 ligand 1 isoform a precursor" and PD-L1" (also known as CD274; B7-H; B7H1; PDL1; PD-L1; PDCD1L1; PDCD1LG1) refer to the immune inhibitory receptor ligand that is expressed by hematopoietic and non-hematopoietic cells, such as T cells and B cells and various types of tumor cells. The encoded protein is a type 1 transmembrane protein that has immunoglobulin V-like and C-like domains. Interaction of this ligand with its receptor inhibits T-cell activation and cytokine production. During infection or inflammation of normal tissue, this interaction is important for preventing autoimmunity by maintaining homeostasis of the immune response. In tumor microenvironments, this interaction provides an immune escape for tumor cells through cytotoxic T-cell inactivation. Expression of this gene in tumor cells is considered to be prognostic in many types of human malignancies, including colon cancer and renal cell carcinoma. Alternative splicing results in multiple transcript variants. Human PD-L1 amino acid sequence is exemplified by SEQ ID NO:01-04 (FIG. 17).

The terms "interleukin 10" and "IL-10" (also known as CSIF; TGIF; GVHDS; IL10A) refer to a cytokine produced primarily by monocytes and to a lesser extent by lymphocytes. This cytokine has pleiotropic effects in immunoregulation and inflammation. It down-regulates the expression of Th1 cytokines, MHC class II Ags, and costimulatory molecules on macrophages. It also enhances B cell survival, proliferation, and antibody production. Human interleukin 10 amino acid sequence is exemplified by SEQ ID NO:05 (FIG. 18).

The terms "immunoglobulin A," "IgA," and "Ig alpha" refer to the major immunoglobulin class in body secretions. It may serve both to defend against local infection and to prevent access of foreign antigens to the general immunologic system. Portions of human IgA amino acid sequences are exemplified by SEQ ID NO:06-07 (FIG. 19).

The terms "reduce," "inhibit," "diminish," "suppress," "decrease," and grammatical equivalents when in reference to the level of any molecule (e.g., amino acid sequence, and nucleic acid sequence, antibody, etc.), cell (e.g., B cell, T cell, tumor cell), and/or phenomenon (e.g., disease symptom), in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis.

The terms "increase," "elevate," "raise," and grammatical equivalents (including "higher," "greater," etc.) when in reference to the level of any molecule (e.g., amino acid sequence, and nucleic acid sequence, antibody, etc.), cell (e.g., B cell, T cell, tumor cell) and/or phenomenon (e.g., disease symptom), in a first sample (or in a first subject) relative to a second sample (or relative to a second subject), mean that the quantity of the molecule, cell and/or phenom- enon in the first sample (or in the first subject) is higher than in the second sample (or in the second subject) by any amount that is statistically significant using any art-accepted statistical method of analysis.

DESCRIPTION OF THE INVENTION

The invention provides a method for treating cancer in a subject in need thereof, wherein said subject comprises cancer tissue that contains epithelial cancer cells and immunosuppressive B cells, and wherein said method comprises administering to said subject a therapeutically effective amount of a) one or more first composition that causes immunogenic cell death and/or of said epithelial cancer cells, and b) one or more second composition that reduces one or both of the number and function of said immunosuppressive B cells in said cancer.

Data herein show that successful eradication of large tumors in prostate (Examples 1-7) and liver (Example 8) by immunogenic chemotherapy requires removal of immunosuppressive plasmocytes that are present both in mouse and human PC. Three different, spontaneous and transplantable, mouse models of PC contain IgA$^+$ plasmocytes that strongly suppress activation of CD8$^+$ TIL after treatment of tumor-bearing mice with oxaliplatin. Unlike cisplatin, oxaliplatin induces immunogenic cell death that augments CTL activation and consequent tumor eradication[5,28]. Although oxaliplatin causes regression of small tumors (<100 mm$^3$), it does not induce CTL activation and eradication of large (>400 mm$^3$) prostate tumors, despite induction of a DNA damage response. The main impediment to successful eradication of large tumors are tumor-infiltrating immunosuppressive B cells, that express IgA and CD138 but have down-regulated CD20 expression and therefore exhibit a typical plasmocyte phenotype. Nearly all of these cells express PD-L1 and about half of them also express IL-10 and Fas-L. Importantly, genetic analysis confirms that much of the immunosuppressive activity is derived from IgA$^+$PD-L1$^+$IL-10$^+$ cells. Development of these cells, which are distinct from the LT-producing CD20$^+$ B cells that infiltrate androgen-deprived prostate tumors and stimulate CRPC emergence through the IKKα-Bmi1 module[7,8], depends on TGFβR signaling. Nonetheless, the IgA$^+$ plasmocytes may have evolved from CD20+LT$^+$ B cells upon encounter of high TGFβ concentrations and antigen in the PC microenvironment after oxaliplatin treatment. Ablation of T cell TGFβ1 was reported to augment CTL activation and inhibit tumor growth in TRAMP mice[39], and some of the IgA$^+$ plasmocytes in human PC are located next to T cells. Another important TGFβ source are the αSMA$^+$ myofibroblasts that also reside next to IgA$^+$ cells in oxaliplatin-treated mouse tumors and human PC samples[16]. Alternatively, LT-producing B cells may also stimulate the IgA CSR, as signaling via LTβ receptor on gut lamina propria stromal cells is required for IgA production[40]. Although the anti-inflammatory activity of intestinal IgA-producing cells is well known[41], this is the first time IgA$^+$ plasmocytes were found to suppress anti-tumor immunity.

As long as numerous IgA$^+$ plasmocytes are present within prostate tumors, oxaliplatin fails to evoke a productive CTL-dependent anti-tumor response. Instead, CD8$^+$ TIL express markers of exhaustion, including PD-1, TIM-3 and BTLA[3]. Suppression of the anti-tumor CTL response by IgA plasma cells requires PD-L1 and IL-10, both of which can induce anergy or exhaustion[3,37]. Suppression may also involve Fas-L which can kill activated TILs[42]. B cell-mediated immunosuppression is also seen in adoptive transfer experiments, where B cells block the ability of transferred T cells to fully eradicate large prostate tumors in oxaliplatin-treated TRAMP mice or in mice bearing TRAMP-C2 or MC tumors. Immunosuppression requires TGFβR2 expression on B cells, suggesting it is mediated by IgA+ plasmocytes. Yet, other mechanisms by which B cells regulate anti-tumor immunity were previously proposed[43,44], including indirect control of T cell infiltration via macrophages[21] and IL-10 production by Breg cells[45]. However, Breg-mediated suppression was only found to affect CD4+ T helper cells[43,44,46]. Notably, IL-10-expressing IgA+ cells are most abundant in therapy-resistant and metastatic human PC and circulating IgA is a well-established adverse prognostic indicator in PC[47].

Data herein demonstrate that elimination or inhibition of tumor infiltrating IgA+plasmocytes is important to successful immunotherapy of cancer (such as PC, liver cancer, etc.) as long as an immunogenic chemotherapeutic, such as oxaliplatin, is also used. Data herein also show that immunogenic chemotherapy enhances response rates to PD-1 or PD-L1 blockade in other malignancies, including bladder cancer and cutaneous melanoma where up to 35% of the patients were found to be responsive[48-50].

The invention's methods use a first composition that induces immunogenic cell death (ICD), and that is referred to as "immunogenic chemotherapeutic compound" or "chemoimmunotherapeutic compound." This first composition is exemplified by oxaliplatin, cyclophosphamide, and mitoxantrone (Galluzzi et al., Cancer Cell. 2015 Dec. 14; 28(6):690-714) and anthracyclines, bortezomib, radiotherapy and photodynamic therapy (PDT) (Garg et al. (2010) "Immunogenic cell death, DAMPs and anticancer therapeutics: an emerging amalgamation.". Biochim Biophys Acta 1805 (1): 53-71). doi:10.1016/j.bbcan.2009.08.003. PMID 19720113)

In one preferred embodiment, the compound that causes immunogenic cell death comprises oxaliplatin.

The invention's methods use a second composition, in combination with the above-described first composition, wherein the second composition reduces one or both of the number and function of the immunosuppressive plasmocyte cells in the cancer that is being treated. In one embodiment, the second composition that reduces one or both of the number and function of the immunosuppressive plasmocyte cells comprises antibody that specifically binds to said immunosuppressive B cells. This is illustrated by the use of a combination of anti-CD19 antibody (Int J Mol Cell Med. 2015 Summer; 4(3):143-51 Anti-CD19 Monoclonal Antibodies: a New Approach to Lymphoma Therapy. Naddafi F, Davami) and anti-CD20 antibody (rituximab). Exemplary antibody dosage is 375 mg/m² intravenous infusion on day 1 of the first of 4 to 5 cycles.

In one embodiment, the second composition that reduces one or both of the number and function of the immunosuppressive plasmocyte cells comprises anti-PDL1 antibody (also referred to as "anti-PD-L1 antibody" and "aPDL1"). Exemplary anti-PDL1 antibodies that reduce the function, development, and/or number of PD-L1), are commercially available (Genentech) and are in clinical trials (See, A Phase I Study of Atezolizumab (an Engineered Anti-PDL1 Antibody) in Patients with Locally Advanced or Metastatic Solid Tumors. ClinicalTrials.gov Identifier: NCT01375842).

In one embodiment, the second composition that reduces one or both of the number and function of the immunosuppressive plasmocyte cells comprises "anti-CD19-CAR T cells," which are chimeric Antigen Receptor T Cells against CD19 for Multiple Myeloma, described in Garfall et al., N Engl J Med. 2015 Sep. 10; 373(11): 1040-7.

In one embodiment, the immunosuppressive B cells comprise TGF beta receptors, and the second composition that reduces one or both of the number and function of said immunosuppressive plasmocyte cells in the cancer being treated is a compound that inhibits binding of said TGF beta receptor to a TGF beta receptor ligand, and is exemplified by the small molecule "ALK5 inhibitor," which is in clinical trials (Herbertz et al., Drug Des Devel Ther. 2015 Aug. 10; 9:4479-99. doi: 10.2147/DDDT.S86621. eCollection 2015).

The term "administering" to a subject means delivering a molecule to a subject. "Administering" a composition to a subject in need of reducing a disease and/or of reducing one or more disease symptoms includes prophylactic administration of the composition (i.e., before the disease and/or one or more symptoms of the disease are detectable) and/or therapeutic administration of the composition (i.e., after the disease and/or one or more symptoms of the disease are detectable). The invention's methods include administering a combination of a first composition that causes immunogenic cell death, and a second composition that reduces one or both of the number and function of immunosuppressive plasmocyte cells. The first and second compositions may be administered simultaneously at substantially the same time, and/or administered sequentially at different times in any order (first composition followed second composition, or second composition followed by first composition). For example, administering said second composition substantially simultaneously and sequentially in any order includes, for example, (a) administering the first and second compositions simultaneously at substantially the same time, followed by administering the first composition then the second composition at different times, (b) administering the first and second compositions simultaneously at substantially the same time, followed by administering the second composition then the first composition at different times, (c) administering the first composition then the second composition at different times, followed by administering the first and second compositions simultaneously at substantially the same time, and (d) administering the second composition then the first composition at different times, followed by administering the first and second compositions simultaneously at substantially the same time.

Administering may be done using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789). The invention's compositions may be administered prophylactically (i.e., before the observation of disease symptoms) and/or therapeutically (i.e., after the observation of disease symptoms). Administration also may be concomitant with (i.e., at the same time as, or during) manifestation of one or more disease symptoms. Also, the invention's compositions may be administered before, concomitantly with, and/or after administration of another type of drug or therapeutic procedure (e.g., surgery).

Methods of administering the invention's compositions include, without limitation, administration in parenteral, oral, intraperitoneal, intranasal, topical and sublingual forms. Parenteral routes of administration include, for example, subcutaneous, intravenous, intramuscular, intrasternal injection, and infusion routes. In a preferred embodiment, administration in intraperitoneal and/or intravenous.

Antibody treatment of human beings with cancer is known in the art, for example in U.S. Pat. Nos. 5,736,137; 6,333,410; 5,475,092; 5,585,499; 5,846,545; 7,202,346;

6,340,701; 6,372,738; 7,202,346; 5,846,545; 5,585,499; 5,475,092; 7,202,346; 7,662,387; 7,662,387; 6,429,295; 7,666,425; 5,057,313.

The invention's antibodies may be administered with pharmaceutically acceptable carriers, diluents, and/or excipients. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

A) Prostate Cancer

Cancer development and response to therapy are strongly influenced by innate and adaptive immunity. For example, androgen depiction and malignant progression affect recruitment of lymphocytes into prostate tumors, including B cells that produce lymphotoxin and thereby stimulate expansion of androgen-deprived prostate cancer (PC) progenitors. Normally prostate cancer does not respond to an immunogenic (low) dose of oxaliplatin. The invention's methods sensitize prostate cancer to low-dose oxaliplatin and achieve nearly complete tumor elimination through activation of cytotoxic T cells. The invention's method is based on removal or inactivation of immunosuppressive B cells that accumulate in prostate tumors and prevent the activation of cytotoxic T cells.

Aggressive prostate cancer is refractory to chemotherapy and so far attempts to treat prostate cancer with immune checkpoint inhibitors have failed. Data herein (Examples 1-7) show that prostate cancer does not respond to low immunosuppressive doses of oxaliplatin, a chemotherapeutic drug. due to accumulation of immunosuppressive B cells that prevent the activation of cytotoxic T cells. By getting rid of those B cells we were able to fully sensitize prostate tumors to low doses of oxaliplatin and achieve nearly complete tumor elimination. Immunosuppressive B cells are present in both mouse and human prostate cancer.

Data herein (Examples 1-7) show that B cells also determine how PC responds to the immunogenic chemotherapeutic agent oxaliplatin, which at a low, non-myelosuppressive, dose induces immunogenic cell death that can promote activation of tumor-directed cytotoxic T cells (CTL). However, three different mouse models of PC do not respond to oxaliplatin unless genetically or pharmacologically depleted of B cells. The B lymphocytes found to suppress CTL activation are plasmocytes that express IgA, IL-10 and PD-L1, whose appearance depends on TGFβ-receptor (TGFβR) signaling. Elimination of these cells, which also infiltrate human therapy-resistant PC, allows CTL-dependent eradication of oxaliplatin-treated tumors.

Currently, there are immune checkpoint therapies based on inhibition of CTLA4, PD-1 or PD-L1. Also, there are B cell targeting drugs such as Rituxan. However, immunosuppressive B cells are completely refractory to these drugs.

Data herein (Examples 1-7) confirmed the efficacy of the invention's method in two mouse models of prostate cancer, and also confirmed the presence of immunosuppressive B cells in human prostate cancer. Since CRPC is refractory to most therapies[9,10], data herein in Examples 1-7 examined the role of B cells in acquisition of chemotherapy resistance. We focused our studies on oxaliplatin, an immunogenic chemotherapeutic drug[4,5] that is effective in aggressive PC[9,10].

B) Liver Cancer:

Example 8 shows that immunosuppressive B cells are present in hepatocellular carcinoma tumors, and the combination therapy of oxaliplatin with checkpoint inhibitor (aPDL1) decreased the number of liver tumors.

EXPERIMENTAL

The following serve to illustrate certain preferred embodiments and aspects of the present invention and are not to be construed as limiting the scope thereof. See Shalapour et al., Nature (2015) 521(7550):94-8. doi: 10.1038/nature 14395.

Example 1: Materials and Methods

All TRAMP mice, their derivatives and s.c. Myc-Cap transplantation were in the FVB genetic background and their basic immune parameters are shown in FIG. 15a-m. For s.c. TRAMP-C2 tumors, C57BL/6 mice were used. In both s.c. tumors, $2-3 \times 10^6$ cells/mouse were transplanted. More detailed information is as follows.

Animal Models

C57BL/6 and FVB control mice were purchased from Charles River Laboratories and CD45.1 mice[1] were purchased from Jackson Laboratory, and all were bred at the University of California San Diego (UCSD) animal facility. C57BL/6-Tg(TRAMP)8247Ng/J (TRAMP mice)[2] were backcrossed to the FVB strain for more than 10 generations. The median survival of TRAMP-FVB mice was 23 weeks compared to 52 weeks for TRAMP-C57BL/6 mice. TRAMP mice were crossed with B cell-deficient ($Jh^{-/-}$) mice[3], CTL-deficient ($Cd8a^{-/-}$) mice[4] or $Rag1^{-/-}$ mice, which lack both B and T cells[5], all in the FVB-background. OT-I mice were obtained from Taconic[6]. $Tgfbr2^{F/F}$ (FVB-background) mice were obtained from Dr. Hal Moses at Vanderbilt University[7]. $Tcrb^{-/-}$, Cd19-Cre, $Il10^{-/-}$ and CD45.1 mice were purchased from the Jackson Laboratory. IgA gene-deficient ($Iga^{-/-}$) mice[8] were obtained from Baylor College of Medicine. $Pdl1/2^{-/-}$ mice were obtained from Genentech (San Francisco, Calif.). Cd19-Cre and $Iga^{-/-}$ mice were backcrossed to the FVB strain for more than 10 generations. All mice were maintained in filter-topped cages on autoclaved food and water at the UCSD animal facility and all experiments were performed in accordance with UCSD and NIH guidelines and regulations. The number of mice used in each experiment and the number of experiments are shown in Table 1 below.

TABLE 1

| Experimental genotype | control | oxali (cispl) | number of experiments |
|---|---|---|---|
| MC-WT | 22 | 24 (+6 cispl) | 6 |
| TR-WT | 32 | 21 | 6 |
| MC-$Jh^{-/-}$ | 18 | 14 (+4 cispl) | 4 |
| TR-$Jh^{-/-}$ | 19 | 18 | 4 |
| MC-$Cd8a^{-/-}$ | 10 | 11 | 2 |
| TR-$Cd8a^{-/-}$ | 19 | 18 | 3 |
| MC-$Rag^{-/-}$ | 9 | 10 | 2 |
| TR-$Rag^{-/-}$ | 9 | 9 | 2 |
| MC-$Tgfbr2^{AB}$ | 7 | 9 | 3 |
| MC-$Iga^{-/-}$ | 8 | 9 | 3 |
| MC-$Jh^{-/-}$+ B cell transfer | — | 14 | 2 |
| MC-WT+ aPD-L1 | 10 | 10 | 2 |
| TRAMP-C2 model | 10 | 10 | 3 |
| TRAMP-C2 model T cell transfer | 8 | 8 | 2 |
| FVB control | 17 | 13 | 2 |
| MC-$Rag^{-/-}$ T cell + B cell transfer | 5 | 18 | 2 |
| MC-WT + B cell depletion | 14 | 16 | 1 |
| MC-$Cd8a^{-/-}$ + B cell depletion | 6 | 6 | 1 |
| Total | 220 | 243 | 42 |
| Total numbers: 468 | | | |

Mouse treatment studies were "matched design control trials." Accordingly, mice were randomly chosen and paired based on sex (male), age (FIG. 6a) and tumor size. For transplanted tumor models, tumor size was defined by the median tumor volume (e.g. 400 mm³, for late treatments, FIG. 6a,f). For TRAMP transgenic tumor models, treatment decisions were made based on age and mice were randomly chosen including a control littermate. An identification code was assigned to each tumor-bearing mouse both in the transplanted and transgenic models, and the investigators were blinded to treatment allocation at the time of tumor volume measurement, autopsy and analysis.

Flow Cytometry and Lymphocyte Isolation

For lymphocytes isolated from spleen and lymph nodes, standard protocols using filters have been used. Lymphocytes were isolated from human blood using Ficoll-Paque PLUS (GE Healthcare Life Science) according to manufacturer's recommendations. For lymphocyte isolation from tumors (mouse and human), tumors were cut into small pieces and incubated in dissociation solution (RPMI medium supplemented with 5% FBS, collagenase type I (200 U/ml), collagenase type IV (200 U/ml), and DNase I (100 µg/ml) for 30 min at 37° C. After incubation, cell suspensions were passed through a 50 µm cell strainer and washed twice. For large tumors (≥0.7 g), hematopoietic cells were pre-enriched using density gradient centrifugation (Percoll or Ficoll), and red blood cells were lysed (RBC Lysis buffer, multi-species; eBioscience). For blocking of Fc-mediated interactions, mouse cells were pre-incubated with 0.5-1 µg of purified anti-mouse CD16/CD32 (93) per 100 µl and human cells were incubated with FcR blocking reagent (Miltenyi Biotec). Isolated cells were stained with labeled antibodies in PBS with 2% FCS and 2 mM EDTA or cell staining buffer (Biolegend). Dead cells were excluded based on staining with Live/Dead fixable dye (eBioscience). For intracellular cytokine staining, cells were restimulated (Myc-Cap cell lysate, PMA/ionomycin or PMA/ionomycin/LPS, as indicated) in the presence of a protein transport inhibitor cocktail containing Brefeldin A and Monensin (eBioscience), as indicated. For CD107, a staining antibody was added to the culture during the stimulation. After 5 hrs, cells were fixed and permeabilized with BD™ Cytofix/Cytoperm reagent for cytokine staining. BD™ transcription factor buffer was used for Foxp3 and T-bet staining and BD™ Phosflow was used for p-SMAD2/3 and p-STAT staining (BD Biosciences) according to manufacturer's recommendations. After fixation/permeabilization, cells were stained with labeled antibodies of interest. Moreover, Il10 and β-actin mRNA expression were analyzed on single cell level by flow cytometry in combination with CD45, IgA and IL-10 protein staining, using FlowRNA II Assay kit (Affymetrix eBioscience) according to manufacturer's protocols[9]. Cells were analyzed on a Beckman Coulter Cyan ADP flow cytometer. Data were analyzed using FlowJo software (Treestar). Immune cell analysis of tumor-free mice of different genetic backgrounds (C57BL/6 and FVB) and different genetic ablations are shown in FIG. 15a-m. The gating strategies and isotype controls for p-STAT1 and IL-10 staining are shown in FIG. 15n-q.

Adoptive Lymphocyte Transfer

Figure 4:
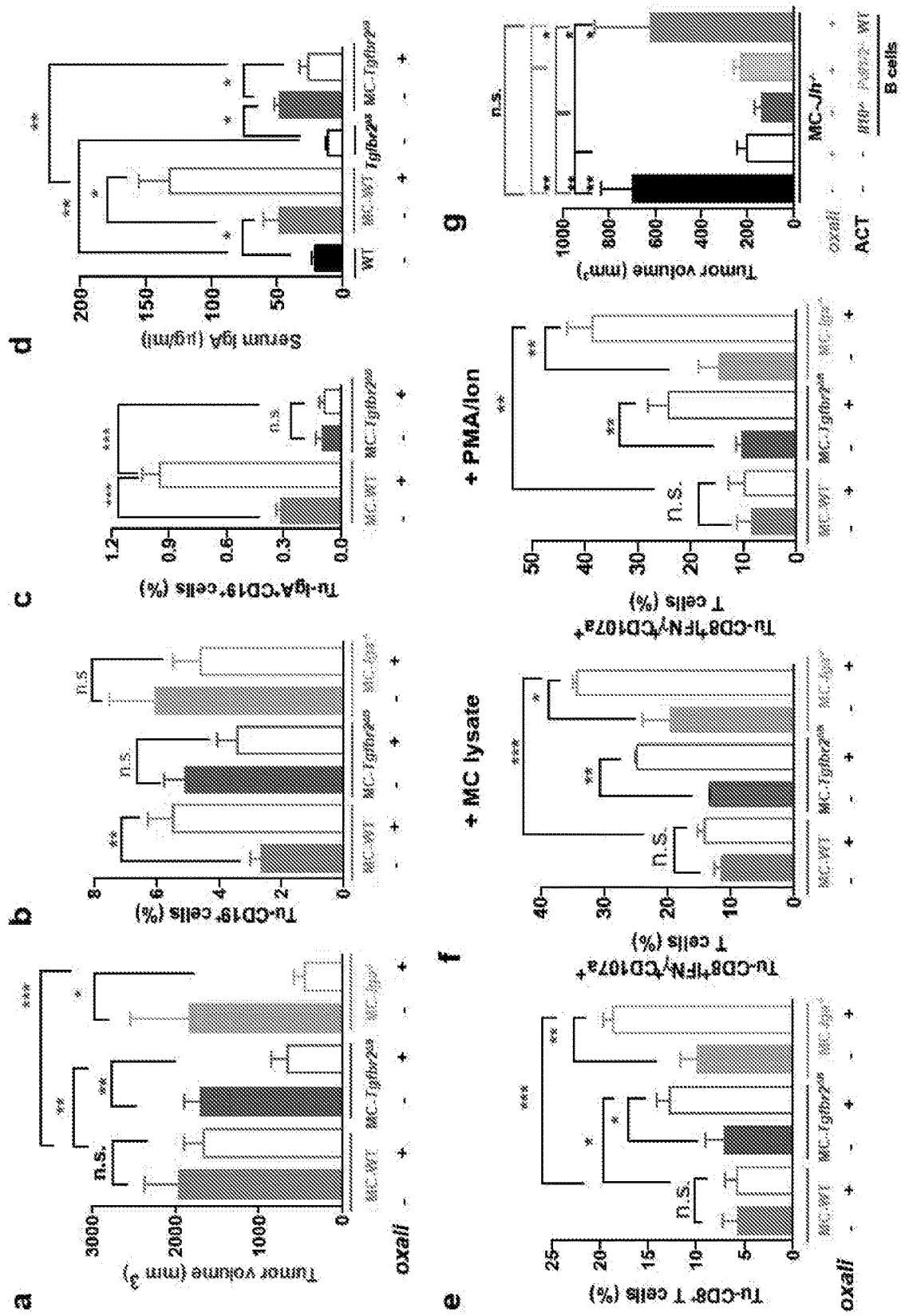
FIG. 4: TGF□R signaling and IgA class-switch recombination are required for development of immunosuppressive plasmocytes. a, MC tumors were raised in WT, Tgfbr2$^{ΔB}$ or Iga$^{-/-}$ mice until 400 mm$^3$ in size, after which mice were given 3 weekly oxaliplatin cycles (n=5-11 per group, total: 48). Tumor volumes at treatment end were analyzed (Kruskal-Wallis test: P=0.0004***). b, c, Tumor-infiltrating CD19$^+$ (b) and IgA$^+$ (c) cells, shown as percentages of tumoral CD45$^+$ cells (b) or total vital cells (c) (n=4-7 per group). d, Serum IgA in treated and untreated MC-WT and MC-Tgfbr2$^{ΔB}$ mice (n=5-8 per group). Naïve tumor-free WT and Tgfbr2$^{ΔB}$ mice are shown as controls. e, Frequency of tumor-infiltrating CD8$^+$ T cells in mice from (a). f, CD8$^+$ T cells (5×10$^6$ per well) from MC tumors in (a) were re-stimulated for 4 hrs with either MC lysate (left) or PMA/ionomycin (right) and analyzed for the indicated markers. Percentages of IFNγ$^+$CD107a-expressing CD8$^+$ T cells within tumoral CD8$^+$ cells are shown (n=4-7 mice per group). g, B cells (5×10$^6$; 98% pure) from WT, Pdl1/2$^{-/-}$ and Il10$^{-/-}$ (mice were transferred into MC tumor-bearing Jh$^{-/-}$ mice (16 days after inoculation) that received oxaliplatin 2 days later. Tumor volumes were determined on day 30 (n=4-6 mice per group). h, Tumor infiltrating CD8$^+$ T cells from Jh$^{-/-}$ MC tumor-bearing mice transplanted with B cells and treated as above were re-stimulated for 4 hrs with PMA/ionomycin before analysis of IFNγ and CD107a (n=4-6 mice per group). Results are means±s.e.m. Mann-Whitney and t tests were used to calculate statistical significance between two groups.
Figure 12:
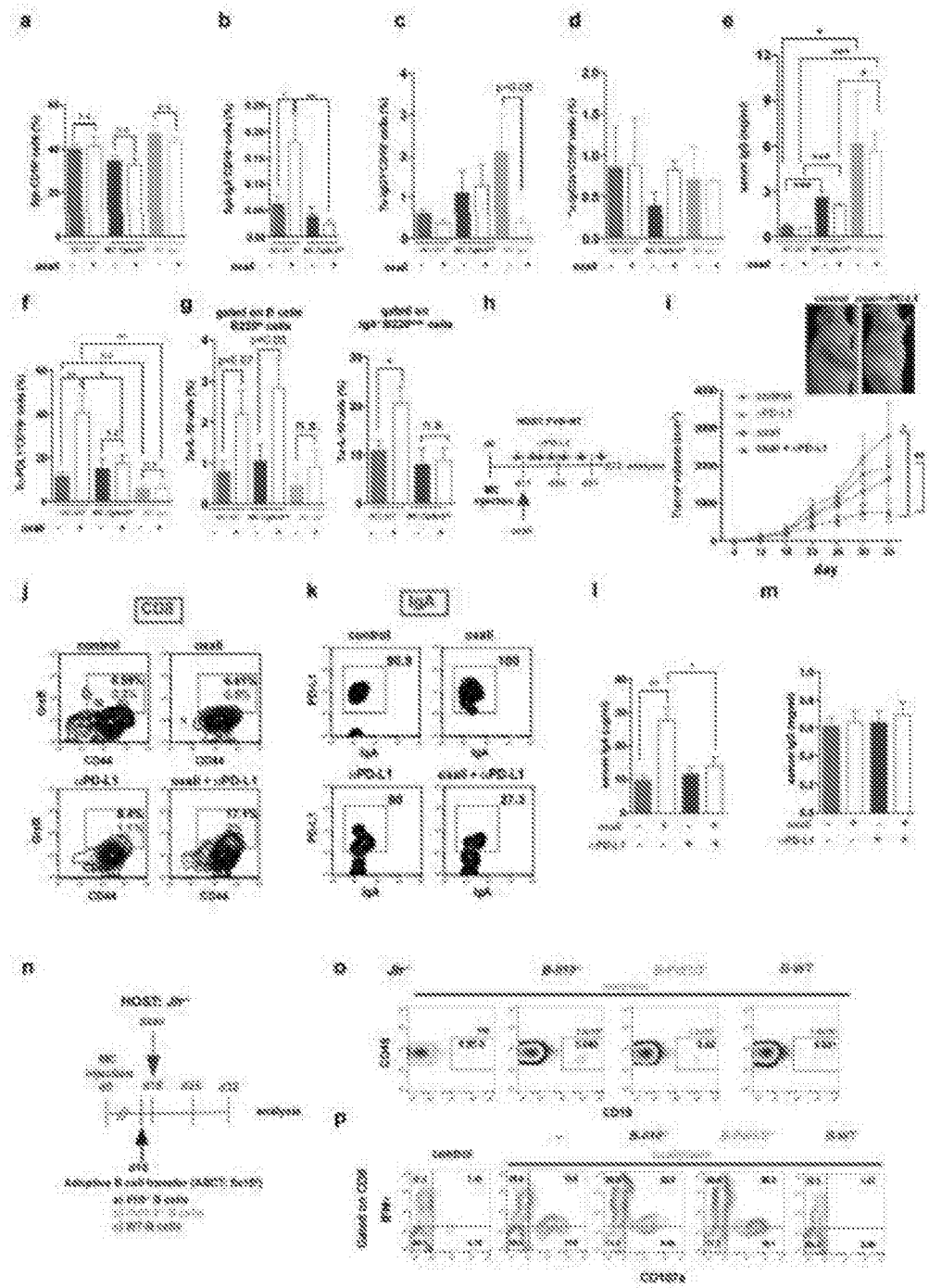
FIG. 12: Effects of TGFβR2, IgA, PD-L1 and IL-10 ablations on tumor-infiltrating lymphocytes. MC tumors were raised in WT, Tgfbr2$^{ΔB}$ or Iga$^{-/-}$ mice (n=5-1 per group). Mice were subjected to 3 cycles of late oxaliplatin treatment after which splenic (Spl) and tumoral (Tu) B cells were analyzed. After dead cell exclusion, splenic (a,b) and tumoral (c,d) B cells were stained with CD19, B220, IgA, IgG2a and IgG1 antibodies and analyzed by flow cytometry. e, Serum IgG concentrations in control or oxaliplatin-treated WT, Tgfbr2$^{ΔB}$ or Iga$^{-/-}$ mice bearing MC tumors (n=5-9 per group). f, Flow cytometry of tumor-infiltrating CD19$^+$ B cells from WT, Tgfbr2$^{ΔB}$ or Iga$^{-/-}$ MC tumor-bearing mice (n=4-7 per group) analyzed for PD-L1 expression, revealing lower PD-L1 surface expression on Tgfbr2$^Δ$ and Iga$^{-/-}$ B cells after oxaliplatin treatment. g, Flow cytometry of tumor-infiltrating B220$^{hi}$ B cells (left) and IgA$^+$ B220$^{low}$ B cells (right) from WT, Tgfbr2$^{ΔB}$ or Iga$^{-/-}$ MC tumor-bearing mice (n=4-7 per group) analyzed for IL-10 expression, revealing no difference in IL-10 expression by B220$^{hi}$IgA$^-$ B cells in the corresponding groups, and lower IL10 expression by Tgfbr2$^Δ$B cells after oxaliplatin treatment compared to WT mice. Results are means±s.e.m. Mann-Whitney and t tests were used to calculate statistical significance. h, The experimental scheme. WT mice bearing MC tumors were divided into four treatment groups (n=7-8 each group): 1) isotype control (IgG2a); 2) oxaliplatin (weekly); 3) anti-PD-L1 (twice weekly); 4) oxaliplatin plus anti-PD-L1 (weekly and twice weekly, respectively). After 3 treatment cycles, mice were sacrificed and analyzed. i, Tumor growth curves of tumor-bearing mice and gross appearance of untreated and treated mice. Significance was determined by Mann-Whitney and t tests. j, Flow cytometric analysis for GrzB expression by tumor-infiltrating CD8$^+$ T effector cells (CD8$^+$CD44$^+$) from MC tumor-bearing mice treated as described above. Results are shown either as percentages of GrzB$^+$ cells amongst CD8$^+$ T cells (black), or percentages of GrzB$^+$-CD8$^+$CD44$^+$ T cells amongst tumoral CD45$^+$ cells (red). k, Flow cytometry of PD-L1 expression on tumor-infiltrating IgA$^+$CD19$^+$ B cells in the different treatment groups. l,m, Serum IgA (l), and IgG (m) concentrations in the different treatment groups described in panel h. n, The experimental scheme for the experiment whose results are shown in FIG. 4g,h. B cells were isolated from WT, Pdl1/2$^{-/-}$ and Il10$^{-/-}$ mice and 5×10$^6$ cells (purity 98%) were i.p. transferred into MC tumor-bearing Jh$^{-/-}$ mice (16 days after MC cell inoculation). After 2 days (day 18), the mice were given 3 oxaliplatin treatment cycles and analyzed. o, Flow cytometric analysis of splenocytes after staining with CD45 and CD19 antibodies, confirming presence of B cells in the ABCT groups. Shown are percentages and absolute B cell numbers in spleen.

For adoptive T cell transfer (ATCT) CD8⁺ T cells were isolated from single cell suspensions, prepared from spleens and lymph nodes as described above, using CD8α-specific microbeads and MACS-columns (both Miltenyi Biotec GmbH, Bergisch Gladbach, Germany), and 5×10⁶ CD8⁺ T cells were transferred intraperitoneally (i.p.; FIG. 14a-j). For adoptive B cell transfer (ABCT), B cells (B220⁺/CD19⁺) were isolated from single cell suspensions prepared from spleens using CD19- and B220-specific microbeads and MACS-columns, and 5×10⁶ B cells were transferred i.p. (FIG. 4g-h, FIG. 12n,o). For adoptive splenocytes transfer (ACT), single cell suspensions prepared from spleens were transferred i.p., with one total spleen injected per mouse. Labelling with 5-(and 6-) carboxyfluorescein diacetate succinimidyl ester (CFSE; Molecular Probes, Eugene, Oreg.) was done according to manufacturer's protocol. 5×10⁶ CD8⁺ T cells or 7×10⁶ B cells were transferred (equal to one spleen per mouse; FIG. 5a-i and FIG. 14k-q). For combined adoptive B and T cell transfer (FIG. 5j-1, FIG. 14r-t), T cells were isolated from WT-FVB mice immunized with a Myc-Cap cell lysate as previously described[10]. Specifically, Myc-Cap cells were incubated in vitro with oxaliplatin (40 µM) for 48 hrs. The extent of cell death was determined by flow cytometry, showing that more than 90% of cells were positive for Annexin V and PI. The dead cells were injected subcutaneously (s.c.) into WT-FVB mice. Seven days later, T cells were isolated from single cell suspensions of spleen and LN using a Pan T cell isolation Kit (Miltenyi Biotec). B cells were isolated from spleens of naïve FVB-WT or FVB-Tgfbr2$^{\Delta B}$ mice using a Pan B cell isolation kit (Miltenyi Biotec). MC-tumor bearing Rag1$^{-/-}$ mice received 5×10⁶ T cells with or without 5×10⁶ B cells (98% pure) from WT or Tgfbr2$^{\Delta B}$ mice. Purity was analyzed on a Beckman Coulter Cyan ADP flow cytometer and was always >98%.

Absolute numbers of particular immune cells in spleen were calculated by multiplying the CD45⁺ cell number from one spleen by the percentages of the particular cell type amongst CD45⁺ cells. Absolute numbers of particular immune cells (e.g. CD8⁺ cells) in tumors was calculated by multiplying the cell number in one tumor portion by the percentages of the corresponding cell type in vital tumor cells divided by the weight of the analyzed tumor fragment.

Subcutaneous Tumor Models

2×10⁶ Myc-Cap[11] or 3×10⁶ TRAMP-C2[12] cells (purchased from ATCC) were s.c. injected into the right flank. Tumors were measured every 2-3 days using a caliper. Tumor volumes were calculated as width²×length/2.

Immune-Mediated B Cell Depletion

B cells were depleted as previously described[13]. Mice were weekly injected (i.p.) with a mixture of monoclonal antibodies, each at 150 µg/mouse: rat anti-mouse CD19 (clone 1D3), rat anti-mouse B220 (clone RA36B2), and mouse anti-mouse CD22 (clone CY34). After 48 hrs, the mice were injected with a secondary antibody (mouse anti-rat kappa chain; GeneTex) at 150 µg/mouse. In addition, mice were injected weekly, but not on the same day, with 250 µg/mouse rat anti-mouse CD20 (Genentech). Rat anti-mouse IgG2a and IgG1 were used as isotype controls. Mice were treated for 3 weeks in total (FIG. 1g; FIG. 7i-p).

Oncomine Data Analysis

In silico analysis of human IgA (IGHA1) mRNA expression was performed using 15 PC microarray gene datasets[14-28] from the Oncomine database (Compendia Biosciences; Ann Arbor, Mich., USA; www.oncomine.org)[29] comparing a combined 126 carcinoma/adenocarcinoma specimens to 30 normal (either benign, disease-free normal and/or normal adjacent) tissue specimens. Evaluation criteria were set as p<0.05, fold change >2.0, and gene rank in the top 10%.

Analysis of Human Specimens

Paraffin-embedded specimens from a total of 110 PC patients were integrated into a tissue microarray system (TMA) constructed at the Clinical Institute of Pathology at the Medical University of Vienna (MUV). All of the human specimens used for TMA construction were approved by the MUV Research Ethics Committee (1753/2014). The cohort included 87 patients with early PC (E-PC), 9 patients with therapy-resistant PC (TR-PC), and 15 patients with metastatic PC (M-PC). Patients' demographic and histopathological features are shown below in Table 2.

TABLE 2

|  |  | Ratio CD20+/CD8+ (IRA %)[b] | | | IgA-CD138+ double positive cases | |
|---|---|---|---|---|---|---|
|  |  | N | Median (1st-3rd quartile) | P[c] | % | P[d] |
| All cases | | 110 | 0.25 (0.06-1.00) | | 41.8 | |
| Patient demographics | | | | | | |
| Age | <75 yrs. | 43 | 0.20 (0.10-0.36) | 0.49 | 37.2 | 0.16 |
|  | ≥75 yrs. | 43 | 0.13 (0.07-0.75) | | 23.3 | |
|  | NA | 24 | | | | |
| Tumor features | | | | | | |
| pT staging | pT2 | 56 | 0.23 (0.10-0.47) | 0.48 | 35.7 | 0.81 |
|  | pT3/pT4 | 36 | 0.15 (0.06-0.66) | | 33.3 | |
|  | NA[a] | 18 | | | | |
| Gleason grade | ≤6 | 36 | 0.23 (0.11-1.03) | 0.10 | 27.8 | 0.23 |
|  | 7 | 43 | 0.12 (0.07-0.35) | | 32.6 | |
|  | ≥8 | 13 | 0.34 (0.19-0.75) | | 53.8 | |
|  | NA[a] | 18 | | | | |
| Stage of disease | Early stage | 86 | 0.20 (0.07-0.51) | <0.001 | 30.2 | <0.001 |
|  | Therapy resistance | 9 | 0.67 (0.34-1.35) | | 77.8 | |
|  | Metastasis | 15 | 2.63 (0.33-8.44) | | 86.7 | |

[a]Not available (NA) cases were not included in the analysis.
[b]Ratio CD20+/CD8+ cells (IRA %) is expressed as percentage immunoreactive area
[c]By Mann-Whitney test.
[d]By Chi-square test.

TMA were designed to provide two cores of normal prostate tissue and four cores of PC tissue from each E-PC patient, and 3-6 cores of tumor tissue for each TR-PC and M-PC patient. Stained TMA slides were digitalized by virtual microscopy at 20× magnification with a fixed light intensity and resolution into a bright-field image using the Nanozoomer (Hamamatsu) scanner. Computer-assisted image analysis of individual TMA core images was used to quantify the percentage of CD8+ and CD2+ immune reactive area (IRA %) as a proportion of the total digitized haematoxylin-stained region, as previously described[30]. For each PC patient, the mean continuous values of CD8+ and CD20+ IRA % in TMA cores without technical artifact for normal and tumor prostate tissue were calculated and used for subsequent statistical analysis. The presence of CD138+ and IgA+ double immunoreactivity for plasma cells in the stromal compartment or directly contacting a cancer cell was semi-quantitatively scored in TMA cores for each patient by an investigator who was blinded to the patients tumor features. A value of 0 was assigned to tissue cores without evidence of stromal CD138+/IgA+ double immunoreactive cells and a value of 1 was recorded when CD138+/IgA+ double immunoreactive cells were present in the stromal compartment. Furthermore, after approval from the UCSD institutional review board (IRB), whole tissue slides were subjected to immunohistochemical (IHC) analysis of αSMA+/IgA, CD8+/IgA and IL-10+/IgA double staining from a cohort of formalin-fixed, paraffin-embedded (FFPE) radical prostatectomy specimens. As previously described[31], this cohort included up to 50 patients, which were selected based on known clinical outcome according to risk categories of low-, intermediate- and high-risk groups based on the D'Amico risk classification[32].

Anonymized fresh prostatectomy and blood samples from consented human subjects, and de-identified clinical information were provided under the UCSD Moores Cancer Center Biorepository and Tissue Technology IRB approved protocol and provided to investigators (M.K, C.J.K., C.A.M.J., D.E.H.) with Cancer Sample Banking Committee approval. Fresh. de-identified samples of human prostate tissue and blood in 10 ml EDTA-coated tubes were collected from patients undergoing radical prostatectomy for clinically localized, intermediate or high risk PC, Gleason grade 3+4 or higher. A board-certified genitourinary pathologist (D.E.H.) collected samples of fresh prostate tumor and adjacent benign tissue, within 1 hr of radical prostatectomy, that were 5-10 mm in diameter.

Immunostaining

Tissues were embedded in Tissue Tek OCT (Sakura Finetek, Torrance, Calif. USA) compound and snap-frozen. Tissue sections were fixed in cold acetone/methanol or 3% PFA for 3-10 min and washed with PBS. Slides were blocked with 1×PBS/1% normal donkey or goat serum for surface staining or 0.2% gelatin (from cold water fish skin; Sigma-Aldrich)/PBS/1% normal donkey or goat serum for intracellular staining for 30 min. Sections were incubated with primary antibodies for 1 or 12 hrs at RT or 4° C., respectively. After washing with PBS, secondary antibodies were added for 1 hr at RT. As negative controls, samples were incubated with isotype-matched control antibodies or secondary antibodies only. After staining with DAPI, sections were covered with Vectashield Mounting Medium (Vector Laboratories, Burlingame, Calif. USA). TMA tissue slides from formalin-processed and paraffin-embedded tumor sections were processed for immunohistochemistry. After de-paraffinization and rehydration, sections were immersed in a pre-heated antigen retrieval water bath with a pH 6.1 citrate buffer, or Dako Target Retrieval Solution for 20 minutes at 95-96° C. ImmPRESS™ Polymer System Diaminobenzidine tetrahydrochloride (DAB) peroxidase substrate-based chromogens were used for single staining of CD8, CD20 and for IgA staining when combined with CD138 and for αSMA staining when combined with IgA for IHC of human samples. ImmPACT™ Vector® NovaRED™ peroxidase substrate-based chromogens were used for CD138 staining when combined with IgA for IHC of human samples. ImmPACT™ Vector) Red Alkanine Phosphatase substrate-based chromogens were used for IgA staining when combined with αSMA for IHC of human samples. All stainings were done according to the manufacturer's protocols (Vector Laboratories). Nuclei were lightly counterstained with a freshly made haematoxylin solution then further washed in water and mounted. Sections were examined using an Axioplan 200 microscope with AxioVision Release 4.5 software (Zeiss, Jena, Germany) or TCS SPE Leica confocal microscope (Leica, Germany).

Antibodies

Antibodies specific for the following antigens were used: mAb rabbit to cleaved Caspase 3 (#9661) or p-γH2AX (Ser139; 20E3) (Cell Signaling Technology, Danvers, USA); pAb rabbit to: CD3 (Dako, IS503); αSMA (Dako); Tim-3 (B8.2C12); Tim-1 (RMT1-4); p-SMAD2/3 (D27F4); LC3B (D11) and CD138 (Syndecan-1) (anti-mouse Biolegend; anti-human Dako M115); IgA (mA-6E1, m11-44-2, mRMA-1, anti-mouse eBioscience/Biolegend; anti-human for IHC: Dako, A0262; for FACS: Miltenyi); AID (MAID-2); CD8a (m53-6.7, human DAKO, C8/144B); CD45 (hOKT4); CD20 (AISB12, hL26); CD44 (IM7); CD4(RM4-5); B220 (RA3-6B2); CD19 (m1D3, hHIB19); IgM (II/41); IgD (11-26c); TNF (MP6-XT22); IFNγ (XMG1.2); GrzB (NGZB); CD107a (eBio1D48); PD-1 (J43); PD-L1 (MIH5); FAS-L1 (MFL3); Ki67 (SolA15); IgG2a (m2a-15F8); IgG1 (MI-14D12); IL-10 (mJES5-16E3; hJES3-9D7: IHC: hIL-10: AF-217-NA); CD69 (H1.2F3); FoxP3 (FJK/16s); CD11c (N418); CD11b (M1/70); MHCII (M5/114.15.2); Gr-1 (1A8-166 g); F4/80 (BM8) and NK1.1 (NKR.P1C) (all from eBioscience); CD31 (PECAM-1, MEC 13.3); CD45 (m30-F11); p-STAT1 (pY701) and p-STAT3 (pY705) (BD Bioscience); and αSMA (anti-mouse ab5694; anti-human: DAKO, 1 A4). The following Alexa 594-, Alexa 647-, Alexa 488-conjugated secondary antibodies were used: donkey anti-rat IgG, donkey anti-rabbit IgG, donkey anti-goat IgG and goat anti-rat IgG (Molecular Probes, Invitrogen).

ELISA

Anti-SV40 Tag immunoglobulin ELISA was performed as previously described[33]. IgA and IgG ELISA kits were purchased from eBioscience, and used according to manufacturer's protocols. Tumoral single cell suspension has been prepared as described above in the flow cytometry section, and was washed 2-3 times with 1×PBS/2mMEDTA/ 2% FCS, to remove soluble IgA. Thereafter, about $3\times10^6$ cells/24-well were plated in either 10% FCS/DMEM or Hybridoma medium (Life Technology). After 24 hrs, the supernatants were analysed for IgA content. Media without cells were used as controls.

Treatment with Chemotherapy or Antibodies

Oxaliplatin was diluted in 5% dextrose and i.p. injected weekly at 6 mg/kg as indicated. Anti-PD-L1 antibody was i.v. injected at 10 mg/kg once, followed by 5 mg/kg bi-weekly. Mice were treated for three weeks for a total of 7 doses/animal.

Q-RT-PCR Analysis

Total RNA was extracted using an RNeasy Plus kit (Qiagen). RNA was reverse transcribed using an IScript kit (Biorad). Q-RT-PCR was performed using Ssofast EvaGreen supermix (Biorad) on a Biorad CFX96 machine. Primer sequences are listed below and generally were obtained from the NIH qPrimerDepot (http://mouseprimerdepot.nci.nih.gov). The relative expression levels of target genes were measured in triplicates and normalized against the level of RPL32 expression. Fold-difference (as relative mRNA expression) was calculated by the comparative CT method ($2^{(Ct(RPL32\text{-}gene\ or\ interest))}$).

TABLE 3

| Name | SEQ ID primer 1 | | SEQ ID primer 2 | |
|---|---|---|---|---|
| IFNγ | 8 | TGAACGCTACACACTGCATCT | 9 | GACTCCTTTTCCGCTTCCTGA |
| TNF | 10 | GGTCTGGGCCATAGAACTGA | 11 | CAGCCTCTTCTCATTCCTGC |
| IL-10 | 12 | GGTTGCCAAGCCTTATCGGA | 13 | ACCTGCTCCACTGCCTTGCT |
| Perforin | 14 | TGGAGGTTTTTGTACCAGGC | 15 | TAGCCAATTTTGCAGCTGAG |
| TGFβ1 | 16 | AAGTTGGCATGGTAGCCCTT | 17 | GGAGAGCCCTGGATACCAAC |
| NOS2 | 18 | TCCAGGGATTCTGGAACATT | 19 | GAAGAAAACCCCTTGTGCTG |
| Arginase 1 | 20 | TTTTTCCAGCAGACCAGCTT | 21 | CATGAGCTCCAAGCCAAAGT |
| Granzyme B | 22 | CTCTCGAATAAGGAAGCCCC | 23 | CTGACCTTGTCTCTGGCCTC |
| RPL32 | 24 | TTGTGAGCAATCTCAGCACA | 25 | GGGAGCAACAAGAAAACCAA |
| IL-21 | 26 | CCC TTG TCT GTC TGG TAG TCA TCT T | 27 | GGA GGC GAT CTG GCC C |
| IL-12p35 | 28 | GAGGACTTGAAGATGTACCAG | 29 | CTATCTGTGTGAGGAGGGC |
| IL-12p40 | 30 | GAC CCT GCC CAT TGA ACT GGC | 31 | CAA CGT TGC ATC CTA GGA TCG |
| PD-L1 | 32 | TGC TGC ATA ATC AGC TAC GG | 33 | CCA CGG AAA TTC TCT GGT TG |

Statistical Analysis

Data are presented either averages±S.E.M or median of continuous values and were analyzed by Students' t-test or Mann-Whitney-U, respectively, for comparison of two groups. Kruskal-Wallis test was used to compare three or more groups. Long-rank (Mantel-Cox) tests were used to compare survival curves. Fisher's exact Chi-square P values were used to calculate statistical significance of categorical values between groups. Two tailed p-values of ≤0.05 were considered significant. Unpaired t test-independent studies were used to determine the minimum sample sizes (StatsDirect Version 2.8.0). GraphPad PRISM software was used for statistical analyses.

Example 2: B Cells Confer Oxaliplatin Resistance

Figure 1:
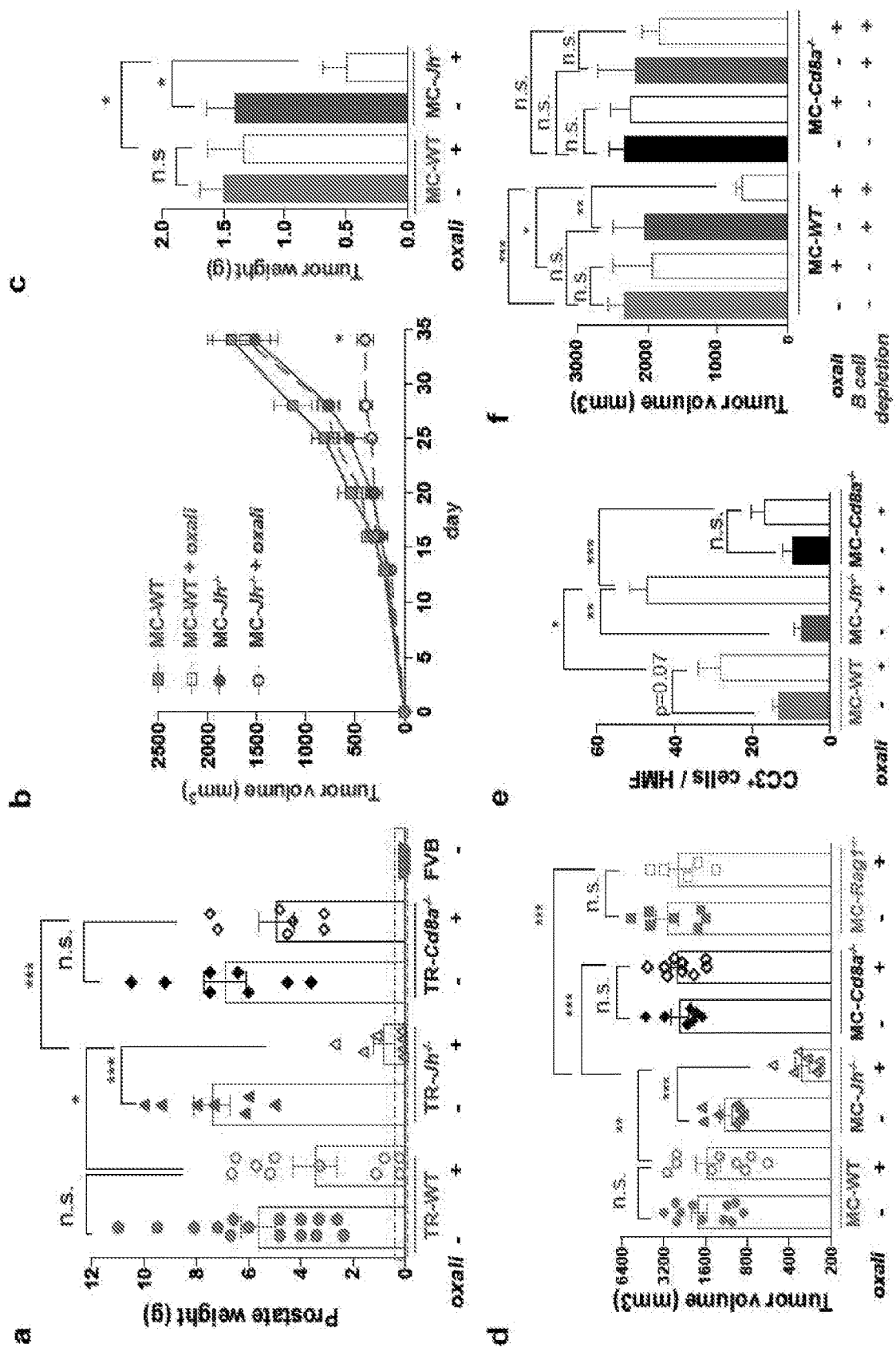
FIG. 1: B cells attenuate the anti-tumorigenic activity of low dose oxaliplatin. a, TRAMP (FVB) mice (TR-WT, TR-Jh$^{-/-}$, and TR-Cd8a$^{-/-}$; n=7-15 per group) received weekly oxaliplatin (6 mg/kg), starting at week 16 (sec FIG. 11a; late treatment). After 4 weeks, mice were sacrificed and prostate weights measured. Dashed red line=prostate weight of naïve controls. b, Tumor growth in mice s.c. transplanted with MC cells and treated with oxaliplatin as in FIG. 11f (late treatment) or 5% dextrose (n=7-11 per group). c, Weights of MC tumors after treatment with oxaliplatin or vehicle (n=5-7 per group). d, Mice of indicated genotypes bearing s.c. MC tumors (n=7-11 per group) were treated as above. After 3 cycles, tumor volumes (mm$^3$) were determined. e, MC tumors from above mice were stained for CD45 (green) and cleaved caspase 3 (CC3; red) (n=4-6 per group). f, Numbers of CC3$^+$ CD45$^-$ cells per high magnification field (HMF; 200×) in tumors from panel (e). Magnification bars: 100 μm. g, MC tumors were raised in WT (left), or Cd8a$^{-/-}$ (right) mice. Sixteen days after inoculation, B cells were depleted with antibodies against CD19, CD20, CD22 and B220. Four days after first twice-weekly antibody treatment, mice received weekly oxaliplatin (n=4-7 per group, total: 42), and sacrificed 3 weeks later. Tumor volumes were analyzed by Kruskal-Wallis test: P=0.007**. Results are means±s.e.m. Mann-Whitney and t tests were used to determine significance indicated as *P, 0.05; P, 0.01; *P, 0.001.
Figure 6:
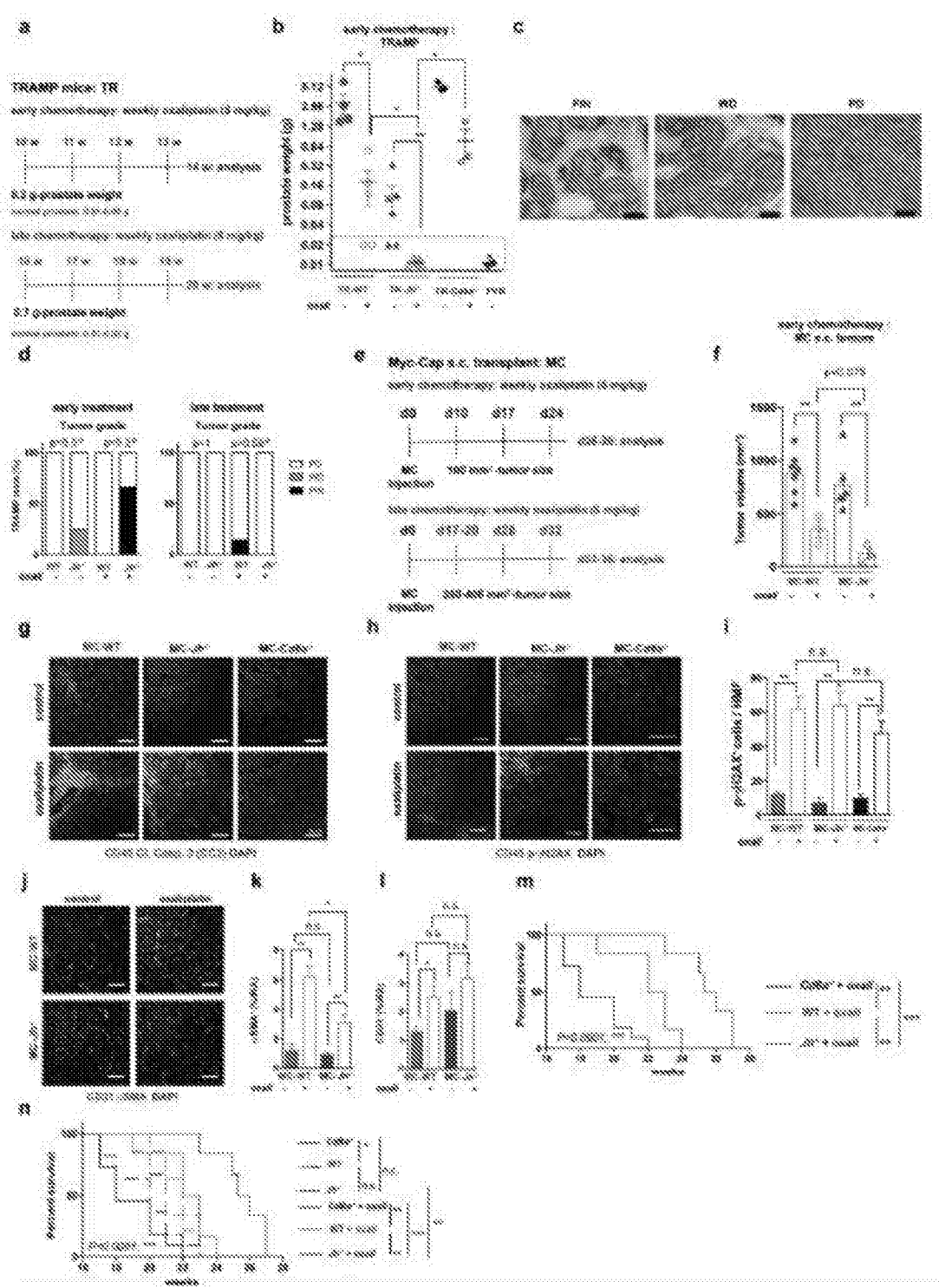
FIG. 6. Treatment schemes and characterization of tumors and mouse survival before and after treatment. a, Early and late treatment schemes for TRAMP mice. b, TRAMP mice (n=3-6 for each group) were subjected to early oxaliplatin treatment as described in (a) and prostate weights were determined at 14 weeks, one week after completion of 4 treatment cycles. Dashed red line indicates prostate weight of tumor-free controls (n=33 in total). c-e, Histopathology of TRAMP tumors. c, Representative images of H&E stained prostate sections from TRAMP mice are shown. Magnification bars: 100 μm. PIN, prostatic intraepithelial neoplasia; WD, well differentiated adenocarcinoma; PD, poorly differentiated adenocarcinoma. d, Histopathological assessment of early TRAMP tumors in WT and Jh$^{-/-}$ mice without or with oxaliplatin treatment. The percentages of the different histotypes shown in (e) are depicted (n=3-7 per group). e, Histopathological assessment of late TRAMP tumors from WT and Jh$^{-/-}$ mice without or with oxaliplatin treatment. The percentages of the different histotypes are depicted (n=3-7 per group). Fisher chi-square analysis was used to calculate statistical significance in (d) and (e). f, Early and late treatment schemes for mice bearing s.c. MC tumors. g, MC cells were s.c. transplanted into WT and Jh$^{-/-}$ mice (n=3-7 per group) that were subjected to early oxaliplatin treatment when tumor volume was 100 mm$^3$. 48 hrs after completion of 3 treatment cycles, mice were sacrificed and tumor volumes (mm$^3$) were measured (n=19 in total). Prostate weight in (g) is shown in a Log 2 scale. h,i, MC tumors (n=3-5 per group) grown in WT, Jh$^{-/-}$ and Cd8a$^{-/-}$ mice were stained for CD45 (green) and p-γH2AX (red), and the p-γH2AX$^+$ foci in CD45$^-$ cells were enumerated (i). Magnification bars: 100 □m. All results are means±s.e.m. j, Representative images of s.c. MC tumors (n=5-6 per group) from WT and Jh$^{-/-}$ mice, with or without oxaliplatin treatment stained for αSMA (green) and CD31 (red). k, l, Frequency of αSMA (k) and CD31 (l) positive cells within tumors from (j). Shown are median values±s.e.m. Mann-Whitney and t tests were used to calculate statistical significance indicated by *P, 0.05; P, 0.01; *P, 0.001. m, TRAMP mice (WT, Cd8a$^{-/-}$ or Jh$^{-/-}$; n=6-14 per group) were treated weekly with low-dose oxaliplatin. Moribund mice were sacrificed, and survival was compared by Kaplan-Meyer analysis and significance was determined (WT: n.s.; Cd8a$^{-/-}$: n.s.; Jh$^{-/-}$; p<0.002;**). n, No statistically significant differences in survival were found between WT and Jh$^{-/-}$ or Jh$^{-/-}$ and Cd8a$^{-/-}$ mice without treatment. o, Significant differences in survival times were observed between all three oxaliplatin-treated groups (WT, Cd8a$^{-/-}$ or Jh$^{-/-}$; indicated on the right). p, Survival curves for all of the groups before and after oxaliplatin treatment. Significant differences in survival times are indicated on the right.

Using the TRAMP model of spontaneous PC which gives rise to metastatic tumors with a neuroendocrine phenotype typical of aggressive, drug resistant human PC[11], we examined how B and CD8$^+$ (CTL) lymphocytes affect the response to low dose (LD) oxaliplatin by crossing TRAMP (FVB) mice to either B cell (Jh$^{-/-}$)[7,12] or CTL (Cd8a$^{-/-}$)[13] deficient mice. Although early (≤0.2 g) tumors responded to oxaliplatin regardless of their B cell status (FIG. 6a,b), upon reaching ≥0.7 g, tumors in WT TRAMP mice became largely resistant to "late" chemotherapy (FIG. 1a). However, PC growth in B cell-deficient TRAMP; Jh$^{-/-}$ mice remained oxaliplatin sensitive (FIG. 1a), although the B cell deficiency had little effect on tumor development and histology (FIG. 6b-c). By contrast, CD8$^+$ cell deficiency modestly attenuated therapeutic responsiveness in small tumors, but barely impacted large, oxaliplatin-resistant, tumors (FIG. 1a; FIG. 6b). Similar results were obtained in a different model based on s.c. transplantation of Myc-Cap (MC) cells[14] (FIG. 6f,g). Whereas small MC tumors (≤100 mm$^3$) were chemotherapy responsive even in WT mice (FIG. 6g), large MC tumors (≥350-400 mm$^3$) shrank upon oxaliplatin treatment only in Jh$^{-/-}$ mice (FIG. 1b-d). No response was observed in Cd8a$^{-/-}$ mice. Oxaliplatin responsiveness was associated with enhanced caspase 3 activation (FIG. 1e,f), indicating more effective apoptosis. However, the tumoral DNA damage response measured by histone H2AX phosphorylation was similarly activated by oxaliplatin, regardless of host genotype (FIG. 6h,i). Oxaliplatin treatment enhanced tumor infiltration with CD45$^+$ cells in WT and Jh$^{-/-}$ mice (FIG. 1c), but induction of myofibroblast activation and CD31 infiltration was more pronounced in WT mice (FIG. 6j-1). LD oxaliplatin enhanced TRAMP mouse survival in a manner dependent on CTL and inhabitable by B cells (FIG. 6m-p). B cell immuno-depletion also enhanced oxaliplatin-induced tumor regression and the effect was CTL-dependent (FIG. 1g).

Example 3: B Cells Suppress CTL Activation

Figure 2:
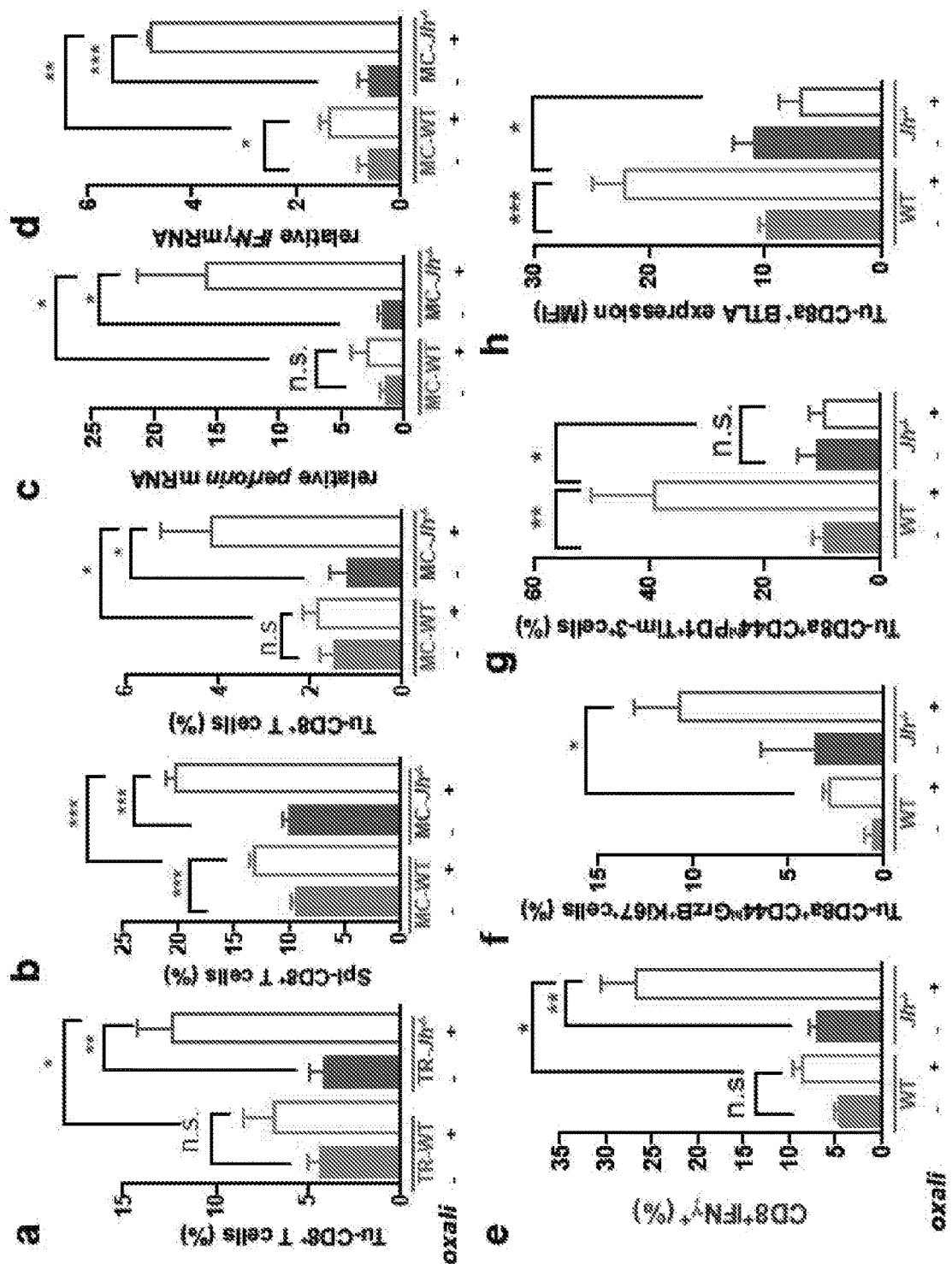
FIG. 2: B cells inhibit oxaliplatin-induced T cell activation. a, CD8$^+$ cell counts in TRAMP prostates (WT, Jh$^{-/-}$; n=4-6 per group) collected from mice treated as in 1a, analyzed by flow cytometry and normalized to CD45$^+$ cells. b, Mice (n=6-8 per group) bearing MC tumors were analyzed as above for CD8$^+$ cells in spleens and tumors after 3 chemotherapy cycles. c, MC tumors from (b) were stained for CD8 (FIG. 12b), and tumor-infiltrating CD8$^+$ cells were counted in 3-4 HMF (200×) per tumor (n=4-5 tumors per group). d, e, Q-RT-PCR analysis of Perforin and Ifnγ mRNA in MC tumors collected as in (b) (n=4-7). f, Flow cytometry for TNF and IFNγ in CD8$^+$ cells from MC tumors of mice treated as above (n=6-8) and re-stimulated in vitro with tumor cell lysate. g-i, Flow cytometry of GrzB and Ki-67 (g), PD-1 and Tim-3 (h) and BTLA (i) in CD8$^+$ T effector cells (CD8$^+$CD44$^+$; g,h) or total CD8$^+$ cells (i) from spleens and tumors of MC inoculated mice. Results are either percentages of positive cells in tumoral CD8$^+$ cells or mean fluorescence intensities (MFI) and are means±s.e.m of three independent experiments (m=6-8 mice per group). Mann-Whitney and t tests were used to determine significance shown as above.
Figure 7:
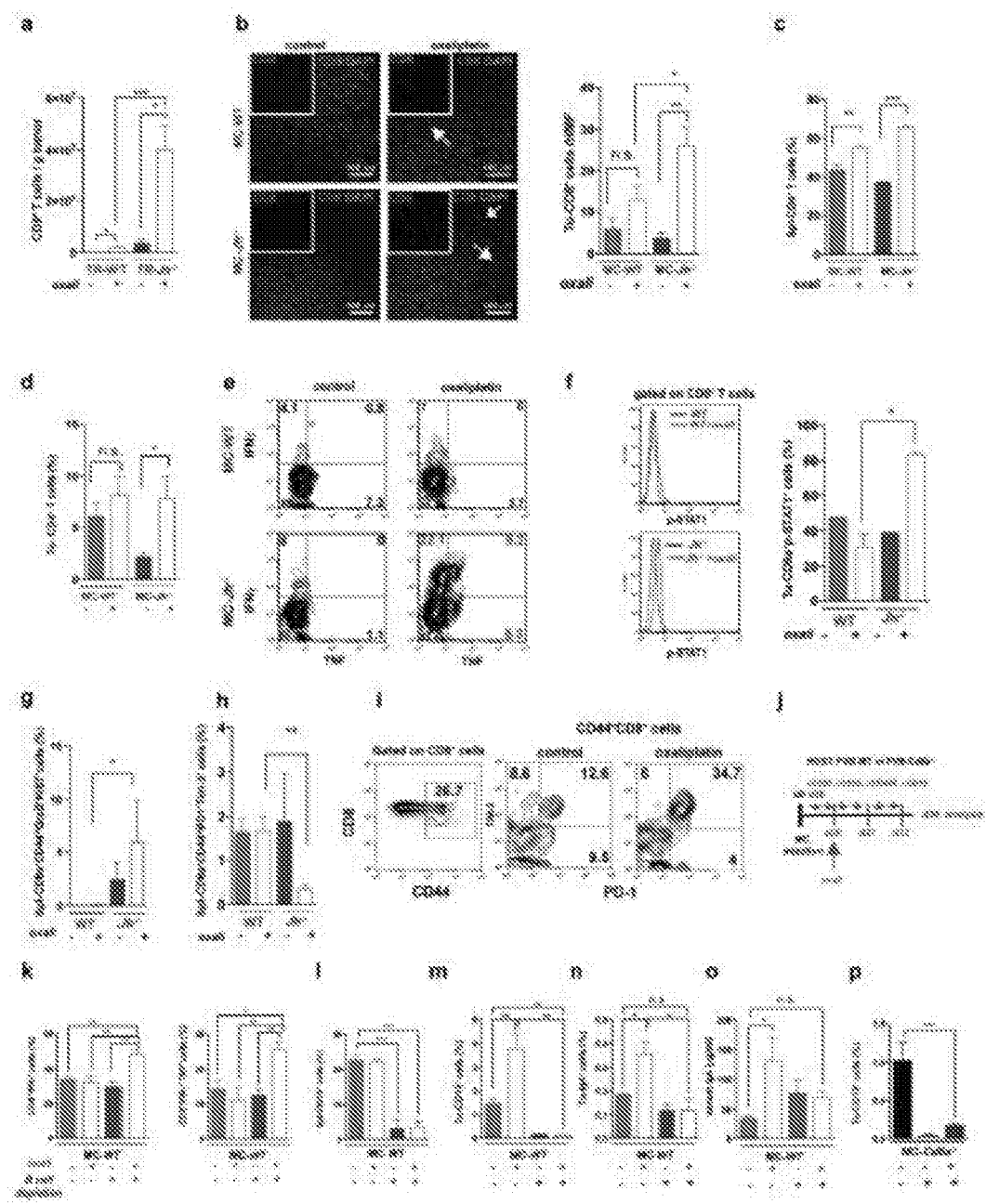
FIG. 7. B cells attenuate oxaliplatin-triggered CTL activation, a, Flow cytometry of CD8$^+$ T lymphocytes in prostates of 20 weeks old TRAMP mice after 4 cycles of oxaliplatin treatment (n=5-7 per group) normalized to prostate weights. b, Late s.c. MC tumors from WT and Jh$^{-/-}$ mice were stained for CD8 and analyzed by immunofluorescent microscopy. In the upper left areas (white square), single CD8 staining (green) without DAPI counterstain is shown. Quantitation of CD8$^+$ cells is shown in FIG. 2c. Magnification bars: 100 □m. c,d, Late s.c. MC tumors were analyzed by flow cytometry for CD4$^+$ lymphocytes in spleens (c) and tumors (d) after 3 oxaliplatin treatment cycles (n=4-7 per group). The results show percentages of CD4$^+$ cells in the CD45$^+$ population. e, Flow cytometric analysis of IFNγ expression by CD8$^+$ cells in MC tumors from WT and Jh$^{-/-}$ mice treated as above (n=6-8) and re-stimulated in vitro with tumor cell lysate. Representative panels are shown in FIG. 2f. The results show percentages of IFNγ-producing CD8$^+$ cells. f, Flow cytometry of STAT1 phosphorylation in CD8$^+$ cells from MC tumors of treated and untreated WT, and Jh$^{-/-}$ mice (for isotype controls, see E.D.

Enhanced oxaliplatin responsiveness in B cell-deficient mice reflected more effective CTL activation. Oxaliplatin stimulated CD8$^+$ cell recruitment in both TRAMP and TRAMP; Jh$^{-/-}$ mice, although many more tumoral CD8$^+$ cells were found in the latter (FIG. 2a; FIG. 7a), The B cell deficiency also enhanced CD8$^+$ cell recruitment into MC tumors after LD oxaliplatin treatment (FIG. 2b,c; FIG. 7b). CD4$^+$ T cell recruitment was also enhanced by B cell absence (FIG. 7c,d). The B cell deficiency strongly enhanced induction of perforin, γ interferon (IFNγ) and TNF by oxaliplatin in MC tumors, with TNF and IFNγ produced by CD8$^+$ cells (FIG. 2d-f; FIG. 7e). Oxaliplatin-treated MC tumors of Jh$^{-/-}$ mice also contained more CD8$^+$ cells with activated STAT1 (FIG. 7f). Jh$^{-/-}$ tumors and spleens also contained more proliferative CD8a$^+$CD44$^{hi}$GrzB$^+$Ki67$^+$ cells before and especially after oxaliplatin treatment (FIG. 2g) and fewer "exhausted"[3] tumoral CD8$^+$CD44$^+$PD-1$^+$Tim3$^+$ and CD8$^+$BTLA$^{hi}$ cells (FIG. 2h,i; FIG. 7g), whose presence in WT tumors was elevated after oxaliplatin treatment. Similar results were observed upon analysis of "exhausted" splenic CD8$^+$ cells (FIG. 7h). B cell immuno-depletion also enhanced tumoral CTL activation (FIG. 7i-p).

Example 4: The Immunosuppressive B Cells are IgA$^+$ Plasma Cells

Figure 3:
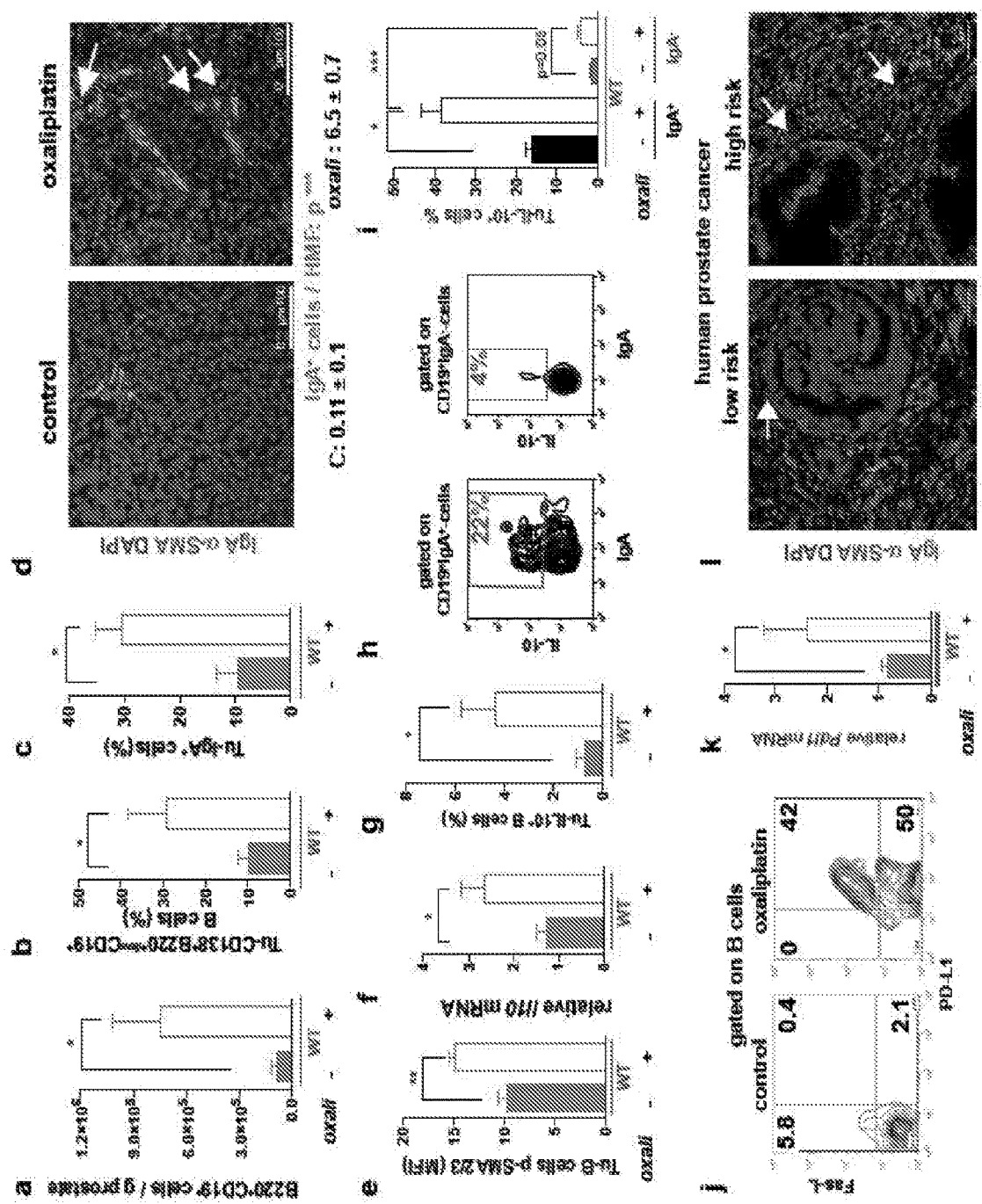
FIG. 3: Oxaliplatin Induces infiltration of prostate tumors with IgA$^+$PD-L1$^+$IL-10$^+$ producing plasmocytes. a, B220$^+$ CD19$^+$ B lymphocytes in 20 weeks old TRAMP prostates after 4 oxaliplatin cycles (n=5-7 per group) normalized to prostate weights. b,c, Flow cytometry of B220, CD19, CD138 and IgA in tumoral B cells from (a). Values are % of tumoral CD45$^+$ (b) or CD19$^+$ (c) cells. d, MC tumors (n=4-5 per group) stained for αSMA (green) and IgA (red). Arrows: IgA$^+$ cells whose number per HMF is shown on the right. e, Flow cytometry of p-SMAD2/3 in tumor-infiltrating B cells (n=3-4 per group). f, Il10 mRNA in MC tumors (n=5-6 per group). g, Tumor-infiltrating IL-10$^+$CD19$^+$ B cells in MC-WT mice, shown as percentages of CD45$^+$ cells. h,i, Percentages of IL-10-producing cells in tumoral CD19$^+$IgA$^+$ (h) and CD19$^+$IgA$^+$ (l) cells from MC-WT mice. j, IL-10 expression by IgA$^+$ and IgA$^-$ B cells in MC-tumors (n=4-6 per group). k, Flow cytometry of PD-L1 and FAS-L in B cells from TRAMP tumors. l, Pdl1 mRNA in MC tumors (n=5-6 per group). m, Low (n=5) and high (n=5) risk human PC specimens stained with IgA (red) and αSMA (green) antibodies. Arrows: IgA$^+$ cells. All results are means±s.e.m of at least three independent experiments. Magnification bars: 100 □m. Mann-Whitney and t tests were used to calculate statistical significance shown as above.
Figure 8:
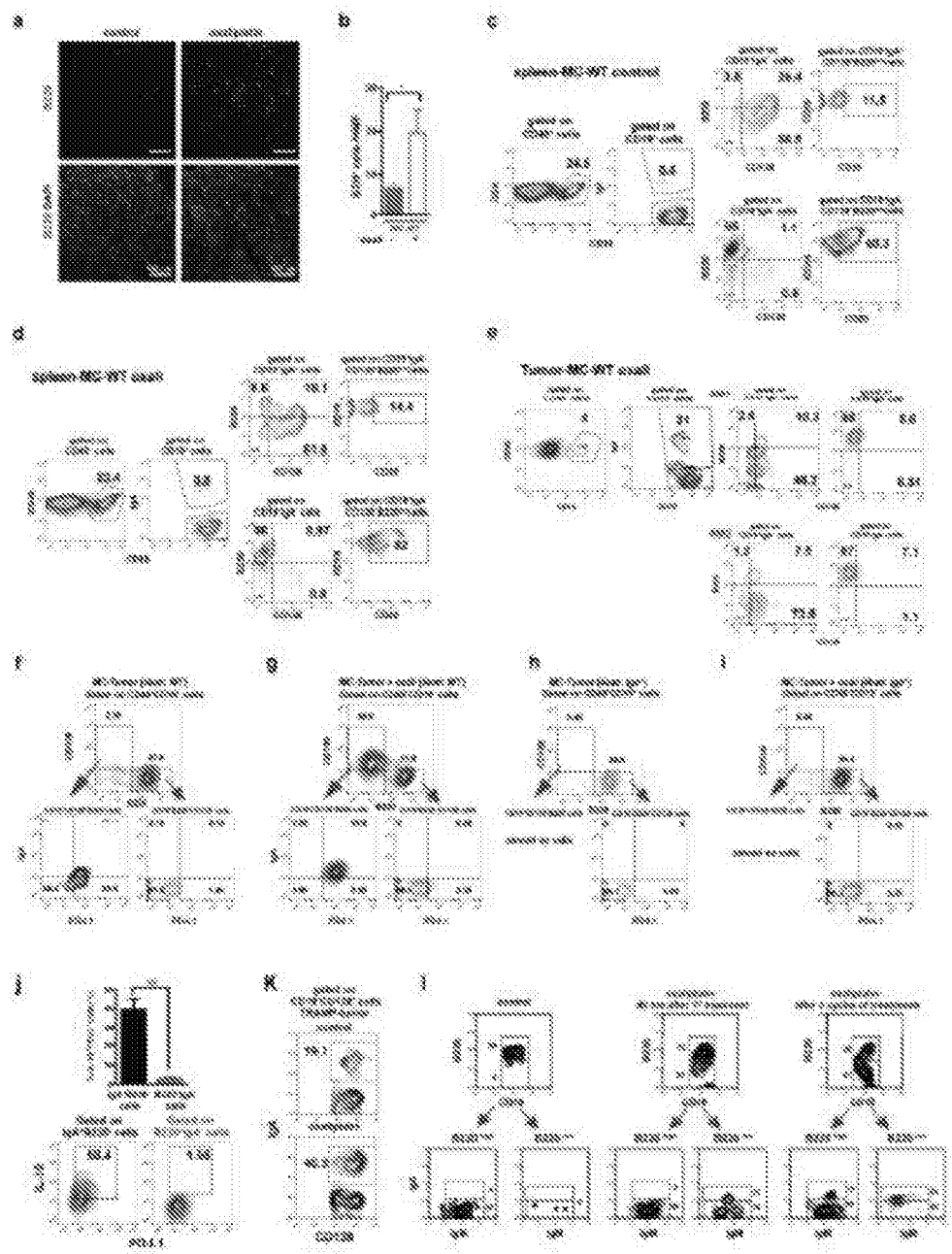
FIG. 8: Immunogenic chemotherapy induces tumor infiltration by immunosuppressive CD19$^+$CD20$^{low}$B220$^{low}$IgA$^+$ B cells. a,b, MC tumors (n=4-9 per group) raised in WT mice without or with oxaliplatin treatment were stained for B220 (a), and tumor-infiltrating B220$^+$ cells per HMF were enumerated (b). In panel a, single B220 staining (above) and combined staining B220/DAPI (below) are shown. Magnification bars: 100 μm. c,d, The flow cytometry plots and gating strategy for analysis of splenic B cell populations using CD19, IgA, B220, CD138 and CD20 antibodies. Results from WT mice bearing MC tumors are shown in panel (c) and from oxaliplatin-treated mice in panel (d) (n=8 mice per group). Oxaliplatin treatment modestly increased the amount of splenic IgA$^+$ cells. Splenic IgA$^+$ cells expressed CD138 as expected and showed lower levels of B220 and CD20, in either control or oxaliplatin-treated mice. e, The gating strategies for analysis of tumoral B cells using CD19, IgA, B220 and CD138 antibodies. Results from MC tumors in two representative oxaliplatin-treated WT mice are shown (n=8 mice per group), demonstrating the presence of IgA$^+$ cells in oxaliplatin-treated tumors with a typical CD138$^+$B220$^{low}$ phenotype. f-i, Flow cytometry plots and gating strategies for analysis of tumoral B cell populations using CD19, B220, CD138, IgA and PD-L1 antibodies. Results from WT mice bearing MC tumors without (f) or with oxaliplatin treatment (g) (n=6 mice per group) and Iga$^{-/-}$ mice bearing MC tumors without (h) or with oxaliplatin treatment (i) (n=6 mice per group) are shown. Oxaliplatin treatment increased the amount of tumoral IgA$^+$CD138$^+$B220$^{low}$PD-L1$^+$ cells in WT mice. j, Flow cytometric analysis of PD-L1 and IL-10 expression in IgA$^+$B220$^-$ and B220$^+$IgA$^-$ B cells from oxaliplatin-treated TRAMP tumors (n=4). k, Flow cytometric analysis of IgA and CD138 expression by TRAMP tumor-infiltrating B cells. Shown are percentages of IgA$^+$ cells amongst all tumor-infiltrating CD19$^+$CD138$^+$ cells. l, WT mice bearing MC tumors were treated with oxaliplatin as above. Two days after the first or last oxaliplatin cycle, mice were sacrificed, tumors were isolated and analyzed by flow cytometry as indicated (n=6 per group). After dead cell exclusion, tumor-infiltrating B cells were stained with CD19, CD20, B220, IgA and IgM antibodies. Shown are the results for control (left panels), one cycle (middle panels), and 3 cycles (right panels) of oxaliplatin treatment, demonstrating the presence of tumoral IgA$^+$ cells with a CD19$^+$CD20$^{low}$B220$^{low}$ IgA$^+$ cell phenotype within 48 hrs after oxaliplatin treatment.
Figure 9:
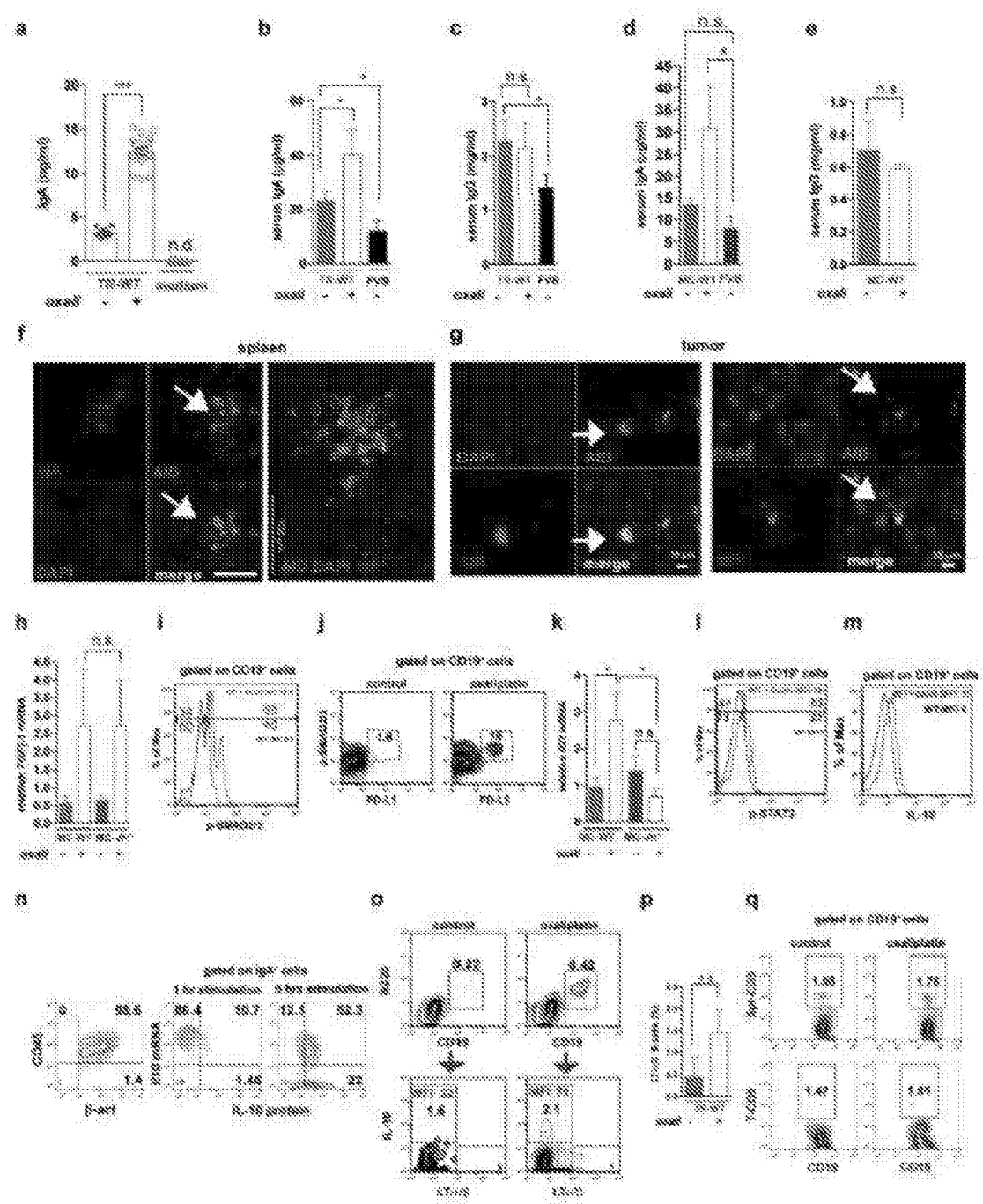
FIG. 9: Immunogenic chemotherapy induces tumoral and systemic IgA production through class switch recombination. a, Ex vivo analysis of IgA released by tumor single cell suspension isolated from oxaliplatin-treated TRAMP tumors. Single cell suspension from non-treated tumors and culture medium without cells were used as controls. b,c, Serum IgA (b) and IgG (c) in treated and untreated TRAMP mice and age-matched naïve FVB controls (n=7-14 per group), d, Serum IgA amounts in control or oxaliplatin-treated mice bearing MC tumors (n=5-7 per group) were determined and compared to age-matched naïve FVB controls (n=7). e, Serum IgG amounts in control or oxaliplatin-treated mice bearing MC tumors (n=5-7 mice per group) were determined and compared to age-matched naïve FVB controls. a-e, Results are means±s.e.m. Mann-Whitney and t tests were used to calculate statistical significance. f,g, Immunofluorescence analysis of activation-induced cytidine deaminase (AID, green) and IgA (red) expression in spleen (f, used as a positive control) and MC tumors from oxaliplatin-treated WT mice (g). Magnification bars: 10 □m except in bottom left panel where it is 100 μm. Arrows point to IgA$^+$AID$^+$ cells. Shown are representative results of spleens and tumors isolated from 4 mice per group. h, Q-RT-PCR analysis of Tgfb1 mRNA in MC tumors raised in WT or Jh$^{-/-}$ mice without or with oxaliplatin treatment (n=3-7 mice per group). Results are means±s.e.m. i, Flow cytometry of SMAD2/3 phosphorylation in MC tumor-infiltrating B cells from WT mice before and after oxaliplatin treatment (n=4 per group). Shown are the mean fluorescence intensities (MFI) and percentages (see FIG. 3e). j, Flow cytometry of SMAD2/3 phosphorylation and PD-L1 in MC tumor-infiltrating B cells from WT mice before and after oxaliplatin treatment (n=4 per group). Shown are the percentages of PD-L1$^+$p-SMAD2/3$^+$ cells within CD45$^+$CD19$^+$ cells. k, Q-RT-PCR analysis of Il21 mRNA in MC tumors raised in WT or Jh$^{-/-}$ mice without or with oxaliplatin treatment (n=4-7 mice per group). Chemotherapy-induced Il21 mRNA mainly in WT mice. l,m, Flow cytometry of tumor-infiltrating B cells stained for phospho-STAT3 and IL-10 (n=5-6 per group) before and after oxaliplatin treatment. n, Flow cytometry analysis of □-actin mRNA, IL-10 protein and Il10 mRNA in MC tumor-infiltrating IgA$^+$ cells using PrimeFlow™ RNA technology (pooled data of 4 mice per group, after oxaliplatin treatment). Left panel: □-actin mRNA gated on CD45$^+$ cells; middle panel: Il10 mRNA and IL-10 protein expression after 1 hr stimulation with PMA/ion/LPS gated on IgA$^+$ cells, right panel: Il10 mRNA and IL-10 protein expression after 5 hrs stimulation with PMA/ion/LPS, gated on IgA$^+$ cells. o,p, Flow cytometric analysis of tumor-infiltrating B cells in TRAMP mice (n=4-5 per group) stained for CD19, B220, IL-10 and LT□β (o). The percentage of tumor-infiltrating LTαβ$^+$ cells amongst all tumor-infiltrating B cells was determined (p). q, Flow cytometric analyses of CD5 expression by B cells from spleen and MC-tumor of WT mice after oxaliplatin treatment (n=4-5 per group). Shown are means±s.e.m. Mann-Whitney and t tests were used to calculate statistical significance indicated by *P, 0.05; P, 0.01; *P, 0.001.
Figure 10:
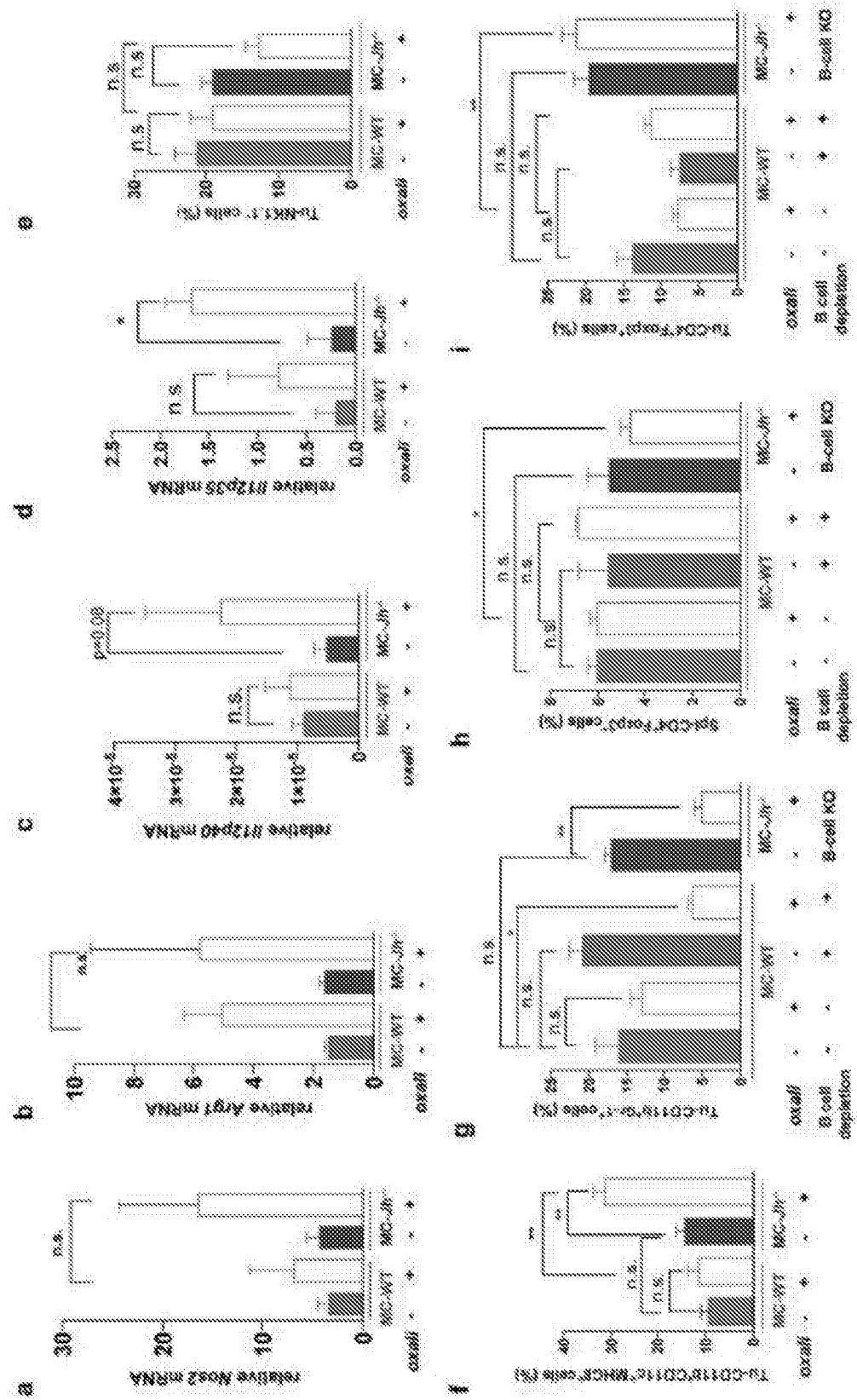
FIG. 10: Immunogenic chemotherapy or B cell deficiency has marginal effects on Tregs, NK and myeloid cells. a,b, Q-RT-PCR analyses of Nos2 (a) and Arg1 (b) mRNA content of MC tumors (n=4-7 mice per group). Chemotherapy induced Nos2 and Arg1 expression in WT and Jh$^{-/-}$ mice and no significant and consistent differences were found between both groups. c,d, Q-RT-PCR analyses of Il12p40 (c), Il12p35 (d) mRNA in MC tumors grown in WT and Jh$^{-/-}$ mice (n=4-6 mice per group). e-i, Flow cytometry analyses of tumor-infiltrating or splenic lymphocytes and monocytes: tumoral Nk1.1$^+$ cells (e), tumoral CD11b$^+$CD11c$^+$MHCII$^+$ cells (f), tumoral CD11b$^+$GR-1$^+$ cells (g), CD4$^+$FoxP3$^+$ cells (splenic, h; tumoral, i). Cells in panels e-i are from tumor-bearing mice subjected to oxaliplatin treatment and/or B cell depletion as indicated (B cell depletion+ oxaliplatin; n=4-6 mice per group). Results are means±s.e.m. Mann-Whitney and t tests were used to calculate statistical significance.

Which tumor infiltrating B cells suppress CTL activation? Oxaliplatin treatment greatly increased the number of tumoral B220$^+$CD19$^+$ B cells (FIG. 3a, FIG. 8a,b). After 3-4 cycles of oxaliplatin treatment, at least 40% of the tumoral B cells were CD19$^+$B220$^{low}$CD138$^+$ plasma cells, depending on the tumor model used, 40-80% of which expressed IgA (FIG. 3b,c; FIG. 8c-1). As described[15], plasma cells down-regulated CD20 expression (FIG. 8c-l). IgA$^+$ B cells became detectable 48 hrs after the first oxaliplatin cycle, and their abundance increased to nearly 80% of B220$^{low}$ cells after additional cycles (FIG. 8g,l). When cultured ex vivo, tumoral IgA-B cells released soluble IgA (FIG. 9a). Oxaliplatin treatment also increased serum IgA, but had little effect on serum IgG, in both TRAMP and MC-tumor models (FIG. 9b-c). IgA$^+$ cells with plasmocyte morphology were often found adjacent to α smooth muscle actin (αSMA)-expressing myofibroblasts (FIG. 3d), cells that produce CXCL13[16]. Oxaliplatin-induced IgA$^+$ B cells from spleen and MC tumors expressed activation-induced cytokine deaminase (AID) (FIG. 9f,g), suggesting recent occurrence of class-switch recombination (CSR).

The IgA CSR is induced mainly by TGFβ in combination with CD40L, IL-21, IL-10 or IL-6[17,18]. Accordingly, oxaliplatin treatment increased the proportion of tumoral B cells undergoing TGFβ signaling, including phosphorylated SMAD2/3 in B cells and higher Tgfb1 mRNA in tumors (FIG. 3e; FIG. 9h-j). IL-21 ensures TGFβ-induced IgA CSR, via STAT3 signaling[18]. Indeed, oxaliplatin treatment increased IL-21 expression and enhanced STAT3 phosphorylation in tumoral B cells (FIG. 9k,l). Oxaliplatin also increased Il10 mRNA expression in tumors, the number of tumor-infiltrating IL-10 producing B cells and the amount of IL-10 per B cell (FIG. 3f,g; FIG. 9m), mainly in IgA$^+$CD19$^+$ plasmocytes (FIG. 3h-j), 50% of which contained both IL-10 mRNA and protein (FIG. 9n). Oxaliplatin also induced Fas ligand (Fas-L) and PD ligand 1 (PD-L1), and about 50% of the IgA$^+$ B cells expressed both molecules (FIG. 3k,l, FIG. 8f-i). Similarly, about 40% of oxaliplatin-induced IgA$^+$ cells expressed both PD-L1 and IL-10 (FIG. 8j). Some PD-L1$^+$ B cells (nearly 90% of which were IgA$^+$) showed SMAD2/3 phosphorylation (FIG. 9j). Notably, LTα/β-producing B cells did not express IL-10 and their abundance was barely increased by oxaliplatin (FIG. 9o,p). CD19$^+$ cells from either untreated or oxaliplatin-treated tumors did not express CD5, a marker of B regulatory (Breg) cells[19] (FIG. 9q). Oxaliplatin treatment induced other immunoregulatory molecules, including Nos2, Arg1, IL-12p35 and IL-12p40, but no differences were observed between tumor-bearing WT and Jh$^{-/-}$ mice, although the latter expressed higher levels of anti-tumorigenic[20] IL-12 (FIG. 10a-d). B cell deficiency or depiction had no significant effect on tumoral NK cells, myeloid CD11b$^+$Gr1$^+$ cells, macrophages or Treg (FIG. 10e-i). Thus, unlike mouse squamous cell carcinoma, where B cells modulate tumor growth and therapeutic responsiveness through effects on macrophages[21], B cells in murine PC impede immunogenic chemotherapy by suppressing CTL activation.

Example 5: IgA$^+$ Plasma Cells in Human Prostate Cancer

Figure 11:
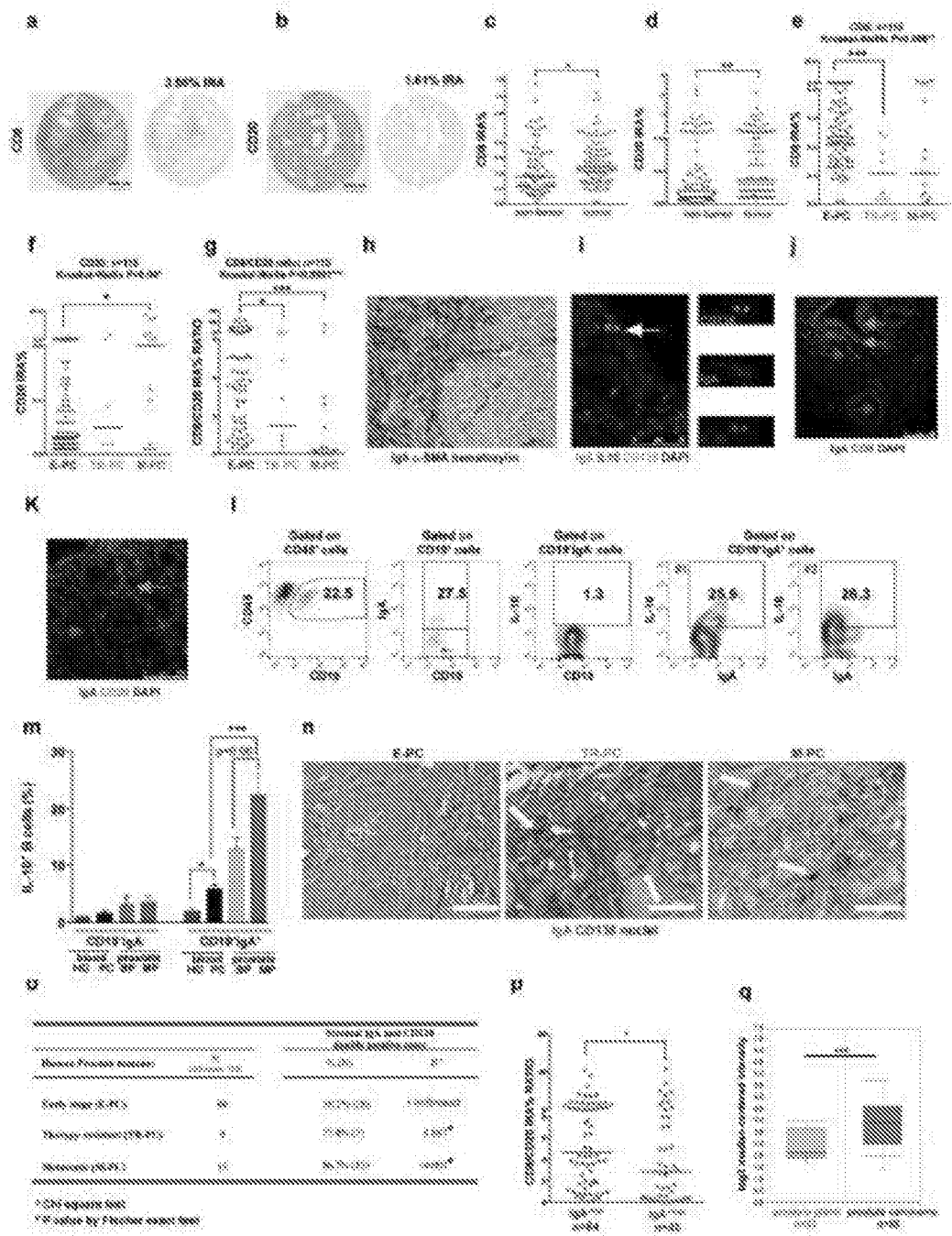
FIG. 11: Analyses of B and T cells in human prostate cancer specimens. a-h, Tissue microarrays of tumor and non-tumor tissue from 110 PC patients were stained for CD8 and CD20 (5-6 spots per patient=3-4 tumor tissue+2 non-tumor tissue). a,b, Representative examples of CD8 (a) and CD20 (b) IHC of PC tissue microarrays (left). Magnification bar: 200□m. Right, computer assisted image analysis with ad hoc developed image software. Tumor tissue is represented in yellow and CD8$^+$ and CD20$^+$ cells are represented in red. The percentages of immune reactive area (IRA) occupied by CD8$^+$ or CD20$^+$ cells are shown. Magnification bars: 200 □m. c,d, comparison of CD8 and CD20 IRAs in matched non-tumor and tumor tissues from each early stage PC (E-PC) patient (n=87). e-h, Patients were divided into three subgroups: E-PC (n=86); therapy-resistant-PC (TR-PC; n=9), and metastatic-PC (M-PC; n=15). e, CD8$^+$ cell infiltration into tumor tissues of the different groups. f, CD20$^+$ cell infiltration into tumor tissues of the different groups. g, The CD8$^+$/CD20$^+$ ratio for the different groups. h, The CD20$^+$/CD8$^+$ ratio for the different groups. Each dot represents one patient. Line indicates the median value. Mann-Whitney test was used to calculate statistical significance between the two groups. Kruskal-Wallis test was used to calculate statistical significance between the three groups. i, IHC analysis of low risk (n=5) and high risk (n=5) human PC specimens using IgA (red) and αSMA (black). Nuclei were counterstained with hematoxylin. Magnification bar: 100 μm j, IF analysis of human PC showing IL-10 (red)-expressing IgA$^+$ (green) CD138$^+$ (turquoise) plasma cells (n=6). Representative images are shown. White arrow indicates IL-10-expressing IgA$^+$ cells. Magnification bars: 50 □m. k, Human normal prostate (n=3-5), and human PC (n=5), were stained for IgA and CD8. Typical images are shown. Red and green arrows indicate IgA$^+$ and CD8$^+$ cells, respectively. Magnification bar: 100 □m. l, Human normal prostate (n=3), and human PC (n=5), were stained for IgA (red arrow) and CD20 (green arrow). Magnification bar: 100□m. m, Flow cytometric analysis of human prostate tumor-infiltrating CD19$^+$ B cells and IgA$^+$ cells. The percentages of IL-10-expressing B cells in CD19$^+$IgA$^+$ (2 different samples) and CD19$^+$IgA$^-$ B cells are shown. n, Summary of results obtained from human blood samples taken from healthy donors (n=3) and PC patients (n=5) and prostate tissue specimens (benign, malignant; n=4) analyzed by flow cytometry for IL-10 expression in CD19$^+$IgA$^-$ and CD19$^+$IgA$^+$ B cells. o,p, Tissue microarrays from 110 PC patients (described above) were stained for IgA and CD138. Patients were divided into three subgroups: E-PC (n=86); TR-PC (n=9), and M-PC (n=15). (o) Representative images of IgA (immunoperoxidase) and CD138 (alkaline phosphatase) double staining of tumor tissues from each group. CD138$^+$ and IgA$^+$ double positive cells in the PC stroma are indicated by the white arrows (hematoxylin counterstain). Magnification bar: 100 □m. p, Frequencies of IgA$^+$ and CD138$^+$ double positive cells in the tumor stroma of the different PC patient groups. q, PC patient specimens were divided into two groups: IgA$^{-/low}$ (n=64) and IgA$^{+/hi}$ (n=46). Shown is the CD8$^+$/CD20$^+$ ratio for each group. Each dot represents one patient. Line indicates the median value. r, IgA mRNA expression (IGHA1) is significantly elevated in human PC tissue relative to healthy or benign prostate tissue in 5 out of 15 studies evaluated via Oncomine. Results from one significant study[14] are presented. Chi square test and Fischer exact test were used to calculate statistical significance shown by *P, 0.05; P, 0.01; *P, 0.001.

Human PC samples (n=110) were analyzed for CD8$^+$ T cells and CD20$^+$ B cells (FIG. 11a,b). Comparison of CD8 and CD20 immune reactive areas (IRA) in matched normal versus tumor tissue specimens from 87 early stage PC (E-PC) patients indicated higher CD8$^+$ and CD20$^+$ cell counts in tumor tissue (FIG. 11c,d). Moreover, patients with therapy-resistant PC (TR-PC) or metastatic PC (M-PC) exhibited reduced tumoral CD8 cell density relative to E-PC patients (FIG. 11e). By contrast, E-PC contained fewer B cells than TR-PC and M-PC, where B cells were most abundant (FIG. 11f). E-PC specimens displayed higher CD8/CD20 ratio and lower CD20/CD8 ratio than TR-PC and M-PC (FIG. 11g,h). Immunofluorescence (IF) and immunohistochemical (IHC) analyses of human PC specimens revealed IgA$^+$ cells in a scattered formation, especially in the high risk group, frequently next to αSMA$^+$ myofibroblasts (FIG. 3m; FIG. 11i-k, and o), as found in mice. CD20$^+$ B cells were found both scattered and clustered in lymphoid follicle-like[16] areas (FIG. 11b,l). IL-10-producing IgA$^+$ CD138$^+$ cells were also detected in human PC and some IgA$^+$ cells were adjacent to CD8$^+$ T cells and expressed little CD20 (FIG. 11j-l). Approximately 25% of the IgA$^+$ cells in fresh prostatectomy specimens expressed IL-10 and they were enriched in the malignant portion of the prostate (FIG. 11m,n). IgA$^+$CD138$^+$ plasmocytes exhibited higher density in TR-PC and M-PC than in E-PC (FIG. 11o,p) and patients with higher IgA$^+$CD138$^+$ cell counts showed lower CD8/CD20 ratio (FIG. 11q). In silico analysis of human IgA (IGIA1) mRNA in PC Oncomine datasets[22] revealed elevated IGHA1 mRNA in malignant versus healthy prostates in 11 of 15 datasets. Of these, 5 showed a significant increase (p<0.05) and 3 showed a >2-fold change. Results of one analysis[23] are presented (FIG. 11r) and are consistent with earlier findings regarding lymphocyte infiltration and activation of the IKKα-Bmi1 module by B cells in mouse PC[7,8,24], suggesting that tumor infiltrating lymphocytes also control malignant progression and response to therapy in human PC.

Example 6: Immunosuppressive Plasmocytes Depend on TGFβ Signaling, PD-L1 and IL-10

We examined mechanisms responsible for generation of tumoral IgA$^+$ plasmocytes and their immunosuppressive function. Consistent with prior knowledge regarding the IgA CSR[17,25] and presence of activated SMAD2/3 in PD-L1-expressing B cells, TGFβ receptor II (TGFβR2)[26] ablation in B cells (Tgfbr2$^{ΔB}$) enhanced the response of MC tumors to oxaliplatin (FIG. 4a), decreased the number of tumor-infiltrating, but not splenic, B cells (FIG. 4b and FIG. 12a) and inhibited oxaliplatin-induced IgA$^+$ plasmocyte generation without affecting IgG1$^+$ or IgG2a$^+$ cells (FIG. 4c; FIG. 12b-d). IgA ablation also potentiated the response to oxaliplatin without reducing tumoral B cell number (FIG. 4a,b). Both TGFβR2 and IgA ablations increased serum IgG independently of oxaliplatin, prevented appearance of tumoral PD-L1$^+$ or IgA$^+$IL-10$^+$ B cells after oxaliplatin treatment, but had almost no effect on IL-10 production by B220$^{hi}$IgA$^+$ IL-10$^+$ B cells (FIG. 12e-g). TGFβR2 ablation in B cells or IgA deficiency also increased tumoral CTL density, tumoral IFNγ-production and surface CD107a expression by CD8$^+$ T cells isolated from oxaliplatin-treated mice after ex vivo stimulation with MC lysates or PMA/ionomycin (FIG. 4e,f). These results are consistent with clinical observations, describing systemic and organ-specific autoimmune diseases as major manifestations of IgA deficiency[27], which suggest that IgA$^+$ cells suppress activation of auto-reactive T cells.

Suppressor B cells may attenuate T cell activation via PD-L1[25]. Treatment of mice bearing MC tumors with a combination of oxaliplatin and anti-PD-L1, but not anti-PD-L1 alone, inhibited tumor growth, increased GrzB expression by effector T cells, downregulated PD-L1 expression on IgA$^+$ B cells, and reduced serum IgA, but not IgG (FIG. 12h-m). Furthermore, reconstitution of MC tumor-bearing Jh$^{-/-}$ hosts with B cells deficient in either PD-L1 or IL-10 failed to inhibit oxaliplatin-induced tumor regression (FIG. 4g,h; FIG. 12n,o). PD-L1 ablation did not affect IL-10 expression and IL-10 ablation had no effect on PD-L1 (FIG. 15j,k), indicating that both molecules are needed for plasmocyte-mediated immunosuppression.

Figure 13:
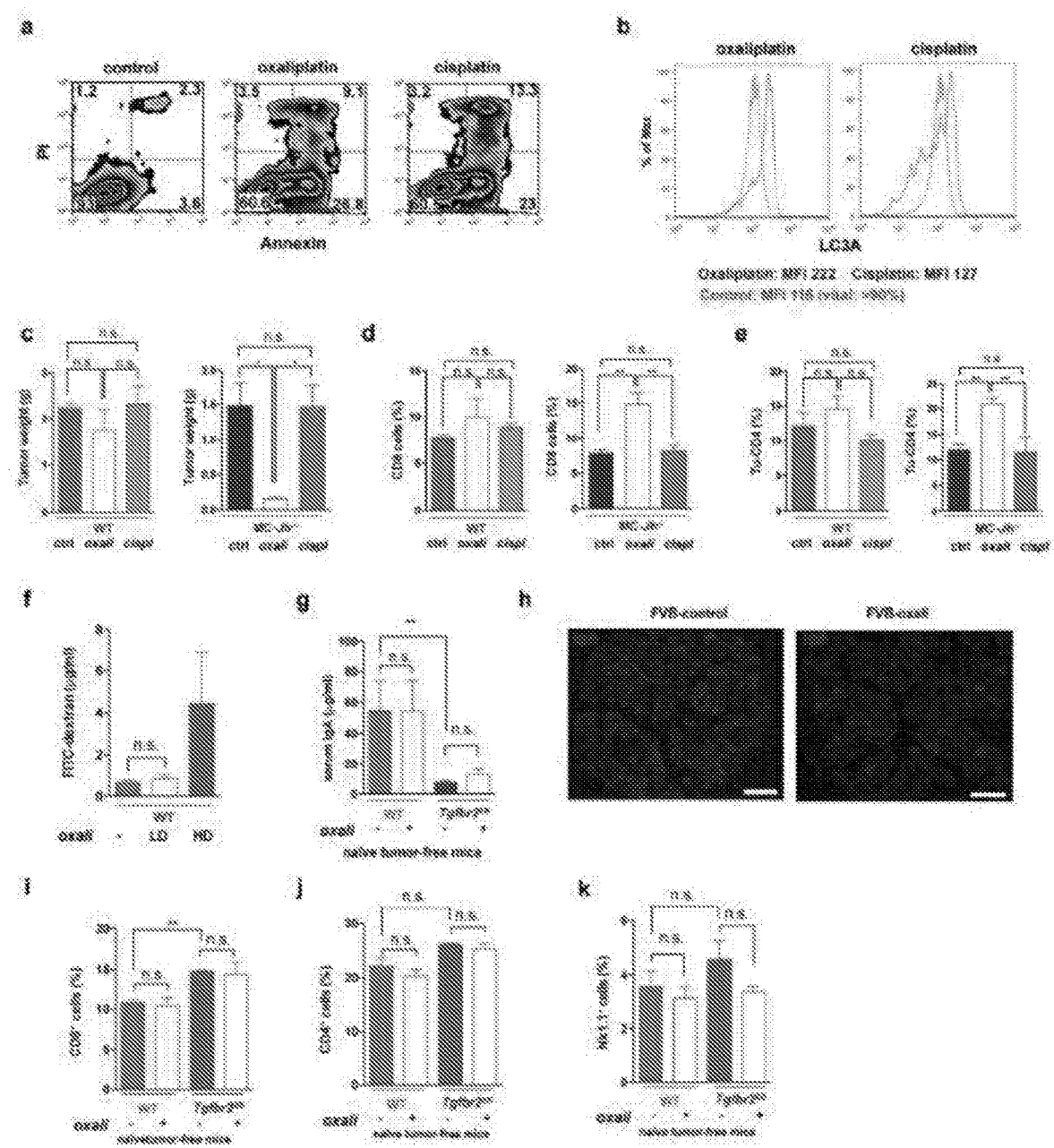
FIG. 13: Low dose cisplatin treatment is devoid of immunogenic activity and low dose oxaliplatin does not affect gut barrier function. a, Flow cytometry of MC cells stained with Annexin V and propidium iodide 24 hrs after treatment with either oxaliplatin or cisplatin (both at 20 □M). b, Flow cytometry analysis of MC cells treated as above and stained with antibody to the autophagy marker LC3A. c-e, MC tumors were raised in WT and Jh$^{-/-}$ mice until 400 mm$^3$ in size, after which the mice were treated with either cisplatin or oxaliplatin at 6 mg/kg (n=4-5 per group). After 3 weekly chemotherapy cycles, mice were sacrificed. c, Tumor weights; left panel: WT mice; right panel: Jh$^{-/-}$ mice. d, e, Flow cytometry of tumor-infiltrating CD8 (d) and CD4 (e) cells. Left panel: WT mice, right panel: Jh$^{-/-}$ mice. f, Gut permeability was measured in WT mice before and after low (LD) and high (HD) dose oxaliplatin treatment using orally administered fluorescein isothiocyanate (FITC)-dextran. Shown are FITC-dextran concentrations in serum (μg/ml) (n=5 mice per group). g, Serum IgA concentrations in naïve WT (FVB) and Tgfbr2$^{ΔB}$ mice before and after oxaliplatin treatment. h, IgA staining of colon sections of untreated or LD oxaliplatin-treated WT mice. Magnification bars: 100 μm. i-k, Flow cytometry of CD8$^+$ (l), CD4$^+$ (j) and Nk1.1$^+$ (k) cells in spleens of naïve WT and Tgfbr2$^Δ$ mice without or with oxaliplatin treatment. All results are means±s.e.m. Mann-Whitney and t tests were used to calculate statistical significance shown as *P, 0.05; P, 0.01; *P, 0.001.

All of the above experiments used LD oxaliplatin because of its well-described immunogenic properties[4,5]. The related compound cisplatin, however, is devoid of immunogenic activity[4,5,28] Although both oxaliplatin and cisplatin induced apoptotic cell death of MC cells, oxaliplatin, was more effective in stimulating autophagy (FIG. 13a,b). Importantly, only LD oxaliplatin led to regression of MC tumors raised in Jh$^{-/-}$ mice, whereas LD cisplatin was ineffective (FIG. 13c). Correspondingly, only oxaliplatin increased the abundance of tumor infiltrating CD8$^+$ and CD4$^+$ cells in Jh$^{-/-}$ mice (FIG. 13d,e). LD, but not high dose, oxaliplatin did not increase intestinal permeability and had no effect on IgA production and other immune parameters in tumor-free WT or Tgfbr2$^{ΔB}$ mice (FIG. 13f-k).

Figure 14:
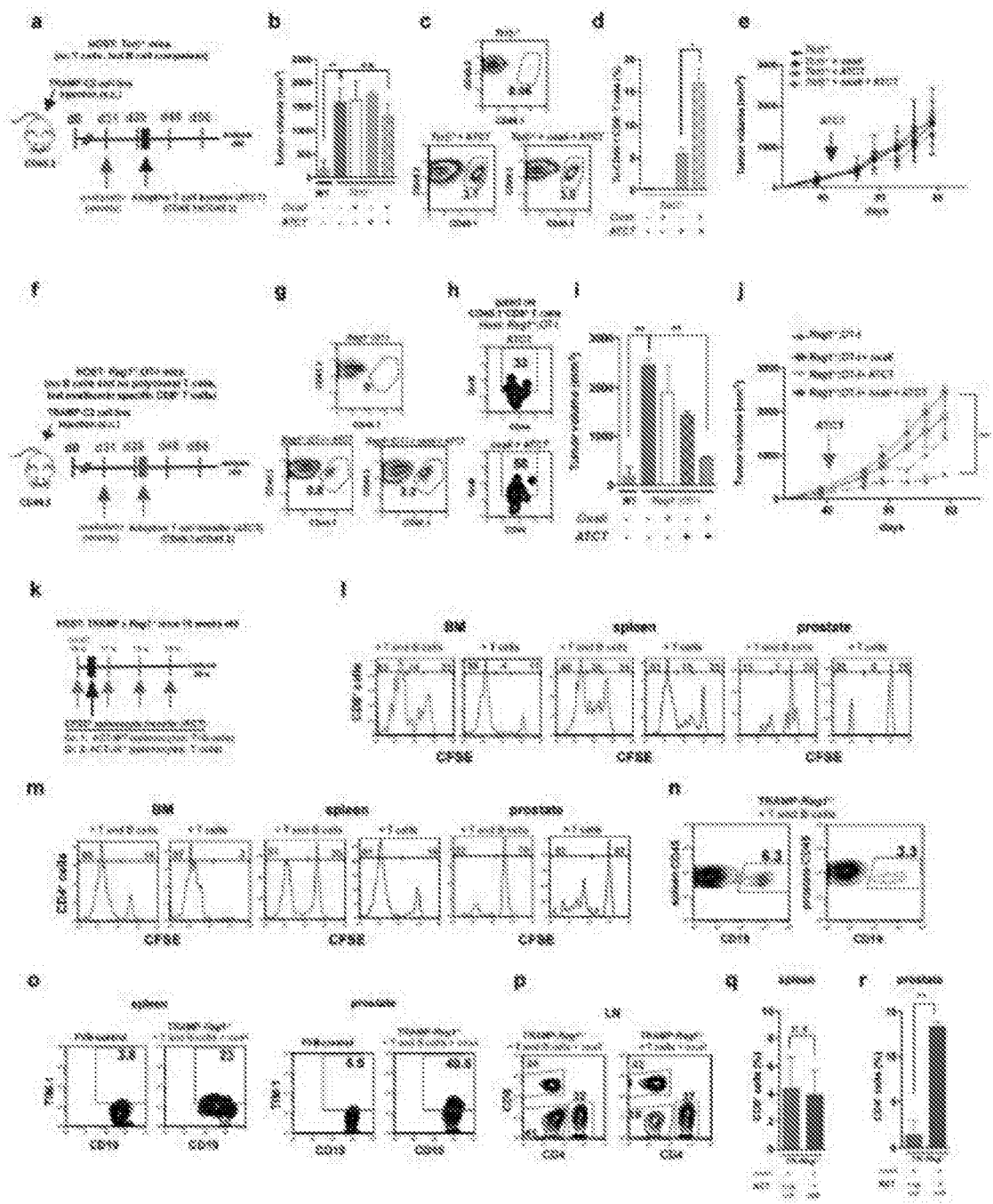
FIG. 14: Immunogenic chemotherapy supports adoptive T cell transfer only in the absence of B cells. a, The experimental scheme. Immunogenic TRAMP-C2 cells were s.c.

Example 7: Adoptively Transferred T Cells Eliminate Tumors in the Absence of B Cells We examined whether immunogenic chemotherapy also potentiates the effectiveness of adoptively transferred T cells (ATCT). We grew immunogenic TRAMP-C2 PC cells[29] in B cell-containing Tcrβ$^{-/-}$ mice and combined oxaliplatin treatment with ATCT (FIG. 14a). Higher tumor volumes in Tcrβ$^{-/-}$ relative to WT mice confirmed TRAMP-C2 immunogenicity (FIG. 14b). However, despite successful T cell take and elevated CD8$^+$ cell count after oxaliplatin no tumor rejection took place (FIG. 14c-e). Different results were obtained in Rag1$^{-/-}$ mice, which lack T and B cells (FIG. 14f). We raised TRAMP-C2 tumors in Rag1$^{-/-}$; OT-1 mice, which lack B cells and polyclonal T cells but harbor CD8$^+$ T cells directed against chicken ovalbumin (Ova)[30]. These mice were used instead of simple Rag1$^{-/-}$ mice to avoid lymphopenia-induced proliferation of CD8$^+$ cells, which can non-specifically increase T cell effector function[31]. Adoptively transferred CD8$^+$ T cells expanded and expressed GrzB in Rag1$^{-/-}$; OT-1 hosts, especially after oxaliplatin treatment (FIG. 14g,h). Consequently, tumor growth was inhibited in mice receiving ATCT together with oxaliplatin (FIG. 14i,j).

More dramatic results were obtained in TRAMP; Rag1$^{-/-}$ mice transplanted with CFSE-labeled splenocytes from either naïve WT (B and T cell transfer) or Jh$^{-/-}$ (T cell transfer) mice at 16 weeks of age (FIG. 5a). Six days later, CD8$^+$ cell proliferation was confirmed in BM, spleens and prostates of transplanted mice, indicating successful T cell take, although lower T cell proliferation was seen when T and B cells were co-transferred (FIG. 14k,l). Thirty days after lymphocyte transfer, prostate tumors were analyzed. Oxaliplatin led to tumor regression in mice receiving T and B cells, but in mice receiving only T cells it induced complete tumor regression (FIG. 5b,c). Transplantation with both T and B cells combined with oxaliplatin treatment led to appearance of CD19$^+$ B cells in spleen and prostate and restored serum IgA and IgG (FIG. 5d-f). IgA and IgG directed against SV40 T antigen, the TRAMP oncogene, were detected after B and T cell transfer, indicating a tumor-specific humoral response (FIG. 5g,h). Transferred B cells showed higher expression of TIM-1 (FIG. 14m,n), a molecule involved in regulation of IL-10 expression and tolerance induction[32]. Co-transplantation of B and T cells also led to appearance of CD4$^+$ and CD8 cells in lymph nodes and spleen, but T cell number was considerably lower in prostate tumors (FIG. 5i; FIG. 14o-q). However, transplantation with B cell-deficient splenocytes led to robust T cell infiltration into prostate tumors (FIG. 5i; FIG. 14q). To further confirm that IgA+ B cells attenuate the response to immunogenic chemotherapy by inhibiting T cell activation, we raised MC tumors in Rag1$^{-/-}$ mice and transplanted the mice with T cells from WT mice that were immunized with MC cell lysate, with or without naïve splenic B cells from WT or Tgfbr2$^{ΔB}$ mice. In this case, oxaliplatin induced tumor regression and CTL activation only in mice receiving T cells, or T cells+TGFβR2-deficient B cells, which produced just a low amount of IgA (FIG. 5j-l; FIG. 14r-t). Hence, only B cells that have undergone TGFβR signaling and IgA CSR suppress CTL activation.

Example 8: Anti-PD-L Treatment Induce Hepatocellular Carcinoma Tumor Regression Only when Combined with Oxaliplatin Liver cancer rates are rapidly growing while all other cancers are declining (Ryerson et al. (2016), Annual Report to the Nation on the Status of Cancer, 1975-2012, Cancer. doi: 10.1002/cncr.29936). FIG. 16 shows that immunosuppressive B cells are indeed also present in liver cancer, and the combination therapy of oxaliplatin with checkpoint inhibitor (aPDL1) decreased the number of liver tumors.

REFERENCES CITED IN EXAMPLE 1, MATERIALS AND METHODS

1. Chen, D. S. & Mellman, I. Oncology meets immunology: the cancer-immunity cycle. *Immunity* 39, 1-10 (2013).
2. Schreiber, R. D., Old, L. J. & Smyth, M. J. Cancer immunoediting: integrating immunity's roles in cancer suppression and promotion. *Science* 331, 1565-1570 (2011).
3. Schietinger, A. & Greenberg, P. D. Tolerance and exhaustion: defining mechanisms of T cell dysfunction. *Trends Immunol* 35, 51-60 (2014).
4. Zitvogel, L., Galluzzi, L., Smyth, M. J. & Kroemer, G. Mechanism of action of conventional and targeted anticancer therapies: reinstating immunosurveillancce. *Immunity* 39, 74-88 (2013).
5. Kroemer, G., Galluzzi, L., Kepp, O. & Zitvogel, L. Immunogenic cell death in cancer therapy. *Annu Rev Immunol* 31, 51-72 (2013).
6. Krysko, D. V., et al. Immunogenic cell death and DAMPs in cancer therapy, *Nat Rev Cancer* 12, 860-875 (2012).
7. Ammirante, M., Luo, J. L., Grivennikov, S., Nedospasov, S. & Karin, M. B-cell-derived lymphotoxin promotes castration-resistant prostate cancer. *Nature* 464, 302-305 (2010).
8. Ammirante, M., et al. An IKKalpha-E2F1-BMI1 cascade activated by infiltrating B cells controls prostate regeneration and tumor recurrence. *Genes Dev* 27, 1435-1440 (2013).
9. Lee, J. L., et al. Gemcitabine-oxaliplatin plus prednisolone is active in patients with castration-resistant prostate cancer for whom docetaxel-based chemotherapy failed. *Br J Cancer* 110, 2472-2478 (2014).
10. Matos, C. S., de Carvalho, A. L., Lopes. R. P. & Marques, M. P. New strategies against prostate cancer—Pt(II)-based chemotherapy. *Curr Med Chem* 19, 4678-4687 (2012).
11. Kaplan-Lefko, P. J., et al. Pathobiology of autochthonous prostate cancer in a pre-clinical transgenic mouse model. *Prostate* 55, 219-237 (2003).
12. Chen, J., et al. Immunoglobulin gene rearrangement in B cell deficient mice generated by targeted deletion of the JH locus. *Int Immunol* 5, 647-656 (1993).
13. Koh, D. R., et al. Less mortality but more relapses in experimental allergic encephalomyelitis in CD8−/− mice. *Science* 256, 1210-1213 (1992).
14. Watson, P. A., et al. Context-dependent hormone-refractory progression revealed through characterization of a novel murine prostate cancer cell line. *Cancer Res* 65, 11565-11571 (2005).
15. Fagarasan, S., Kinoshita, K., Muramatsu, M., Ikuta, K. & Honjo, T. In situ class switching and differentiation to IgA-producing cells in the gut lamina propria. *Nature* 413, 639-643 (2001).
16. Ammirante, M., Shalapour, S., Kang, Y., Jamieson, C. A. & Karin, M. Tissue injury and hypoxia promote malignant progression of prostate cancer by inducing CXCL13 expression in tumor myofibroblasts. *Proc Natl Acad Sci USA* 111, 14776-14781 (2014).
17. Cazac, B. B. & Roes, J. TGF-beta receptor controls B cell responsiveness and induction of IgA in vivo. *Immunity* 13, 443-451 (2000).
18. Cerutti, A. The regulation of IgA class switching. *Nat Rev Immunol* 8, 421-434 (2008).
19. Yoshizaki, A., et al. Regulatory B cells control T-cell autoimmunity through IL-21-dependent cognate interactions. *Nature* 491, 264-268 (2012).
20. Tugues, S., et al. New insights into IL-12-mediated tumor suppression. *Cell Death Differ* 22, 237-246 (2015).
21. Affara, N. I., et al. B cells regulate macrophage phenotype and response to chemotherapy in squamous carcinomas. *Cancer Cell* 25, 809-821 (2014).
22. Rhodes, D. R., et al. ONCOMINE: a cancer microarray database and integrated data-mining platform. *Neoplasia* 6, 1-6 (2004).
23. Yu, Y. P., et al. Gene expression alterations in prostate cancer predicting tumor aggression and preceding development of malignancy. *J Clin Oncol* 22, 2790-2799 (2004).
24. Luo, J. L, et al. Nuclear cytokine-activated IKKalpha controls prostate cancer metastasis by repressing Maspin. *Nature* 446, 690-694 (2007).
25. Doi, T., et al. IgA plasma cells express the negative regulatory co-stimulatory molecule programmed cell death 1 ligand and have a potential tolerogenic role in the intestine. *Biochem Biophys Res Commun* 425, 918-923 (2012).
26. Forrester, E., et al. Effect of conditional knockout of the type II TGF-beta receptor gene in mammary epithelia on mammary gland development and polyomavirus middle T antigen induced tumor formation and metastasis. *Cancer Res* 65, 2296-2302 (2005).
27. Ludvigsson, J. F., Neovius, M. & Hammarstrom, L. Association between IgA deficiency & other autoimmune conditions: a population-based matched cohort study. *J Clin Immunol* 34, 444-451 (2014).
28. Tesniere, A., et al. Immunogenic death of colon cancer cells treated with oxaliplatin. *Oncogene* 29, 482-491 (2010).
29. Foster, B. A., Gingrich, J. R., Kwon, E.D., Madias, C. & Greenberg, N. M. Characterization of prostatic epithelial cell lines derived from transgenic adenocarcinoma of the mouse prostate (TRAMP) model. *Cancer Res* 57, 3325-3330 (1997).

30. Hogquist, K. A., et al. T cell receptor antagonist peptides induce positive selection. *Cell* 76, 17-27 (1994).
31. Dummer, W., et al. T cell homeostatic proliferation elicits effective antitumor autoimmunity. *J Clin Invest* 110, 185-192 (2002).
32. Xiao, S., et al. Defect in regulatory B-cell function and development of systemic autoimmunity in T-cell Ig mucin 1 (Tim-1) mucin domain-mutant mice. *Proc Natl Acad Sci USA* 109, 12105-12110 (2012).
33. Grivennikov, S. I., Greten, F. R. & Karin, M. Immunity, inflammation, and cancer. *Cell* 140, 883-899 (2010).
34. Gajewski, T. F., Schreiber, H. & Fu, Y. X. Innate and adaptive immune cells in the tumor microenvironment. *Nat Immunol* 14, 1014-1022 (2013).
35. Tan, W., et al. Tumour-infiltrating regulatory T cells stimulate mammary cancer metastasis through RANKL-RANK signalling. *Nature* 470, 548-553 (2011).
36. Sharma, P., Wagner, K., Wolchok, J. D. & Allison, J. P. Novel cancer immunotherapy agents with survival benefit: recent successes and next steps. *Nat Rev Cancer* 11, 805-812 (2011).
37. Pardoll, D. M. The blockade of immune checkpoints in cancer immunotherapy. *Nat Rev Cancer* 12, 252-264 (2012).
38. Kalos, M. & June, C. H. Adoptive T cell transfer for cancer immunotherapy in the era of synthetic biology. *Immunity* 39, 49-60 (2013).
39. Donkor, M. K., et al. T cell surveillance of oncogene-induced prostate cancer is impeded by T cell-derived TGF-beta1 cytokine. *Immunity* 35, 123-134 (2011).
40. Kang, H. S., et al. Signaling via LTbetaR on the lamina propria stromal cells of the gut is required for IgA production. *Nat Immunol* 3, 576-582 (2002).
41. Feng, T., Elson, C. O. & Cong, Y. Treg cell-IgA axis in maintenance of host immune homeostasis with microbiota. *Int Immunopharmacol* 11, 589-592 (2011).
42. Lundy, S. K. Killer B lymphocytes: the evidence and the potential. *Inflamm Res* 58, 345-357 (2009).
43. Qin, Z., et al. B cells inhibit induction of T cell-dependent tumor immunity. *Nat Med* 4, 627-630 (1998).
44. Olkhanud, P. B., et al. Tumor-evoked regulatory B cells promote breast cancer metastasis by converting resting CD4(+) T cells to T-regulatory cells. *Cancer Res* 71, 3505-3515 (2011).
45. Fremd, C., Schuetz, F., Sohn, C., Beckhove, P. & Domschke, C. B cell-regulated immune responses in tumor models and cancer patients. *Oncoimmunology* 2, c25443 (2013).
46. Zhang, Y., et al. B lymphocyte inhibition of anti-tumor response depends on expansion of Treg but is independent of B-cell IL-10 secretion. *Cancer Imunol Immunother* 62, 87-99 (2013).
47. Shah, N. Diagnostic significance of levels of immunoglobulin A in seminal fluid of patients with prostatic disease. *Urology* 8, 270-272 (1976).
48. Powles, T., et al. MPDL3280A (anti-PD-L1) treatment leads to clinical activity in metastatic bladder cancer. *Nature* 515, 558-562 (2014).
49. Herbst, R. S., et al. Predictive correlates of response to the anti-PD-L1 antibody MPDL3280A in cancer patients. *Nature* 515, 563-567 (2014).
50. Tumeh. P. C., et al. PD-1 blockade induces responses by inhibiting adaptive immune resistance. *Nature* 515, 568-571 (2014).

REFERENCES CITED IN THE SPECIFICATION, OTHER THAN IN EXAMPLE 1, MATERIALS AND METHODS

1. Shen, F. W., et al. Cloning of Ly-5 cDNA. *Proc Natl Acad Sci USA* 82, 7360-7363 (1985).
2. Gingrich, J. R., et al. Metastatic prostate cancer in a transgenic mouse. *Cancer Res* 56, 4096-4102 (1996).
3. Chen, J., et al. Immunoglobulin gene rearrangement in B cell deficient mice generated by targeted deletion of the JH locus. *Int Immunol* 5, 647-656 (1993).
4. Koh, D. R., et al. Less mortality but more relapses in experimental allergic encephalomyelitis in CD8−/− mice. *Science* 256, 1210-1213 (1992).
5. Mombaerts, P., et al. RAG-1-deficient mice have no mature B and T lymphocytes. *Cell* 68, 869-877 (1992).
6. Hogquist, K. A., et al. T cell receptor antagonist peptides induce positive selection. *Cell* 76, 17-27 (1994).
7. Forrester, E., et al. Effect of conditional knockout of the type II TGF-beta receptor gene in mammary epithelia on mammary gland development and polyomavirus middle T antigen induced tumor formation and metastasis. *Cancer Res* 65, 2296-2302 (2005).
8. Harriman, G. R., et al. Targeted deletion of the IgA constant region in mice leads to IgA deficiency with alterations in expression of other Ig isotypes. *J Immunol* 162, 2521-2529 (1999).
9. Porichis, F., et al. High-throughput detection of miRNAs and gene-specific mRNA at the single-cell level by flow cytometry. *Nat Commun* 5 (2014).
10. Michaud, M., et al. Autophagy-dependent anticancer immune responses induced by chemotherapeutic agents in mice. *Science* 334, 1573-1577 (2011).
11. Ammirante, M., Luo, J. L., Grivennikov, S., Nedospasov, S. & Karin, M. B-cell-derived lymphotoxin promotes castration-resistant prostate cancer. *Nature* 464, 302-305 (2010).
12. Foster, B. A., Gingrich, J. R., Kwon, E.D., Madias, C. & Greenberg, N. M. Characterization of prostatic epithelial cell lines derived from transgenic adenocarcinoma of the mouse prostate (TRAMP) model. *Cancer Res* 57, 3325-3330 (1997).
13. Keren, Z., et al. B-cell depletion reactivates B lymphopoiesis in the BM and rejuvenates the B lineage in aging. *Blood* 117, 3104-3112 (2011).
14. Yu, Y. P., et al. Gene expression alterations in prostate cancer predicting tumor aggression and preceding development of malignancy. *J Clin Oncol* 22, 2790-2799 (2004).
15. Holzbeierlein, J., et al. Gene expression analysis of human prostate carcinoma during hormonal therapy identifies androgen-responsive genes and mechanisms of therapy resistance. *Am J Pathol* 164, 217-227 (2004).
16. LaTulippe, E., et al. Comprehensive gene expression analysis of prostate cancer reveals distinct transcriptional programs associated with metastatic disease. *Cancer Res* 62, 4499-4506 (2002).
17. Singh, D., et al. Gene expression correlates of clinical prostate cancer behavior. *Cancer Cell* 1, 203-209 (2002).
18. Arredouani, M. S., et al. Identification of the transcription factor single-minded homologue 2 as a potential biomarker and immunotherapy target in prostate cancer. *Clin Cancer Res* 15, 5794-5802 (2009).
19. Liu, P., et al. Sex-determining region Y box 4 is a transforming oncogene in human prostate cancer cells. *Cancer Res* 66, 4011-4019 (2006).

20. Grasso, C. S., et al. The mutational landscape of lethal castration-resistant prostate cancer. *Nature* 487, 239-243 (2012).
21. Lapointe, J., et al, Gene expression profiling identifies clinically relevant subtypes of prostate cancer. *Proc Natl Acad Sci USA* 101, 811-816 (2004).
22. Tomlins, S. A., et al. Integrative molecular concept modeling of prostate cancer progression. *Nat Genet* 39, 41-51 (2007).
23. Welsh, J. B., et al. Analysis of gene expression identifies candidate markers and pharmacological targets in prostate cancer. *Cancer Res* 61, 5974-5978 (2001).
24. Varambally, S., et al. Integrative genomic and proteomic analysis of prostate cancer reveals signatures of metastatic progression. *Cancer Cell* 8, 393-406 (2005).
25. Magee, J. A., et al. Expression profiling reveals hepsin overexpression in prostate cancer. *Cancer Res* 61, 5692-5696 (2001).
26. Wallace, T. A., et al. Tumor immunobiological differences in prostate cancer between African-American and European-American men. *Cancer Res* 68, 927-936 (2008).
27. Vanaja, D. K., Cheville, J. C., Iturria, S. J. & Young, C. Y. Transcriptional silencing of zinc finger protein 185 identified by expression profiling is associated with prostate cancer progression. *Cancer Res* 63, 3877-3882 (2003).
28. Luo, J. H., et al. Gene expression analysis of prostate cancers. *Mol Carcinog* 33, 25-35 (2002).
29. Rhodes, D. R., et al. ONCOMINE: a cancer microarray database and integrated data-mining platform. *Neoplasia* 6, 1-6 (2004).
30. Di Caro, G., et al. Occurrence of tertiary lymphoid tissue is associated with T-cell infiltration and predicts better prognosis in early-stage colorectal cancers. *Clin Cancer Res* 20, 2147-2158 (2014).
31. Woo, J. R., et al. Tumor infiltrating B-cells are increased in prostate cancer tissue. *J Transl Med* 12, 30 (2014).
32. D'Amico, A. V., et al. Biochemical outcome after radical prostatectomy, external beam radiation therapy, or interstitial radiation therapy for clinically localized prostate cancer. *JAMA* 280, 969-974 (1998).
33. Czeh, M., et al. The immune response to sporadic colorectal cancer in a novel mouse model. *Oncogene* 29, 6591-6602 (2010).

We claim:

1. A method for treating epithelial cancer in a mammalian subject in need thereof, wherein said subject comprises cancer tissue that contains epithelial cancer cells and IgA$^+$ immunosuppressive B cells, and wherein said method comprises administering to said subject a therapeutically effective amount of
   a) a first composition comprising oxaliplatin in an amount that causes immunogenic cell death of said epithelial cancer cells, and that is non-myelosuppressive, and
   b) a second composition comprising anti-PDL1 antibody in an amount that reduces one or both of the number and function of said IgA$^+$ immunosuppressive B cells in said cancer, such that said administering produces a greater inhibition of said cancer than administering either said first composition in the absence of said second composition, or said second composition in the absence of said first composition.

2. The method of claim 1, wherein said second composition that reduces one or both of the number and function of said immunosuppressive B cells in said cancer comprises anti-CD19-CAR T cells.

3. The method of claim 1, wherein said immunosuppressive B cells comprise TGF beta receptors, and wherein said second composition that reduces one or both of the number and function of said immunosuppressive B cells in said cancer comprises a compound that inhibits binding of said TGF beta receptor to a TGF beta receptor ligand.

4. The method of claim 3, wherein said second composition that inhibits binding of said TGF beta receptor to a TGF beta receptor comprises ALK5 inhibitor.

5. The method of claim 1, wherein said epithelial cancer is selected from the group consisting of prostate cancer, liver cancer, bladder cancer, lung cancer, and cutaneous melanoma.

6. The method of claim 5, wherein said prostate cancer is selected from the group consisting of castrate-resistant prostate cancer (CRPC), recurrent prostate cancer, and metastatic prostate cancer.

7. The method of claim 1, wherein said epithelial cancer is selected from the group consisting of primary cancer, recurrent cancer, and metastatic cancer.

8. The method of claim 1, wherein said administering comprises administering said first composition and said second composition simultaneously.

9. The method of claim 1, wherein said administering comprises administering said first composition and said second composition sequentially in any order.

* * * * *

SEQUENCE LISTING

<160> NUMBER OF SEQ ID NOS: 33

<210> SEQ ID NO 1
<211> LENGTH: 290
<212> TYPE: PRT
<213> ORGANISM: Homo sapiens

<400> SEQUENCE: 1

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
```

```
                  210                 215                 220
Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 2
<211> LENGTH: 290
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285
```

Glu Thr
    290

<210> SEQ ID NO 3
<211> LENGTH: 176
<212> TYPE: PRT
<213> ORGANISM: Homo sapiens

<400> SEQUENCE: 3

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 4
<211> LENGTH: 178
<212> TYPE: PRT
<213> ORGANISM: Homo sapiens

<400> SEQUENCE: 4

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

```
Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp

<210> SEQ ID NO 5
<211> LENGTH: 102
<212> TYPE: PRT
<213> ORGANISM: Homo sapiens

<400> SEQUENCE: 5

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp
                100

<210> SEQ ID NO 6
<211> LENGTH: 353
<212> TYPE: PRT
<213> ORGANISM: Homo sapiens

<400> SEQUENCE: 6

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
                20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
                100                 105                 110

Ser Thr Pro Pro Thr Pro Ser Pro Ser Cys Cys His Pro Arg Leu Ser
            115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
```

-continued

```
            180                 185                 190
Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
        210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
        290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr
```

<210> SEQ ID NO 7
<211> LENGTH: 340
<212> TYPE: PRT
<213> ORGANISM: Homo sapiens

<400> SEQUENCE: 7

```
Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
```

```
            195                 200                 205
Ser Gly Asn Thr Phe Arg Pro Glu Val His Leu Leu Pro Pro Ser
    210                 215                 220
Glu Leu Ala Leu Asn Glu Leu Val Thr Leu Thr Cys Leu Ala Arg
225                 230                 235                 240
Gly Phe Ser Pro Lys Asp Val Leu Val Arg Trp Leu Gln Gly Ser Gln
                245                 250                 255
Glu Leu Pro Arg Glu Lys Tyr Leu Thr Trp Ala Ser Arg Gln Glu Pro
            260                 265                 270
Ser Gln Gly Thr Thr Thr Phe Ala Val Thr Ser Ile Leu Arg Val Ala
            275                 280                 285
Ala Glu Asp Trp Lys Lys Gly Asp Thr Phe Ser Cys Met Val Gly His
290                 295                 300
Glu Ala Leu Pro Leu Ala Phe Thr Gln Lys Thr Ile Asp Arg Met Ala
305                 310                 315                 320
Gly Lys Pro Thr His Val Asn Val Ser Val Val Met Ala Glu Val Asp
                325                 330                 335
Gly Thr Cys Tyr
            340
```

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
tgaacgctac acactgcatc t                                         21

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gactcctttt ccgcttcctg a                                         21

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ggtctgggcc atagaactga                                           20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
cagcctcttc tcattcctgc                                           20

<210> SEQ ID NO 12

<211> LENGTH: 20
<212> TYPE: DNA
<213> ORGANISM: Artificial Sequence
<220> FEATURE:
<223> OTHER INFORMATION: Synthetic

<400> SEQUENCE: 12
ggttgccaag ccttatcgga                                          20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
acctgctcca ctgccttgct                                          20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
tggaggtttt tgtaccaggc                                          20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tagccaattt tgcagctgag                                          20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
aagttggcat ggtagccctt                                          20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ggagagccct ggataccaac                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tccagggatt ctggaacatt                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
gaagaaaacc ccttgtgctg                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tttttccagc agaccagctt                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
catgagctcc aagccaaagt                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ctctcgaata aggaagcccc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ctgaccttgt ctctggcctc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
ttgtgagcaa tctcagcaca                                              20

<210> SEQ ID NO 25
<211> LENGTH: 20
<212> TYPE: DNA

```
<213> ORGANISM: Artificial Sequence
<220> FEATURE:
<223> OTHER INFORMATION: Synthetic

<400> SEQUENCE: 25
gggagcaaca agaaaaccaa                                                    20

<210> SEQ ID NO 26
<211> LENGTH: 25
<212> TYPE: DNA
<213> ORGANISM: Artificial Sequence
<220> FEATURE:
<223> OTHER INFORMATION: Synthetic

<400> SEQUENCE: 26
cccttgtctg tctggtagtc atctt                                              25

<210> SEQ ID NO 27
<211> LENGTH: 16
<212> TYPE: DNA
<213> ORGANISM: Artificial Sequence
<220> FEATURE:
<223> OTHER INFORMATION: Synthetic

<400> SEQUENCE: 27
ggaggcgatc tggccc                                                        16

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
gaggacttga agatgtacca g                                                  21

<210> SEQ ID NO 29
<211> LENGTH: 19
<212> TYPE: DNA
<213> ORGANISM: Artificial Sequence
<220> FEATURE:
<223> OTHER INFORMATION: Synthetic

<400> SEQUENCE: 29
ctatctgtgt gaggagggc                                                     19

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
gaccctgccc attgaactgg c                                                  21

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
caacgttgca tcctaggatc g                                                  21
```

```
<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
tgctgcataa tcagctacgg                                            20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
ccacggaaat tctctggttg                                            20
```